United States Patent
Nagase et al.

(10) Patent No.: US 10,442,802 B2
(45) Date of Patent: Oct. 15, 2019

(54) MORPHINAN DERIVATIVE

(71) Applicant: NIPPON CHEMIPHAR CO., LTD., Tokyo (JP)

(72) Inventors: Hiroshi Nagase, Ibaraki (JP); Hideaki Fujii, Tokyo (JP); Akiyoshi Saitoh, Tokyo (JP); Eriko Nakata, Saitama (JP); Masaaki Hirose, Saitama (JP); Isao Ooi, Saitama (JP); Kohei Hayashida, Saitama (JP)

(73) Assignee: NIPPON CHEMIPHAR CO., LTD., Tokyo (JP)

(*) Notice: Subject to any disclaimer, the term of this patent is extended or adjusted under 35 U.S.C. 154(b) by 0 days.

(21) Appl. No.: 15/558,026

(22) PCT Filed: Mar. 17, 2016

(86) PCT No.: PCT/JP2016/058475
§ 371 (c)(1),
(2) Date: Sep. 13, 2017

(87) PCT Pub. No.: WO2016/148232
PCT Pub. Date: Sep. 22, 2016

(65) Prior Publication Data
US 2018/0057493 A1  Mar. 1, 2018

(30) Foreign Application Priority Data
Mar. 17, 2015 (JP) .................. 2015-054079

(51) Int. Cl.
C07D 471/08 (2006.01)
A61K 31/485 (2006.01)

(52) U.S. Cl.
CPC .......... *C07D 471/08* (2013.01); *A61K 31/485* (2013.01)

(58) Field of Classification Search
CPC ............................ C07D 471/08; A61K 31/485
See application file for complete search history.

(56) References Cited

U.S. PATENT DOCUMENTS

| | | |
|---|---|---|
| 7,538,118 B2 | 5/2009 | Schutz |
| 8,952,030 B2 | 2/2015 | Nagase et al. |
| 9,624,223 B2 | 4/2017 | Nagase et al. |
| 2006/0287345 A1 | 12/2006 | Steckler et al. |

FOREIGN PATENT DOCUMENTS

| | | |
|---|---|---|
| JP | 2006522775 A | 10/2006 |
| RU | 2306314 C2 | 9/2007 |
| WO | 2001046192 A1 | 6/2001 |
| WO | 2008001859 A1 | 1/2008 |
| WO | 2013035833 A1 | 3/2013 |
| WO | 2014021273 A1 | 2/2014 |
| WO | 2014136305 A1 | 9/2014 |

OTHER PUBLICATIONS

WebMD, http://www.webmd.com/parkinsons-disease/guide/parkinsons-disease-prevention; 2018.*
Dahl, A., https://www.emedicinehealth.com/glaucoma_faqs/article_em.htm Nov. 17, 2017.*
Bardsley, A., "An overview of urinary incontinence." Practice Nursing 27.11 (2016): 537-545.*
Fujimura, M., "Characteristics of TRK-130 (Naltalimide), a novel opioid ligand, as a new therapeutic agent for overactive bladder." Journal of Pharmacology and Experimental Therapeutics 350.3 (2014): 543-551.*
Filliol et al., Mice deficient for d- and m-opioid receptors exhibit opposing alterations of emotional responses, Nature America Inc., 2000, pp. 195-200, vol. 25.
M. Mas Nieto et al., Physiological Control of Emotion-Related Behaviors by Endogenous Enkephalin Involves Essentially the Delta Opioid Receptors, Neuroscience, 2005, vol. 135, pp. 305-313.

(Continued)

*Primary Examiner* — John M Mauro
(74) *Attorney, Agent, or Firm* — Greenblum & Bernstein, P.L.C.

(57) ABSTRACT

A morphinan derivative represented by the following general formula (I):

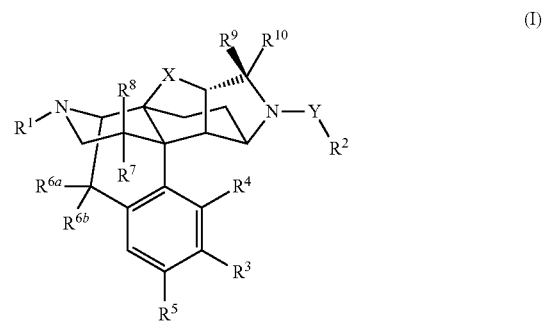

(wherein $R^1$ represents hydrogen, $C_{1-10}$ alkyl, cycloalkylalkyl where the cycloalkyl moiety has 3 to 6 carbon atoms, and the alkylene moiety has 1 to 5 carbon atoms, etc.,
$R^2$ represents heterocyclic ring containing 1 to 4 heteroatoms selected from N, O and S and at least one carbon atom as ring-constituting atoms, containing at least one set of adjacent ring-constituting atoms bound by a double bond, and further substituted with at least one oxo group,
Y binds to a carbon atom as a ring-constituting atom of $R^2$,
$R^3$, $R^4$, and $R^5$ represent hydrogen; hydroxy, etc.,
$R^{6a}$ and $R^{6b}$ represent hydrogen, etc.,
$R^7$ and $R^8$ represent hydrogen, etc.,
$R^9$ and $R^{10}$, which are the same or different, represent hydrogen, etc.,
X represents O or $CH_2$, and
Y represents C(=O)),
a tautomer or stereoisomer of the compound, or a pharmaceutically acceptable salt thereof, or a solvate thereof is used as an anxiolytic drug, antidepressant, etc.

83 Claims, 6 Drawing Sheets

(56) References Cited

OTHER PUBLICATIONS

T. J. Hudzik et al., Preclinical Pharmacology of AZD2327: A Highly Selective Agonist of the d-Opioid Receptor, the Journal of Pharmacology and Experimental Therapeutics, 2011, pp. 195-204, vol. 388 No. 1.

Lutz et al., Opioid Receptors: distinct roles in mood disorders, Trends in Neurosciences, 2013, pp. 195-206, vol. 36 No. 3, Elsevier Ltd.

Saitoh et al., The novel d opioid receptor agonist KNT-127 produces antidepressant-like and antinociceptive effects in mice without producing convulsions, Behavioural Brain Research, 2011, vol. 223, pp. 271-279.

Saitoh et al., The novel d opioid receptor agonist KNT-127 produces distinct anxiolytic-like effects in rats without producing the adverse effects associated with benzodiazepines, Neuropharmacology, 2013, vol. 67, pp. 485-493.

Saitoh et al., Antidepressant like Effects of d Opioid Receptor Agonists in Animal Models, Current Neuropharmacology, 2012, vol. 10 No. 3, pp. 231-238.

Richard M. Van Rijn et al., Pharmacological traits of delta opioid receptors: pitfall or opportunities?, Psychopharmacology, 2013.

Hayashida et al., Rearrangement of 4,5 α-epoxymorphinan derivatives with carbamoylepoxy rings provide novel oxazatricyclodecane structures, Tetrahedron, 2011, vol. 67, pp. 6682-6688.

Nakata et al., Opioid Delta Receptor-Mediated b-Arrestin Signaling Modulates Convulsive Effects, the International Narcotics Research Conference, Jul. 13, 2014.

International Search Report from Application No. PCT/JP2016/058475 dated Aug. 9, 2016.

International Preliminary Report on Patentability from Application No. PCT/JP2016/058475 dated Sep. 19, 2017.

Written Opinion of the International Searching Authority from Application No. PCT/JP2016/058475 dated Aug. 9, 2016.

European Search Report issued with respect to Application No. 16765061.3, dated Jul. 6, 2018.

Office Action dated Aug. 1, 2019 in corresponding Chinese Patent Application No. 201680016083.0.

"Medicinal Chemistry," Youqidong, Chemical Industry Press, Jan. 31, 2004, pp. 32-33. Concise statement of relevance provided by Office Action in corresponding Chinese Patent Application No. 201680016083.0.

Russian Office Action, Russian Patent Office, Application No. 2017134286/04(060439), dated Apr. 18, 2019, with English translation.

* cited by examiner

[Figure 1.]
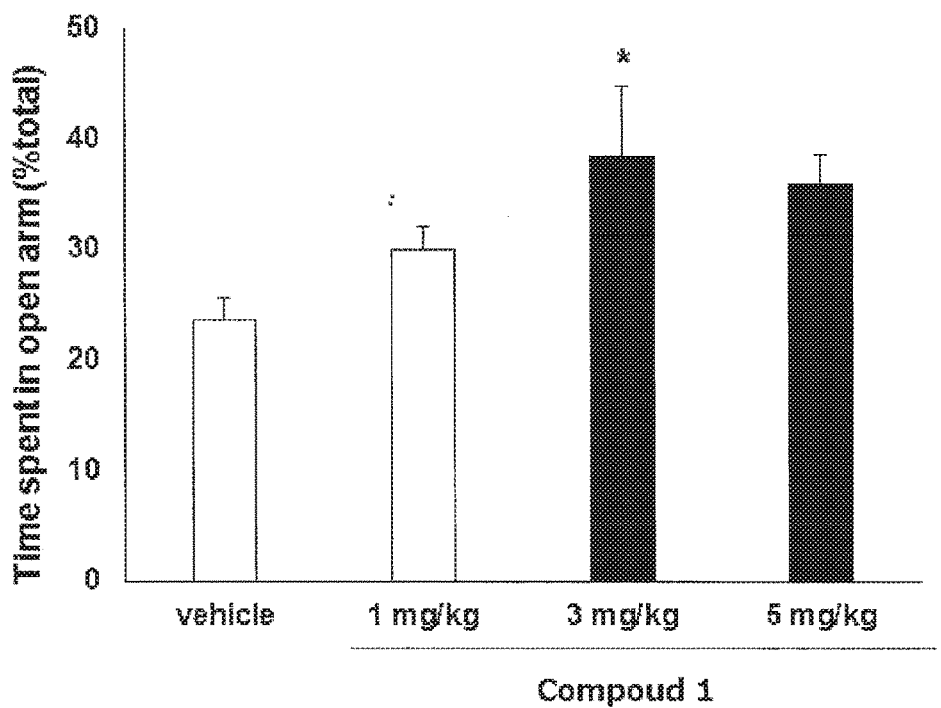
mean ± S.E. (n=8~10), *; p < 0.05 vs. vehicle (Dunnett test)

[Figure 2.]
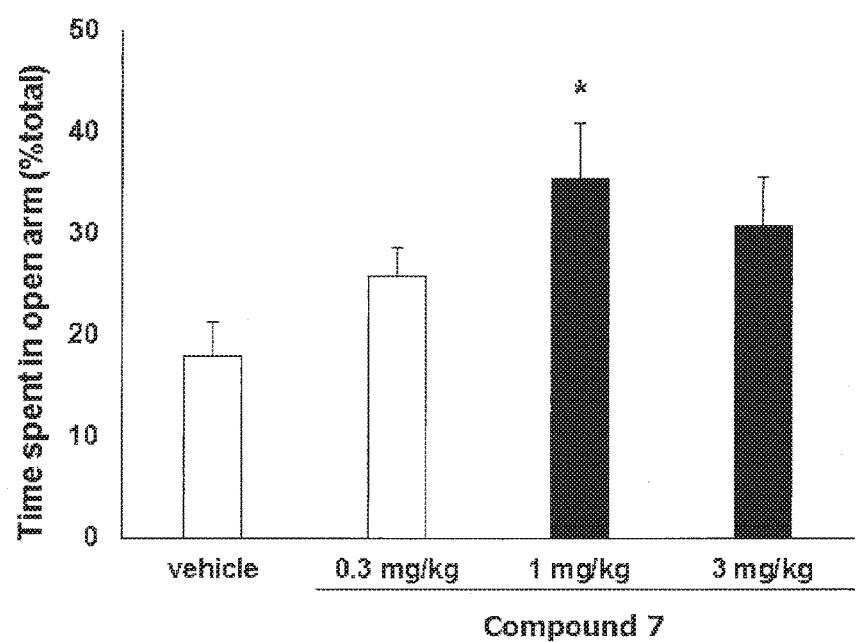

[Figure 3.]
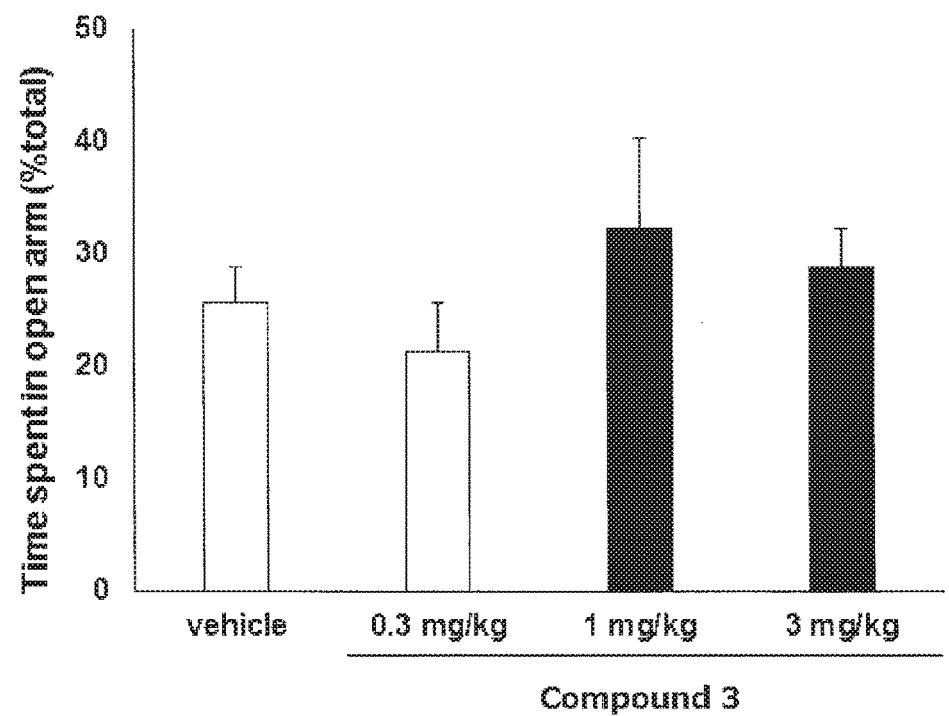
mean ± S.E. (n=8~9), not significant vs. vehicle (Dunnett test)

[Figure 4.]
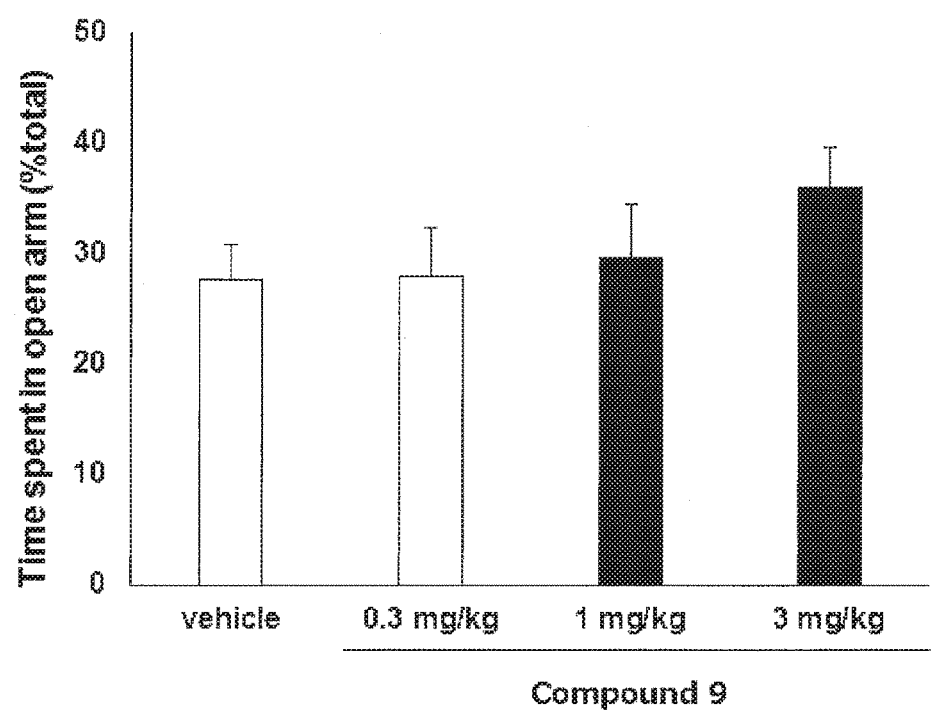
mean ± S.E. (n=9~10), not significant vs. vehicle (Dunnett test)

[Figure 5.]
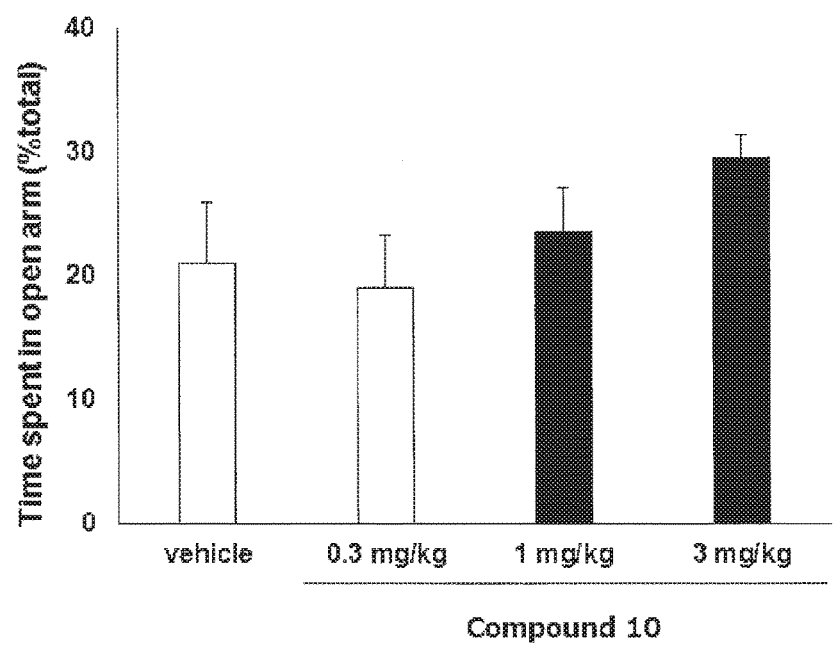
mean ± S.E. (n=8~9), not significant vs. vehicle (Dunnett test)

[Figure 6.]
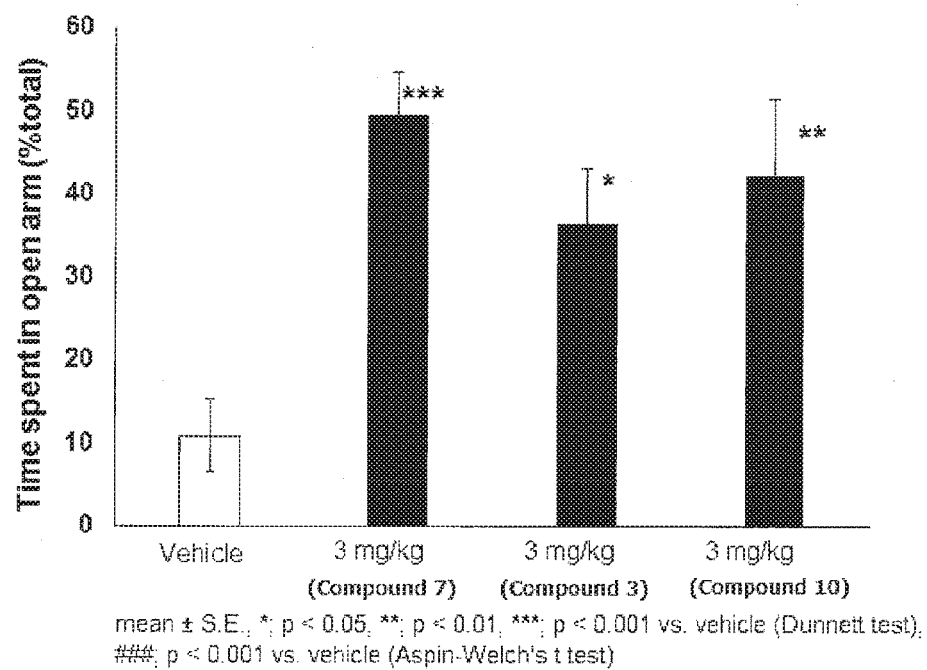

MORPHINAN DERIVATIVE

TECHNICAL FIELD

The present invention relates to a morphinan derivative having an opioid δ receptor agonistic activity.

BACKGROUND ART

Opioids bind to opioid receptors to exhibit the effect thereof, and there are three kinds of subtypes of the opioid receptors, i.e., μ, δ, and κ receptors. It is known that agonists of each of the three subtypes. i.e., μ, δ, and κ, have analgesic effects.

However, although morphine, an agonist of the opioid μ receptor showing a high affinity to the receptor, has a potent analgesic effect, it also shows adverse effects such as dependence, drug abuse, tolerance, respiratory depression, constipation caused by suppression of gastrointestinal motility, nausea and vomiting, blood pressure reductions, bradycardia, cough reflex inhibition, and sleepiness.

Although eptazocine, a selective agonist of the opioid κ receptor, has a potent analgesic effect, and shows mild dependence, tolerance, sleepiness, constipation, and respiratory depression, it causes sweating, nausea and vomiting, and thirst.

It is also known that activation of the opioid δ receptor provides analgesic, antidepressive, and anxiolytic effects. For example, it is known that enkephalin, an endogenous ligand of the opioid δ receptor, has an analgesic effect. There are also known that anxiety-like behaviors and depression-like behaviors increase in opioid δ receptor-deficient mice (Non-patent document 1), and enhancement of the enkephalin-δ receptor system is related to emotion regulation (Non-patent document 2). Further, since the antidepressive and anxiolytic-like-effects of various δ receptor agonists are antagonized by a δ receptor antagonist in various rat and mouse anxiety and depression models, usefulness of δ receptor-selective agonists as antidepressive and anxiolytic drugs have been demonstrated (Non-patent documents 3 to 7, Patent documents 1 and 2). It is expected that an agonist that selectively activates the opioid δ receptor does not show or scarcely shows adverse effects that are induced through activation of the opioid μ receptor or opioid κ receptor.

In addition, it is suggested that activation of the δ receptor shows effects for improving neurodegenerative diseases such as Parkinson's disease and Alzheimer's disease, ischaemia or cerebral stroke, urinary dysfunction, HIV infection, alcohol dependence, diabetes, and the like (Non-patent document 8). Various compounds have so far been reported as opioid δ agonists, and analgesic effects, antidepressive effects, and anxiolytic effects thereof have been verified (Patent documents 1 to 6, Non-patent document 9). It has also been reported that some opioid δ agonists such as SNC80 and BW373U86 induce convulsion (Non-patent documents 5, 6, and 10).

As antidepressants, tetracyclic antidepressants and triazolopyridine type antidepressants have been developed in addition to the classic tricyclic antidepressants and monoamine oxidase inhibitors, and in recent years, selective serotonin reuptake inhibitors (SSRI), serotonin-noradrenaline reuptake inhibitors (SNRI), and noradrenergic and specific serotonergic antidepressants (NaSSA) are frequently used. However, effectiveness of all these antidepressants is not so high as evaluated in terms of remission rate. Usefulness thereof is also limitative, because of early development of increased aggression after start of administration, risk of suicidal ideation and suicide attempt of youth age patients, and the like.

As anxiolytic drugs, although benzodiazepine type drugs are widely used, this type of drugs have outstanding problems, for example, difficulty in use for elderly people and patients showing a bad general state, because of adverse effects of them such as dependence, hypnotic action, muscle relaxation, sedation, and cognitive function decline at regular dose. Although indications of SSRI and SNRI developed as antidepressants are recently expanded to various anxiety disorders, they do not show immediate effects, and also show adverse effects. Although anesthetic drugs such as barbiturate also show anxiolytic effects, effective dose and fatal dose thereof are close to each other, and therefore they are drugs having risks.

Therefore, it is desired to develop an anxiolytic and an antidepressant that show effects thereof through a mechanism different from those of the presently used drugs, and show improved adverse effects and safety.

PRIOR ART REFERENCES

Patent Documents

Patent document 1: Japanese Patent Unexamined Publication (Kohyo) No. 2006-522775
Patent document 2: WO2001/046192
Patent document 3: WO2008/001859
Patent document 4: WO2013/035833
Patent document 5: WO2014/021273
Patent document 6: WO2014/136305

Non-Patent Documents

Non-patent document 1: Nature Genetics, 2000, 25, 195
Non-patent document 2: Neuroscience, 2005, 135, 305
Non-patent document 3: J. Pharmacol. Exp. Ther., 2011, 338, 195
Non-patent document 4: Trends in Neurosciences, 2013, 36, 195
Non-patent document 5: Behavioral Brain Research, 2011, 223, 271
Non-patent document 6: Neuropharmacology, 2013, 67, 485
Non-patent document 7: Current Neuropharmacology, 2012, 10, 231
Non-patent document 8: Psychopharmacology (Berl), 2013, 228, 1
Non-patent document 9: Tetrahedron, 2011, 67, 6682
Non-patent document 10: The International Narcotics Research Conference 2014, Jul. 13, 2014

SUMMARY OF THE INVENTION

Problem to be Solved by the Invention

An object of the present invention is to provide an anxiolytic, an antidepressant, an analgesic drug, a therapeutic agent for Parkinson's disease, and a therapeutic agent for pollakiuria and urinary incontinence that are highly effective, show less adverse effects such as dependence, tolerance, respiratory depression, constipation, nausea and vomiting, blood pressure reductions, bradycardia, cough reflex inhibition, hypnotic effects, muscle relaxation, sedation, cognitive function decline, sweating, and thirst, and are safe. Another object of the present invention is to provide a safe medicament that can even simultaneously exhibit antidepressive, anxiolytic, and analgesic effects, and thereby provide good news to patients suffered from depression, anxiety, and pain. A further object of the present invention is to provide a medicament that can be used for simultaneously treating depression, anxiety, and pain as single medicament, and that can be safe and administered orally or by injection (for example, subcutaneous injection).

Means for Solving the Problem (1) The present invention relates to a compound represented by the following general formula (I):

[Formula 2]

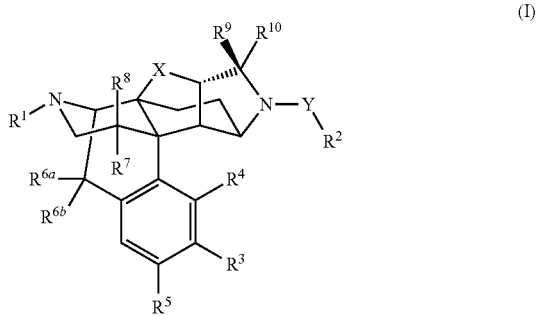

(I)

(wherein $R^1$ represents hydrogen; $C_{1-10}$ alkyl; $C_{1-10}$ aryl; $C_{2-6}$ alkenyl; cycloalkylalkyl where the cycloalkyl moiety has 3 to 6 carbon atoms, and the alkylene moiety has 1 to 5 carbon atoms; aralkyl where the aryl moiety has 6 to 10 carbon atoms, and the alkylene moiety has 1 to 5 carbon atoms; $C_{3-6}$ cycloalkyl; or heteroarylalkyl where the heteroaryl moiety contains 1 to 4 heteroatoms selected from N, O and S as ring-constituting atoms, and the alkylene moiety has 1 to 5 carbon atoms, $R^2$ represents heterocyclic ring containing 1 to 4 heteroatoms selected from N, O and S and at least one carbon atom as ring-constituting atoms, containing at least one set of adjacent ring-constituting atoms bound by a double bond, and further substituted with at least one oxo group, $R^2$ binds to Y via a carbon atom as a ring-constituting atom of $R^2$.

$R^3$, $R^4$, and $R^5$, which are the same or different, represent hydrogen; hydroxy; halogen; cyano; carbamoyl; $C_{1-6}$ alkoxy; $C_{6-10}$ aryloxy; $C_{1-6}$ alkanoyloxy; nitro; amino; $C_{1-8}$ alkylamino; $C_{6-10}$ arylamino; or acylamino where the acyl moiety has 2 to 6 carbon atoms, $R^{6a}$ and $R^{6b}$, which are the same or different, represent hydrogen; fluorine; or hydroxy, or $R^{6a}$ and $R^{6b}$ combine together to represent =O, $R^7$ and $R^8$, which are the same or different, represent hydrogen; fluorine; or hydroxy, $R^9$ and $R^{10}$, which are the same or different, represent hydrogen; $C_{1-6}$ alkyl; $C_{6-10}$ aryl; heteroaryl containing 1 to 4 heteroatoms selected from N, O and S as ring-constituting atoms; aralkyl where the aryl moiety has 6 to 10 carbon atoms, and the alkylene moiety has 1 to 5 carbon atoms; heteroarylalkyl where the heteroaryl moiety contains 1 to 4 heteroatoms selected from N, O and S as ring-constituting atoms, and the alkylene moiety has 1 to 5 carbon atoms; cycloalkylalkyl where the cycloalkyl moiety has 3 to 6 carbon atoms, and the alkylene moiety has 1 to 5 carbon atoms; or $C_{2-6}$ alkenyl, X represents O or $CH_2$, and Y represents C(=O), provided that the $C_{1-10}$ alkyl as $R^1$; the alkylene moiety and cycloalkyl moiety of the cycloalkylalkyl where the cycloalkyl moiety has 3 to 6 carbon atoms, and the alkylene moiety has 1 to 5 carbon atoms as $R^1$; the alkylene moiety of the aralkyl where the aryl moiety has 6 to 10 carbon atoms, and the alkylene moiety has 1 to 5 carbon atoms as $R^1$; and the alkylene moiety of the heteroarylalkyl where the heteroaryl moiety contains 1 to 4 heteroatoms selected from N, O and S as ring-constituting atoms, and the alkylene moiety has 1 to 5 carbon atoms as $R^1$ may be substituted with at least one substituent selected from 1 to 6 halogens; hydroxy; $C_{1-6}$ alkoxy; $C_{6-10}$ aryloxy; $C_{1-6}$ alkanoyl; $C_{1-6}$ alkanoyloxy; carboxyl; alkoxycarbonyl where the alkoxy moiety has 1 to 6 carbon atoms; carbamoyl; alkylcarbamoyl where the alkyl moiety has 1 to 6 carbon atoms; dialkylcarbamoyl where each alkyl moiety has 1 to 6 carbon atoms; alkylsulfonyl where the alkyl moiety has 1 to 6 carbon atoms; aminosulfonyl; alkylsulfinyl where the alkyl moiety has 1 to 6 carbon atoms; alkylthio where the alkyl moiety has 1 to 6 carbon atoms; $C_{1-6}$ alkoxy substituted with 1 to 6 halogens; and arylcarbonyl where the aryl moiety has 6 to 10 carbon atoms, the $C_{6-10}$ aryl as $R^1$; the aryl moiety of the aralkyl where the aryl moiety has 6 to 10 carbon atoms, and the alkylene moiety has 1 to 5 carbon atoms as $R^1$; the aryl moiety of the $C_{6-10}$ aryloxy as $R^3$, $R^4$, or $R^5$; the aryl moiety of the $C_{6-10}$ arylamino as $R^3$, $R^4$, or $R^5$; the $C_{6-10}$ aryl as $R^9$ or $R^{10}$; the heteroaryl containing 1 to 4 heteroatoms selected from N, O and S as ring-constituting atoms as $R^9$ or $R^{10}$; the aryl moiety of the aralkyl where the aryl moiety has 6 to 10 carbon atoms, and the alkylene moiety has 1 to 5 carbon atoms as $R^9$ or $R^{10}$; and the heteroaryl moiety of the heteroarylalkyl where the heteroaryl moiety contains 1 to 4 heteroatoms selected from N, O and S as ring-constituting atoms, and the alkylene moiety has 1 to 5 carbon atoms as $R^9$ or $R^{10}$ may be substituted with at least one substituent selected from $C_{1-6}$ alkyl; $C_{1-6}$ alkoxy; $C_{1-6}$ alkanoyloxy; hydroxy; alkoxycarbonyl where the alkoxy moiety has 1 to 6 carbon atoms; carbamoyl; alkylcarbamoyl where the alkyl moiety has 1 to 6 carbon atoms; dialkylcarbamoyl where each alkyl moiety has 1 to 6 carbon atoms; halogen; nitro; cyano; $C_{1-6}$ alkyl substituted with 1 to 3 halogens; $C_{1-6}$ alkoxy substituted with 1 to 3 halogens; phenyl; heteroaryl containing 1 to 4 heteroatoms selected from N, O and S as ring-constituting atoms; phenoxy; phenylalkyl where the alkyl has 1 to 3 carbon atoms; and methylenedioxy, the heterocyclic ring as $R^2$ may have, besides the oxo group, the substituents that the $C_{6-10}$ aryl as $R^1$ mentioned above may have, when $R^1$ is $C_{1-10}$ alkyl, it may be substituted with $NR^{11}R^{12}$, where $R^{11}$ and $R^{12}$, which are the same or different, represent hydrogen; $C_{1-10}$ alkyl; or aralkyl where the aryl moiety has 6 to 10 carbon atoms, and the alkylene moiety has 1 to 5 carbon atoms; or $R^{11}$, $R^{12}$, the nitrogen atom to which $R^{11}$ and $R^{12}$ bind, and optionally, 1 or 2 heteroatoms may combine together to form a 5- to 7-membered ring, and the alkylene moiety of the aralkyl where the aryl moiety has 6 to 10 carbon atoms, and the alkylene moiety has 1 to 5 carbon atoms as $R^1$ may be substituted with at least one substituent selected from phenyl, and $C_{1-6}$ alkyl substituted with 1 to 3 halogens), a tautomer or stereoisomer of the compound, or a pharmaceutically acceptable salt thereof, or a solvate thereof.

The present invention also relates to a medicament comprising a compound represented by the aforementioned general formula (I), a tautomer or stereoisomer of the compound, or a pharmaceutically acceptable salt thereof, or a solvate thereof.

The present invention also relates to a pharmaceutical composition comprising a compound represented by the aforementioned general formula (I), a tautomer or stereoisomer of the compound, or a pharmaceutically acceptable salt thereof, or a solvate thereof as an active ingredient.

The present invention also relates to an analgesic comprising a compound represented by the aforementioned general formula (I), a tautomer or stereoisomer of the compound, or a pharmaceutically acceptable salt thereof, or a solvate thereof as an active ingredient.

The present invention also relates to an antidepressant comprising a compound represented by the aforementioned general formula (I), a tautomer or stereoisomer of the compound, or a pharmaceutically acceptable salt thereof, or a solvate thereof as an active ingredient.

The present invention also relates to an anxiolytic drug comprising a compound represented by the aforementioned general formula (I), a tautomer or stereoisomer of the compound, or a pharmaceutically acceptable salt thereof, or a solvate thereof as an active ingredient.

The present invention also relates to a method for ameliorating, preventing or treating depression, which comprises administering an effective amount of a compound represented by the aforementioned general formula (I), a tautomer or stereoisomer of the compound, or a pharmaceutically acceptable salt thereof, or a solvate thereof.

The present invention also relates to a method for ameliorating, preventing or treating anxiety, which comprises administering an effective amount of a compound represented by the aforementioned general formula (I), a tautomer or stereoisomer of the compound, or a pharmaceutically acceptable salt thereof, or a solvate thereof.

The present invention also relates to a method for ameliorating, preventing or treating pain, which comprises administering an effective amount of a compound represented by the aforementioned general formula (I), a tautomer or stereoisomer of the compound, or a pharmaceutically acceptable salt thereof, or a solvate thereof.

The present invention also relates to use of a compound represented by the aforementioned general formula (I), a tautomer or stereoisomer of the compound, or a pharmaceutically acceptable salt thereof, or a solvate thereof for ameliorating, preventing or treating pain, depression, or anxiety.

The present invention also relates to a method for ameliorating, preventing or treating pain, depression, or anxiety in a human, which comprises administering an effective amount of a compound represented by the aforementioned general formula (I), a tautomer or stereoisomer of the compound, or a pharmaceutically acceptable salt thereof, or a solvate thereof to the human.

The present invention also relates to a therapeutic agent for Parkinson's disease comprising a compound represented by the aforementioned general formula (I), a tautomer or stereoisomer of the compound, or a pharmaceutically acceptable salt thereof, or a solvate thereof as an active ingredient.

The present invention also relates to a method for ameliorating, preventing or treating Parkinson's disease, which comprises administering an effective amount of a compound represented by the aforementioned general formula (I), a tautomer or stereoisomer of the compound, or a pharmaceutically acceptable salt thereof, or a solvate thereof.

The present invention also relates to use of a compound represented by the aforementioned general formula (I), a tautomer or stereoisomer of the compound, or a pharmaceutically acceptable salt thereof, or a solvate thereof for ameliorating, preventing or treating Parkinson's disease.

The present invention also relates to a method for ameliorating, preventing or treating Parkinson's disease in a human, which comprises administering an effective amount of a compound represented by the aforementioned general formula (I), a tautomer or stereoisomer of the compound, or a pharmaceutically acceptable salt thereof, or a solvate thereof to the human.

The present invention also relates to a therapeutic agent for pollakiuria or urinary incontinence comprising a compound represented by the aforementioned general formula (I), a tautomer or stereoisomer of the compound, or a pharmaceutically acceptable salt thereof, or a solvate thereof as an active ingredient.

The present invention also relates to a method for ameliorating, preventing or treating pollakiuria or urinary incontinence, which comprises administering an effective amount of a compound represented by the aforementioned general formula (I), a tautomer or stereoisomer of the compound, or a pharmaceutically acceptable salt thereof, or a solvate thereof.

The present invention also relates to use of a compound represented by the aforementioned general formula (I), a tautomer or stereoisomer of the compound, or a pharmaceutically acceptable salt thereof, or a solvate thereof for ameliorating, preventing or treating pollakiuria or urinary incontinence.

The present invention also relates to a method for ameliorating, preventing or treating pollakiuria or urinary incontinence in a human, which comprises administering an effective amount of a compound represented by the aforementioned general formula (I), a tautomer or stereoisomer of the compound, or a pharmaceutically acceptable salt thereof, or a solvate thereof to the human.

The present invention also relates to a therapeutic agent for glaucoma comprising a compound represented by the aforementioned general formula (I), a tautomer or stereoisomer of the compound, or a pharmaceutically acceptable salt thereof, or a solvate thereof as an active ingredient.

The present invention also relates to a method for ameliorating, preventing or treating glaucoma, which comprises administering an effective amount of a compound represented by the aforementioned general formula (I), a tautomer or stereoisomer of the compound, or a pharmaceutically acceptable salt thereof, or a solvate thereof.

The present invention also relates to use of a compound represented by the aforementioned general formula (I), a tautomer or stereoisomer of the compound, or a pharmaceutically acceptable salt thereof, or a solvate thereof for ameliorating, preventing or treating glaucoma.

The present invention also relates to a method for ameliorating, preventing or treating glaucoma in a human, which comprises administering an effective amount of a compound represented by the aforementioned general formula (I), a tautomer or stereoisomer of the compound, or a pharmaceutically acceptable salt thereof, or a solvate thereof to the human.

Effect of the Invention

The compounds represented by the general formula (I), tautomers or stereoisomers of the compounds, pharmaceutically acceptable salts thereof, and solvates thereof, which are the compounds provided by the present invention, exhibit potent agonistic activity for the opioid δ receptor, but do not activate or only extremely weakly activate the μ and κ receptors, and therefore they have superior antidepressive effects, anxiolytic effects, analgesic effects, therapeutic effects for Parkinson's disease, and therapeutic effects for pollakiuria and urinary incontinence based on activation of the opioid δ receptor. Since the compounds of the present invention do not activate or only extremely weakly activate the μ and κ receptors, they do not provide or extremely weakly provide adverse effects such as dependence, drug abuse, tolerance, respiratory depression, constipation caused by suppression of gastrointestinal motility, nausea and vomiting, blood pressure reductions, bradycardia, cough reflex inhibition, sleepiness, sweating, and thirst. As far as the inventors of the present invention examined, the compounds of the present invention do not act on or extremely weakly act on other receptors, channels, and enzymes. Therefore, it is expected that the compounds of the present invention do not show at all or extremely weakly show adverse effects such as convulsion, muscle relaxation, sedation, and cognitive function decline.

Since high blood concentration and enhanced migration into the brain of the compounds of the present invention are achieved by oral administration or administration by injection (for example, subcutaneous injection), they can be used by oral administration or administration by injection.

Since the compounds of the present invention are hardly metabolized in the microsomes derived from hepatocytes, they are advantageous from the viewpoint of drug metabolism. They impose little risk of adverse effects caused by metabolic products, either.

The compounds of the present invention do not show at all any inhibitory activity against Kv11.1 (or hERG, human ether-a-go-go related gene), which is the potassium ion channel responsible to the repolarization of myocardial action potential, or show such an inhibitory activity at an ignorable level, and therefore they are safe drugs in respect of risk of sudden death caused by prolongation of the QT interval.

The compounds of the present invention are highly effective and safe medicaments.

The compounds of the present invention can simultaneously eliminate all of depression, anxiety, and pain as a single medicament.

BRIEF DESCRIPTION OF THE DRAWINGS

FIG. 1 is a graph showing the results of the mouse elevated plus maze test for the compound 1.

FIG. 2 is a graph showing the results of the mouse elevated plus maze test for the compound 7.

FIG. 3 is a graph showing the results of the mouse elevated plus maze test for the compound 3.

FIG. 4 is a graph showing the results of the mouse elevated plus maze test for the compound 9.

FIG. 5 is a graph showing the results of the mouse elevated plus maze test for the compound 10.

FIG. 6 is a graph showing the results of the rat elevated plus maze test for the compounds 3, 7, and 10.

MODES FOR CARRYING OUT THE INVENTION

Hereafter, the present invention will be explained in more detail.

Preferred embodiments of the compound represented by the aforementioned general formula (I), a tautomer or stereoisomer of the compound, or a pharmaceutically acceptable salt thereof, or a solvate thereof according to (1) include the followings.

(2) The compound represented by the aforementioned general formula (T), a tautomer or stereoisomer of the compound, or a pharmaceutically acceptable salt thereof, or a solvate thereof according to (1), wherein $R^1$ is $C_{1-10}$ alkyl; cycloalkylalkyl where the cycloalkyl moiety has 3 to 6 carbon atoms, and the alkylene moiety has 1 to 5 carbon atoms; or aralkyl where the aryl moiety has 6 to 10 carbon atoms, and the alkylene moiety has 1 to 5 carbon atoms.

(3) The compound, a tautomer or stereoisomer of the compound, or a pharmaceutically acceptable salt thereof, or a solvate thereof according to (1) or (2) mentioned above, wherein $R^1$ is cycloalkylalkyl where the cycloalkyl moiety has 3 to 6 carbon atoms, and the alkylene moiety has 1 to 5 carbon atoms.

(4) The compound represented by the aforementioned general formula (I), a tautomer or stereoisomer of the compound, or a pharmaceutically acceptable salt thereof, or a solvate thereof according to (1), wherein $R^1$ is $C_{2-6}$ alkyl substituted with hydroxy; $C_{1-6}$ alkyl substituted with 1 to 6 halogens; or $C_{2-6}$ alkyl substituted with $C_{1-6}$ alkoxy.

(5) The compound represented by the aforementioned general formula (I), a tautomer or stereoisomer of the compound, or a pharmaceutically acceptable salt thereof, or a solvate thereof according to (1), wherein $R^1$ is allyl, fluoropropyl, 2-(pyridin-3-yl)ethyl, 2-(methylsulfonyl)ethyl, or 2-(aminosulfonyl)ethyl.

(6) The compound, a tautomer or stereoisomer of the compound, or a pharmaceutically acceptable salt thereof, or a solvate thereof, wherein according to any one of (1) to (5) mentioned above, wherein $R^2$ is a 5- to 7-membered heterocyclic ring containing 1 to 4 heteroatoms selected from N, O and S and at least one carbon atom as ring-constituting atoms, containing at least one set of adjacent ring-constituting atoms bound by a double bond, and further substituted with at least one oxo group; or a heterocyclic ring consisting of the foregoing heterocyclic ring and a benzene ring condensed thereto.

(7) The compound, a tautomer or stereoisomer of the compound, or a pharmaceutically acceptable salt thereof, or a solvate thereof according to any one of (1) to (6) mentioned above, wherein $R^2$ is pyridine 1-oxide, which may be substituted with 1 to 4 substituents selected from $C_{1-10}$ alkyl substituted with 1 to 3 fluorine atoms, and unsubstituted $C_{1-10}$ alkyl.

(8) The compound, a tautomer or stereoisomer of the compound, or a pharmaceutically acceptable salt thereof, or a solvate thereof according to any one of (1) to (7) mentioned above, wherein $R^2$ is pyridine 1-oxide.

(9) The compound, a tautomer or stereoisomer of the compound, or a pharmaceutically acceptable salt thereof, or a solvate thereof according to any one of (1) to (6) mentioned above, wherein $R^2$ is pyridin-2(1H)-one, which may be substituted with 1 to 4 substituents selected from $C_{1-10}$ alkyl substituted with 1 to 3 fluorine atoms, and unsubstituted $C_{1-10}$ alkyl.

(10) The compound, a tautomer or stereoisomer of the compound, or a pharmaceutically acceptable salt thereof, or a solvate thereof according to any one of (1) to (6), and (9) mentioned above, wherein $R^2$ is pyridin-2(1H)-one; 1-($C_{1-6}$ alkyl)pyridin-2(1H)-one; or 6-($C_{1-6}$ alkyl)pyridin-2(1H)-one.

(11) The compound, a tautomer or stereoisomer of the compound, or a pharmaceutically acceptable salt thereof, or a solvate thereof according to any one of (1) to (6) mentioned above, wherein $R^2$ is pyridin-4(1H)-one, which may be substituted with 1 to 4 substituents selected from $C_{1-10}$ alkyl substituted with 1 to 3 fluorine atoms, and unsubstituted $C_{1-10}$ alkyl.

(12) The compound, a tautomer or stereoisomer of the compound, or a pharmaceutically acceptable salt thereof, or a solvate thereof according to any one of (1) to (6), and (11) mentioned above, wherein $R^2$ is pyridin-4(1H)-one, or 1-($C_{1-6}$ alkyl)pyridin-4(1H)-one.

(13) The compound, a tautomer or stereoisomer of the compound, or a pharmaceutically acceptable salt thereof, or a solvate thereof according to any one of (1) to (6) mentioned above, wherein $R^2$ is pyridazin-3(2H)-one, which may be substituted with 1 to 3 substituents selected from $C_{1-10}$ alkyl substituted with 1 to 3 fluorine atoms, and unsubstituted $C_{1-10}$ alkyl.

(14) The compound, a tautomer or stereoisomer of the compound, or a pharmaceutically acceptable salt thereof, or a solvate thereof according to any one of (1) to (6), and (13) mentioned above, wherein $R^2$ is pyridazin-3(2H)-one.

(15) The compound, a tautomer or stereoisomer of the compound, or a pharmaceutically acceptable salt thereof, or a solvate thereof according to any one of (1) to (6) mentioned above, wherein $R^2$ is pyrazin-2(1H)-one, which may be substituted with 1 to 3 substituents selected from $C_{1-10}$ alkyl substituted with 1 to 3 fluorine atoms, and unsubstituted $C_{1-10}$ alkyl.

(16) The compound, a tautomer or stereoisomer of the compound, or a pharmaceutically acceptable salt thereof, or a solvate thereof according to any one of (1) to (6) mentioned above, wherein $R^2$ is pyrazin-2(1H)-one.

(17) The compound, a tautomer or stereoisomer of the compound, or a pharmaceutically acceptable salt thereof, or a solvate thereof according to any one of (1) to (6) mentioned above, wherein $R^2$ is 4H-pyran-4-one, or 2H-pyran-2-one, which may be substituted with 1 to 3 substituents selected from $C_{1-10}$ alkyl substituted with 1 to 3 fluorine atoms, and unsubstituted $C_{1-10}$ alkyl.

(18) The compound, a tautomer or stereoisomer of the compound, or a pharmaceutically acceptable salt thereof, or a solvate thereof according to any one of (1) to (6), and (17) mentioned above, wherein $R^2$ is 4H-pyran-4-one, or 2H-pyran-2-one.

(19) The compound, a tautomer or stereoisomer of the compound, or a pharmaceutically acceptable salt thereof, or a solvate thereof according to any one of (1) to (6) mentioned above, wherein $R^2$ is quinolin-2(1H)-one, which may be substituted with 1 to 3 substituents selected from $C_{1-10}$ alkyl substituted with 1 to 3 fluorine atoms, and unsubstituted $C_{1-10}$ alkyl.

(20) The compound, a tautomer or stereoisomer of the compound, or a pharmaceutically acceptable salt thereof, or a solvate thereof according to any one of (1) to (6) mentioned above, wherein $R^2$ is quinolin-2(1H)-one.

(21) The compound, a tautomer or stereoisomer of the compound, or a pharmaceutically acceptable salt thereof, or a solvate thereof according to any one of (1) to (6) mentioned above, wherein $R^2$ is pyrimidin-4(3H)-one, or pyrimidine-2,4(1H,3H)-dione, which may be substituted with 1 to 3 substituents selected from $C_{1-10}$ alkyl substituted with 1 to 3 fluorine atoms, and unsubstituted $C_{1-10}$ alkyl.

(22) The compound, a tautomer or stereoisomer of the compound, or a pharmaceutically acceptable salt thereof, or a solvate thereof according to any one of (1) to (6), and (21) mentioned above, wherein $R^2$ is pyrimidin-4(3H)-one, or pyrimidine-2,4(1H,3H)-dione.

(23) The compound, a tautomer or stereoisomer of the compound, or a pharmaceutically acceptable salt thereof, or a solvate thereof according to any one of (1) to (22) mentioned above, wherein X is $CH_2$.

(24) The compound, a tautomer or stereoisomer of the compound, or a pharmaceutically acceptable salt thereof, or a solvate thereof according to any one of (1) to (23) mentioned above, wherein one of $R^3$ and $R^4$ is hydroxy, and the other is hydrogen.

(25) The compound, a tautomer or stereoisomer of the compound, or a pharmaceutically acceptable salt thereof, or a solvate thereof according to any one of (1) to (23) mentioned above, wherein $R^3$ is halogen; cyano; carbamoyl; $C_{1-6}$ alkoxy; $C_{1-6}$ alkanoyloxy; amino; or acylamino where the acyl moiety has 2 to 6 carbon atoms, $R^4$ is hydrogen or hydroxy, and $R^5$ is hydrogen.

(26) The compound, a tautomer or stereoisomer of the compound, or a pharmaceutically acceptable salt thereof, or a solvate thereof according to any one of (1) to (23) mentioned above, wherein $R^3$ is hydroxy; carbamoyl; or $C_{1-6}$ s alkanoyloxy, $R^4$ is hydrogen, and $R^5$ is hydrogen.

(27) The compound, a tautomer or stereoisomer of the compound, or a pharmaceutically acceptable salt thereof, or a solvate thereof according to any one of (1) to (23) mentioned above, wherein $R^3$ is hydroxy, $R^4$ is hydrogen, and $R^5$ is hydrogen.

(28) The compound, a tautomer or stereoisomer of the compound, or a pharmaceutically acceptable salt thereof, or a solvate thereof according to any one of (1) to (23) mentioned above, wherein all of $R^3$, $R^4$, and $R^5$ are hydrogens.

(29) The compound, a tautomer or stereoisomer of the compound, or a pharmaceutically acceptable salt thereof, or a solvate thereof according to any one of (1) to (28) mentioned above, wherein all of $R^{6a}$, $R^{6b}$, $R^7$, $R^8$, $R^9$, and $R^{10}$ are hydrogens.

(30) The compound represented by the aforementioned general formula (I), a tautomer or stereoisomer of the compound, or a pharmaceutically acceptable salt thereof, or a solvate thereof according to (1), wherein:

$R^5$, $R^{6a}$, $R^{6b}$, $R^7$, $R^8$, $R^9$, and $R^{10}$ are hydrogens, $R^1$ is hydrogen; $C_{1-6}$ alkyl; $C_{2-6}$ alkenyl; cycloalkylalkyl where the cycloalkyl moiety has 3 to 6 carbon atoms, and the alkylene moiety has 1 to 5 carbon atoms; or aralkyl where the aryl moiety has 6 to 10 carbon atoms, and the alkylene moiety has 1 to 5 carbon atoms, $R^2$ is a 5- to 7-membered heterocyclic ring containing 1 to 4 heteroatoms selected from N, O and S and at least one carbon atom as ring-constituting atoms, containing at least one set of adjacent ring-constituting atoms bound by a double bond, and further substituted with at least one oxo group, or a heterocyclic ring consisting of the foregoing heterocyclic ring and a benzene ring condensed thereto, $R^2$ binds to Y via a carbon atom of $R^2$ as a ring-constituting atom, $R^3$ and $R^4$, which are the same or different, represent hydrogen; hydroxy; halogen; cyano; carbamoyl; $C_{1-6}$ alkoxy; $C_{6-10}$ aryloxy; $C_{1-6}$ alkanoyloxy; amino; or acylamino where the acyl moiety has 2 to 6 carbon atoms, X is $CH_2$, and Y is C(=O), provided that the $C_{1-6}$ alkyl as $R^1$; the alkylene moiety and cycloalkyl moiety of the cycloalkylalkyl where the cycloalkyl moiety has 3 to 6 carbon atoms, and the alkylene moiety has 1 to 5 carbon atoms as $R^1$; and the alkylene moiety of the aralkyl where the aryl moiety has 6 to 10 carbon atoms, and the alkylene moiety has 1 to 5 carbon atoms as $R^1$ may be substituted with at least one substituent selected from 1 to 6 halogens; hydroxy; $C_{1-6}$ alkoxy; $C_{6-10}$ aryloxy; $C_{1-6}$ alkanoyl; $C_{1-6}$ alkanoyloxy; carboxyl; alkoxycarbonyl where the alkoxy moiety has 1 to 6 carbon atoms; carbamoyl; alkylcarbamoyl where the alkyl moiety has 1 to 6 carbon atoms; dialkylcarbamoyl where each alkyl moiety has 1 to 6 carbon atoms; alkylsulfonyl where the alkyl moiety has 1 to 6 carbon atoms; aminosulfonyl; alkylsulfinyl where the alkyl moiety has 1 to 6 carbon atoms; alkylthio where the alkyl moiety has 1 to 6 carbon atoms; $C_{1-6}$ alkoxy substituted with 1 to 6 halogens; and arylcarbonyl where the aryl moiety has 6 to 10 carbon atoms, the aryl moiety of the aralkyl where the aryl moiety has 6 to 10 carbon atoms, and the alkylene moiety has 1 to 5 carbon atoms as $R^1$; and the aryl moiety of the $C_{6-10}$ aryloxy as $R^3$ or $R^4$ may be substituted with at least one substituent selected from $C_{1-6}$ alkyl; $C_{1-6}$ alkoxy; $C_{1-6}$ alkanoyloxy; hydroxy; alkoxycarbonyl where the alkoxy moiety has 1 to 6 carbon atoms; carbamoyl; alkylcarbamoyl where the alkyl moiety has 1 to 6 carbon atoms; dialkylcarbamoyl where each alkyl moiety has 1 to 6 carbon atoms; halogen; nitro; cyano; $C_{1-6}$ alkyl substituted with 1 to 3 halogens; $C_{1-6}$ alkoxy substituted with 1 to 3 halogens; phenyl; heteroaryl containing 1 to 4 heteroatoms selected from N, O and S as ring-constituting atoms; phenoxy; phenylalkyl where the alkyl has 1 to 3 carbon atoms; and methylenedioxy, the heterocyclic ring as $R^2$ may have, besides the oxo group, at least one of the substituents which the aryl moiety of the aralkyl where the aryl moiety has 6 to 10 carbon atoms, and the alkylene moiety has 1 to 5 carbon atoms as $R^1$ may have, and the alkylene moiety of the aralkyl where the aryl moiety has 6 to 10 carbon atoms, and the alkylene moiety has 1 to 5 carbon atoms as $R^1$ may be substituted with at least one substituent selected from phenyl, and $C_{1-6}$ alkyl substituted with 1 to 3 halogens.

(31) The compound, a tautomer or stereoisomer of the compound, or a pharmaceutically acceptable salt thereof, or a solvate thereof according to (1) or (30), wherein $R^1$ is $C_{1-6}$ alkyl; cycloalkylalkyl where the cycloalkyl moiety is 3 to 6 carbon atoms, and the alkylene moiety has 1 to 5 carbon atoms; or aralkyl where the aryl moiety has 6 to 10 carbon atoms, and the alkylene moiety has 1 to 5 carbon atoms.

(32) The compound, a tautomer or stereoisomer of the compound, or a pharmaceutically acceptable salt thereof, or a solvate thereof according to (1), (30), or (31), wherein $R^1$ is cycloalkylalkyl where the cycloalkyl moiety has 3 to 6 carbon atoms, and the alkylene moiety has 1 to 5 carbon atoms.

(33) The compound, a tautomer or stereoisomer of the compound, or a pharmaceutically acceptable salt thereof, or a solvate thereof according to (1) or (30), wherein $R^1$ is $C_{2-6}$ alkyl substituted with hydroxy; $C_{1-6}$ alkyl substituted with 1 to 6 halogens; or $C_{2-6}$ alkyl substituted with $C_{1-6}$ alkoxy.

(34) The compound, a tautomer or stereoisomer of the compound, or a pharmaceutically acceptable salt thereof, or a solvate thereof according to (1) or (30), wherein $R^1$ is allyl, fluoropropyl, 2-(pyridin-3-yl)ethyl, 2-(methylsulfonyl)ethyl, or 2-(aminosulfonyl)ethyl.

(35) The compound, a tautomer or stereoisomer of the compound, or a pharmaceutically acceptable salt thereof, or a solvate thereof according to any one of (1), and (30) to (34), wherein $R^2$ is pyridine 1-oxide, pyridin-2(1H)-one, pyridin-4(1H)-one, pyridazin-3(2H)-one, pyrazin-2(1H)-one, 4H-pyran-4-one, 2H-pyran-2-one, quinolin-2(1H)-one, pyrimidin-4(3H)-one, or pyrimidine-2,4(1H,3H)-dione, which may be substituted with a substituent selected from $C_{1-10}$ alkyl substituted with 1 to 3 fluorine atoms, and unsubstituted $C_{1-10}$ alkyl.

(36) The compound, a tautomer or stereoisomer of the compound, or a pharmaceutically acceptable salt thereof, or a solvate thereof according to any one of (1), and (30) to (35), wherein $R^2$ is pyridine 1-oxide, which may be substituted with 1 to 4 substituents selected from $C_{1-10}$ alkyl substituted with 1 to 3 fluorine atoms, and unsubstituted $C_{1-10}$ alkyl.

(37) The compound, a tautomer or stereoisomer of the compound, or a pharmaceutically acceptable salt thereof, or a solvate thereof according to any one of (1), and (30) to (36), wherein $R^2$ is pyridine 1-oxide.

(38) The compound, a tautomer or stereoisomer of the compound, or a pharmaceutically acceptable salt thereof, or a solvate thereof according to any one of (1), and (30) to (35), wherein $R^2$ is pyridin-2(1H)-one, which may be substituted with 1 to 4 substituents selected from $C_{1-10}$ alkyl substituted with 1 to 3 fluorine atoms, and unsubstituted $C_{1-10}$ alkyl.

(39) The compound, a tautomer or stereoisomer of the compound, or a pharmaceutically acceptable salt thereof, or a solvate thereof according to any one of (1), and (30) to (35), wherein $R^2$ is pyridin-2(1H)-one; 1-($C_{1-6}$ alkyl)pyridin-2(1H)-one; or 6-($C_{1-6}$ alky)pyridin-2(1H)-one.

(40) The compound, a tautomer or stereoisomer of the compound, or a pharmaceutically acceptable salt thereof, or a solvate thereof according to any one of (1), and (30) to (35), wherein $R^2$ is pyridin-4(1H)-one, which may be substituted with 1 to 4 substituents selected from $C_{1-10}$ alkyl substituted with 1 to 3 fluorine atoms, and unsubstituted $C_{1-10}$ alkyl.

(41) The compound, a tautomer or stereoisomer of the compound, or a pharmaceutically acceptable salt thereof, or a solvate thereof according to any one of (1), (30) to (35), and (40), wherein $R^2$ is pyridin-4(1H)-one, or 1-($C_{1-6}$ alkyl)pyridin-4(1H)-one.

(42) The compound, a tautomer or stereoisomer of the compound, or a pharmaceutically acceptable salt thereof, or a solvate thereof according to any one of (1), and (30) to (35), wherein $R^2$ is pyridazin-3(2H)-one, which may be substituted with 1 to 3 substituents selected from $C_{1-10}$ alkyl substituted with 1 to 3 fluorine atoms, and unsubstituted $C_{1-10}$ alkyl.

(43) The compound, a tautomer or stereoisomer of the compound, or a pharmaceutically acceptable salt thereof, or a solvate thereof according to any one of (1), (30) to (35), and (42), wherein $R^2$ is pyridazin-3(2H)-one.

(44) The compound, a tautomer or stereoisomer of the compound, or a pharmaceutically acceptable salt thereof, or a solvate thereof according to any one of (1), and (30) to (35), wherein $R^2$ is pyrazin-2(1H)-one, which may be substituted with 1 to 3 substituents selected from $C_{1-10}$ alkyl substituted with 1 to 3 fluorine atoms, and unsubstituted $C_{1-10}$ alkyl.

(45) The compound, a tautomer or stereoisomer of the compound, or a pharmaceutically acceptable salt thereof, or a solvate thereof according to any one of (1), (30) to (35), and (44), wherein $R^2$ is pyrazin-2(1H)-one.

(46) The compound, a tautomer or stereoisomer of the compound, or a pharmaceutically acceptable salt thereof, or a solvate thereof according to any one of (1), and (30) to (35), wherein $R^2$ is 4H-pyran-4-one, or 2H-pyran-2-one, which may be substituted with 1 to 3 substituents selected from $C_{1-10}$ alkyl substituted with 1 to 3 fluorine atoms, and unsubstituted $C_{1-10}$ alkyl.

(47) The compound, a tautomer or stereoisomer of the compound, or a pharmaceutically acceptable salt thereof, or a solvate thereof according to any one of (1), (30) to (35), and (46), wherein $R^2$ is 4H-pyran-4-one, or 2H-pyran-2-one.

(48) The compound, a tautomer or stereoisomer of the compound, or a pharmaceutically acceptable salt thereof, or a solvate thereof according to any one of (1), and (30) to (35), wherein $R^2$ is quinolin-2(1H)-one, which may be substituted with 1 to 3 substituents selected from $C_{1-10}$ alkyl substituted with 1 to 3 fluorine atoms, and unsubstituted $C_{1-10}$ alkyl.

(49) The compound, a tautomer or stereoisomer of the compound, or a pharmaceutically acceptable salt thereof, or a solvate thereof according to any one of (1), (30) to (35), and (48), wherein $R^2$ is quinolin-2(1H)-one.

(50) The compound, a tautomer or stereoisomer of the compound, or a pharmaceutically acceptable salt thereof, or a solvate thereof according to any one of (1), and (30) to (35), wherein $R^2$ is pyrimidin-4(3H)-one, or pyrimidine-2,4(1H,3H)-dione, which may be substituted with 1 to 3 substituents selected from $C_{1-10}$ alkyl substituted with 1 to 3 fluorine atoms, and unsubstituted $C_{1-10}$ alkyl.

(51) The compound, a tautomer or stereoisomer of the compound, or a pharmaceutically acceptable salt thereof, or a solvate thereof according to any one of (1), (30) to (35), and (50), wherein $R^2$ is pyrimidin-4(3H)-one, or pyrimidine-2,4(1H,3H)-dione.

(52) The compound, a tautomer or stereoisomer of the compound, or a pharmaceutically acceptable salt thereof, or a solvate thereof according to any one of (1), and (30) to (51), wherein one of $R^3$ and $R^4$ is hydroxy, and the other is hydrogen.

(53) The compound, a tautomer or stereoisomer of the compound, or a pharmaceutically acceptable salt thereof, or a solvate thereof according to any one of (1), and (30) to (51), wherein $R^3$ is halogen; cyano; carbamoyl; $C_{1-6}$ alkoxy; $C_{1-6}$ alkanoyloxy; amino; or acylamino where the acyl moiety has 2 to 6 carbon atoms, and $R^4$ is hydrogen or hydroxy.

(54) The compound, a tautomer or stereoisomer of the compound, or a pharmaceutically acceptable salt thereof, or a solvate thereof according to any one of (1), and (30) to (51), wherein $R^3$ is hydroxy; carbamoyl; or $C_{1-6}$ alkanoyloxy, and $R^4$ is hydrogen.

(55) The compound, a tautomer or stereoisomer of the compound, or a pharmaceutically acceptable salt thereof, or a solvate thereof according to any one of (1), and (30) to (51), wherein $R^3$ is hydroxy, and $R^4$ is hydrogen.

(56) The compound, a tautomer or stereoisomer of the compound, or a pharmaceutically acceptable salt thereof, or a solvate thereof according to any one of (1), and (30) to (51), wherein $R^3$ and $R^4$ are hydrogens.

(57) A compound selected from:

2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide, 4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide, 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one, 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide, 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one, 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one, 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one.

3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-6-methylpyridin-2(1H)-one, 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-c]indole-3-carbonyl)-1-methylpyridin-2(1H)-one, 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one, 4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one, 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrimidine-2,4(1H,3H)-dione, 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-4(1H)-one, 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-4(1H)-one, 4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one, 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridazin-3(2H)-one, 4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)quinolin-2 (1H)-one, 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-2H-pyran-2-one, 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-4H-pyran-4-one, 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-4(1H)-one, 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrazin-2(1H)-one, 2-((1S,3aR,5aS,6R,11bR,11cS)-10-acetoxy-14-(cyclopropylmethyl)-2,3,3a,4,5,6,7,11c-octahydro-1H-6,11b-(epiminoethano)-1,5a-methanonaphtho[1,2-e]indole-3-carbonyl)pyridine 1-oxide.

6-((1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indole-3-carbonyl)pyridin-2(1H)-one, 3-((1S,3aR,6aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrazin-2(1H)-one, 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrimidine-2,4(1H,3H)-dione.

6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-ethylpyridin-2(1H)-one, 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrimidin-4(3H)-one, and 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-ethylpyridin-2(1H)-one, a tautomer or stereoisomer of the compound, or a pharmaceutically acceptable salt thereof, or a solvate thereof.

(58) A compound selected from:

6-((1S,3aR,5aS,6R,11bR,11cS)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one, 4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methyl-1,2-dihydro-3H-pyrazol-3-one, 5-chloro-3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one, 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1,3-dimethylpyrimidine-2,4(1H,3H)-dione, and 6-((1S,3aR,5aS,6R,11bR,11cS)-14-(cyclopropylmethyl)-10-methoxy-2,3,3a,4,5,6,7,11c-octahydro-1H-6,11b-(epiminoethano)-1,5a-methanonaphtho[1,2-e]indole-3-carbonyl)pyridin-2(1H)-one, a tautomer or stereoisomer of the compound, or a pharmaceutically acceptable salt thereof, or a solvate thereof.

As used herein:

Examples of the $C_{1-6}$ alkyl include methyl, ethyl, propyl, i-propyl, butyl, t-butyl, pentyl, neopentyl, hexyl, and the like.

Examples of the $C_{1-10}$ alkyl include those exemplified for the $C_{1-6}$ alkyl, as well as heptyl, octyl, and the like.

Examples of the $C_{1-6}$ alkyl substituted with 1 to 3 halogens include 2-chloroethyl, 2-fluoroethyl, 3-fluoropropyl, 2,2-difluoroethyl, trifluoromethyl, 3,3,3-trifluoropropyl, and the like.

Examples of the $C_{2-6}$ alkenyl include 2-propenyl, 3-methyl-2-butenyl, and the like.

Examples of the cycloalkylalkyl where the cycloalkyl moiety has 3 to 6 carbon atoms, and the alkylene moiety has 1 to 5 carbon atoms include methyl, ethyl, and the like substituted with $C_{3-6}$ cycloalkyl such as cyclopropyl, cyclobutyl, cyclopentyl, and cyclohexyl.

Examples of the aralkyl where the aryl moiety has 6 to 10 carbon atoms, and the alkylene moiety has 1 to 5 carbon atoms include benzyl group, and phenethyl group.

Examples of the $C_{3-6}$ cycloalkyl include cyclopropyl, cyclobutyl, cyclopentyl, cyclohexyl, and the like.

Examples of the $C_{6-10}$ aryl include phenyl, naphthyl, and the like.

Examples of the heteroaryl containing 1 to 4 heteroatoms selected from N, O and S as ring-constituting atoms include pyridyl, furyl, imidazolyl, pyrazolyl, pyrimidinyl, pyrazinyl, pyridazinyl, thiazolyl, and the like.

Examples of the heteroarylalkyl where the heteroaryl moiety contains 1 to 4 heteroatoms selected from N, O and S as ring-constituting atoms, and the alkylene moiety has 1 to 5 carbon atoms include (pyridin-2-yl)methyl, (pyridin-3-yl)methyl, (pyridin-4-yl)methyl, (furan-2-yl)methyl, (furan-3-yl)methyl, (imidazol-2-yl)methyl, (imidazol-4-yl)methyl, (imidazol-5-yl)methyl, (thiazol-2-yl)methyl, (thiazol-4-yl)methyl, (thiazol-5-yl)methyl, 2-(pyridin-2-yl)ethyl, 2-(pyridin-3-yl)ethyl, 2-(pyrazol-1-yl)ethyl, 2-(thiophen-2-yl)ethyl, 2-(thiophen-3-yl)ethyl, and the like.

Examples of the $C_{1-6}$ alkanoyl include acetyl, propionyl, and the like.

Examples of the $C_{1-6}$ alkoxy include methoxy, ethoxy, propoxy, and the like.

Examples of the $C_{1-6}$ alkanoyloxy include acetoxy, and the like.

Examples of the alkoxycarbonyl where the alkoxy moiety has 1 to 6 carbon atoms include methoxycarbonyl, ethoxycarbonyl, and the like.

Examples of the halogen include fluorine, chlorine, bromine, iodine, and the like.

Examples of the $C_{1-6}$ alkoxy substituted with 1 to 3 halogens include fluoromethoxy, trifluoromethoxy, and the like.

Examples of the $C_{1-6}$ alkoxy substituted with 1 to 6 halogens include those mentioned above for the $C_{1-6}$ alkoxy substituted with 1 to 3 halogens, as well as tetrafluoroethoxy, and the like.

Examples of the phenylalkyl where the alkyl has 1 to 3 carbon atoms include benzyl, and the like.

Examples of the $C_{6-10}$ aryloxy include phenoxy, and the like.

Examples of the $C_{1-8}$ alkylamino include methylamino, ethylamino, and the like.

Examples of the acylamino where the acyl moiety has 2 to 6 carbon atoms include acetylamino, and the like.

Examples of the $C_{6-10}$ arylamino include phenylamino, and the like.

Examples of the alkylcarbamoyl where the alkyl moiety has 1 to 6 carbon atoms include ethylcarbamoyl, and the like.

Examples of the dialkylcarbamoyl where each alkyl moiety has 1 to 6 carbon atoms include diethylcarbamoyl, and the like.

Examples of the alkylsulfonyl where the alkyl moiety has 1 to 6 carbon atoms include methylsulfonyl, and the like.

Examples of the alkylsulfinyl where the alkyl moiety has 1 to 6 carbon atoms include methylsulfinyl, and the like.

Examples of the alkylthio where the alkyl moiety has 1 to 6 carbon atoms include methylthio, and the like.

Examples of the arylcarbonyl where the aryl moiety has 6 to 10 carbon atoms include benzoyl, and the like.

Examples of the 5- to 7-membered ring that may be formed by combining $R^{11}$, $R^{12}$ together with the nitrogen atom to which $R^{11}$ and $R^{12}$ bind, and optionally, 1 or 2 heteroatoms include pyrrolidine, piperidine, morpholine, and the like.

Examples of the heterocyclic ring containing 1 to 4 heteroatoms selected from N, O and S and at least one carbon atom as ring-constituting atoms, containing at least one set of adjacent ring-constituting atoms bound by a double bond, and further substituted with at least one oxo group as $R^2$ include:

(A) pyridine 1-oxide, which may be substituted with 1 to 4 substituents selected from $C_{1-10}$ alkyl substituted with 1 to 3 fluorine atoms, and unsubstituted $C_{1-10}$ alkyl: for example, pyridine 1-oxide and 2-methylpyridine 1-oxide;

(B) pyridin-2(1H)-one, which may be substituted with 1 to 4 substituents selected from $C_{1-10}$ alkyl substituted with 1 to 3 fluorine atoms, and unsubstituted $C_{1-10}$ alkyl: for example, pyridin-2(1H)-one, 1-methylpyridin-2(1H)-one, 1-ethylpyridin-2(1H)-one, 6-methylpyridin-2(1H)-one, 6-ethylpyridin-2(1H)-one, and 6-trifluoromethylpyridin-2(1H)-one;

(C) pyridin-4(1H)-one, which may be substituted with 1 to 4 substituents selected from $C_{1-10}$ alkyl substituted with 1 to 3 fluorine atoms, and unsubstituted $C_{1-10}$ alkyl: for example, pyridin-4(1H)-one, 1-methylpyridin-4(1H)-one, 1-ethylpyridin-4(1H)-one, and 1-(fluoroethyl)pyridin-4(1H)-one;

(D) pyridazin-3(2H)-one, which may be substituted with 1 to 3 substituents selected from $C_{1-10}$ alkyl substituted with 1 to 3 fluorine atoms, and unsubstituted $C_{1-10}$ alkyl: for example, pyridazin-3(2H)-one and 2-methylpyridazin-3(2H)-one;

(E) pyrazin-2(1H)-one, which may be substituted with 1 to 3 substituents selected from $C_{1-10}$ alkyl substituted with 1 to 3 fluorine atoms, and unsubstituted $C_{1-10}$ alkyl: for example, pyrazin-2(1H)-one, and 1-methylpyrazin-2(1H)-one;

(F) 4H-pyran-4-one, or 2H-pyran-2-one, which may be substituted with 1 to 3 substituents selected from $C_{1-10}$ to alkyl substituted with 1 to 3 fluorine atoms, and unsubstituted $C_{1-10}$ alkyl: for example, 4H-pyran-4-one, 3-methyl-4H-pyran-4-one, 2H-pyran-2-one, and 5-methyl-2H-pyran-2-one;

(G) quinolin-2(1H)-one, or quinoline-1-oxide, which may be substituted with 1 to 3 substituents selected from $C_{1-10}$ to alkyl substituted with 1 to 3 fluorine atoms, and unsubstituted $C_{1-10}$ alkyl: for example, quinolin-2(1H)-one, 6-methylquinolin-2(1H)-one, quinoline-1-oxide, and 4-methylquinoline-1-oxide;

(H) pyrimidin-4(3H)-one, or pyrimidine-2,4(1H,3H)-dione, which may be substituted with 1 to 3 substituents selected from $C_{1-10}$ alkyl substituted with 1 to 3 fluorine atoms, and unsubstituted $C_{1-10}$ alkyl: for example, pyrimidin-4(3H)-one, and pyrimidine-2,4(1H,3H)-dione, and the like.

Examples of tautomer of the compound represented by the aforementioned general formula (I) include tautomers for the aforementioned heterocyclic ring containing 1 to 4 heteroatoms selected from N, O and S and at least one carbon atom as ring-constituting atoms, containing at least one set of adjacent ring-constituting atoms bound by a double bond, and further substituted with at least one oxo group as $R^2$, and specifically, 2-pyridone (lactam) as $R^2$ and the corresponding 2-hydroxypyridine (lactim) can be mentioned as such an example.

As for the compound represented by the aforementioned general formula (I), a tautomer or stereoisomer of the compound, or a pharmaceutically acceptable salt thereof, or a solvate thereof, preferred examples of the pharmaceutically acceptable acid include acid addition salts, and examples of acid addition salts include salts with an inorganic acid or organic acid such as hydrochloride, sulfate, fumarate, oxalate, methanesulfonate, and camphorsulfonate.

As for the compound represented by the aforementioned general formula (I), a tautomer or stereoisomer of the compound, or a pharmaceutically acceptable salt thereof, or a solvate thereof, examples of the stereoisomer include cis- and trans-isomers, racemates, optically active compounds, and the like.

As for the compound represented by the aforementioned general formula (I), a tautomer or stereoisomer of the compound, or a pharmaceutically acceptable salt thereof, or a solvate thereof, the solvate is a pharmaceutically acceptable solvate of the compound of the present invention or a salt thereof, and includes hydrate.

The compound represented by the aforementioned general formula (I), a tautomer or stereoisomer of the compound, or a pharmaceutically acceptable salt thereof, or a solvate thereof may be chemically modified into such a prodrug that it is converted into a pharmacologically active substance and exhibits the pharmacological activity (being activated) after it is delivered into the inside of the body or a target site.

Examples of group for constituting such a prodrug include, for example, common protective groups of hydroxy group such as a lower acyl group and a lower alkoxycarbonyl group for the case where the group constituting a prodrug exists on hydroxy group, common protective groups of amino group such as a lower acyl group and a lower alkoxycarbonyl group for the case where the group constituting a prodrug exists on nitrogen atom, prodrug groups introduced into a carboxylic acid moiety such as pivaloyloxymethyl (tBu-C(O)O—$CH_2$—) group, medoxomil group, and cilexetil group, and the like.

An atom contained in the compound represented by the aforementioned general formula (I), a tautomer or stereoisomer of the compound, or a pharmaceutically acceptable salt thereof, or a solvate thereof may be replaced with a stable isotope such as deuterium.

Hereafter, methods for preparing the compound represented by the aforementioned general formula (I), a tautomer or stereoisomer of the compound, or a pharmaceutically acceptable salt thereof, or a solvate thereof will be shown below.

The abbreviations used herein are as follows.

Abbreviation Table

Boc: Tert-butoxycarbonyl
CPM: Cyclopropylmethyl
DMA: N,N-Dimethylacetamide
DMAP: N,N-Dimethyl-4-aminopyridine
DMF: N,N-Dimethylformamide
DMSO: Dimethyl sulfoxide
HATU: 1-[Bis(dimethylamino)methylene]-1H-1,2,3-triazolo[4,5-b]pyridinium 3-oxide hexafluorophosphate
HOAt: 1-Hydroxy-7-azabenzotriazole HOBT: 1-Hydroxybenzotriazole
Me: Methyl
Ms: Mesyl
Ph: Phenyl
TBS: tert-Butyldimethylsilyl
THF: Tetrahydrofuran
TLC: Thin layer chromatography
Ts: Tosyl
WSC: 1-Ethyl-3-(3-dimethylaminopropyl)carbodiimide hydrochloride
(Preparation Methods)
Compounds Provided by the Present Invention that are Compounds Represented by the Aforementioned General Formula (I) Wherein $R^5$, $R^{6a}$, $R^{6b}$, $R^7$, $R^8$, $R^9$, and $R^{10}$ are Hydrogens The following compound (I) that is a compound provided by the present invention can be obtained by, for example, a deprotection reaction for converting the following compound (I-A) into the compound (I).

[Formula 3]

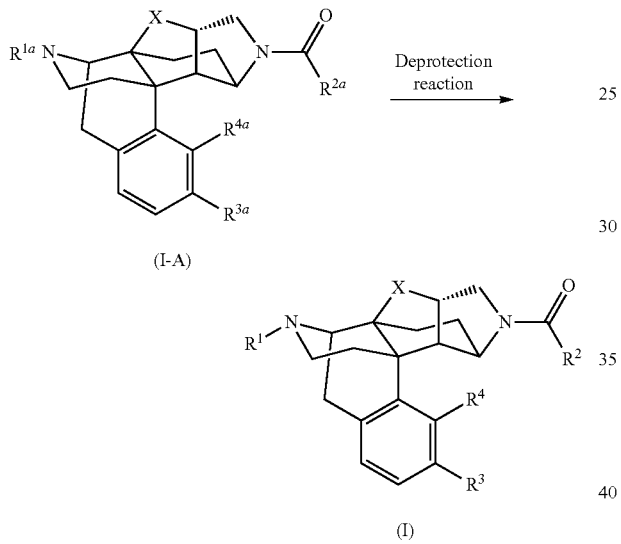

[In the formulas, $R^{1a}$, $R^{2a}$, $R^{3a}$, and $R^{4a}$ are arbitrary functional groups that can be converted into $R^1$, $R^2$, $R^3$, and $R^4$ in the aforementioned general formula (I), respectively, or $R^{1a}$ itself may be $R^1$, $R^{2a}$ itself may be $R^2$, $R^{3a}$ itself may be $R^3$, and $R^{4a}$ itself may be $R^4$. The other symbols have the same meanings as those defined above.]

In the aforementioned preparation method, the aforementioned compound (I) can be prepared by performing an appropriate known general deprotection reaction as required to convert $R^{1a}$ of the aforementioned compound (I-A) into $R^1$, $R^{2a}$ of the same into $R^2$, $R^{3a}$ of the same into $R^3$, or $R^{4a}$ of the same into $R^4$. For example, when $R^{1a}$, $R^{2a}$, $R^3$, or $R^{4a}$ in the aforementioned compound (I-A) contains hydroxy group protected with methyl group, the methyl group as the protective group can be removed by (1) a method of allowing boron tribromide to act on the aforementioned compound (I-A) in dichloromethane, or (2) a method of heating the aforementioned compound (I-A) together with a large excess amount of pyridine hydrochloride in the absence of solvent, and thereby, the aforementioned compound (I) can be prepared.

When $R^{1a}$, $R^{2a}$, $R^{3a}$, or $R^{4a}$ in the aforementioned compound (I-A) contains hydroxy group protected with tert-butyldimethylsilyl (TBS) group, the TBS group as the protective group can be removed by (3) a method of allowing ammonia dissolved in an appropriate solvent to act on the aforementioned compound (I-A), (4) a method of allowing hydrogen chloride dissolved in an appropriate solvent to act on the aforementioned compound (I-A), or (5) a method of allowing tetrabutylammonium fluoride to act on the aforementioned compound (I-A) in THF, or the like, and thereby, the aforementioned compound (I) can be prepared.

When $R^{1a}$, $R^{2a}$, $R^{3a}$, or $R^{4a}$ contains a functional group protected with another protective group, the aforementioned compound (I) can be prepared from the aforementioned compound (I-A) under the general deprotection conditions such as those explained in Peter G. M. Wuts, "Green's Protective Groups in Organic Synthesis (5th edition. A John Wiley & Son's, Inc., Publication).

When $R^{1a}$, $R^{2a}$, $R^{3a}$, and $R^{4a}$ have different protective groups, and they must be removed under different conditions, deprotection reactions may be successively performed under different conditions suitable for removing the protective groups as a multi-step deprotection reaction to prepare the aforementioned compound (I) from the aforementioned compound (I-A).

The aforementioned compound (I-A) can be obtained by, for example, performing a general acylation reaction for the following compound (I-B) mentioned in the reaction formula shown below.

[Formula 4]

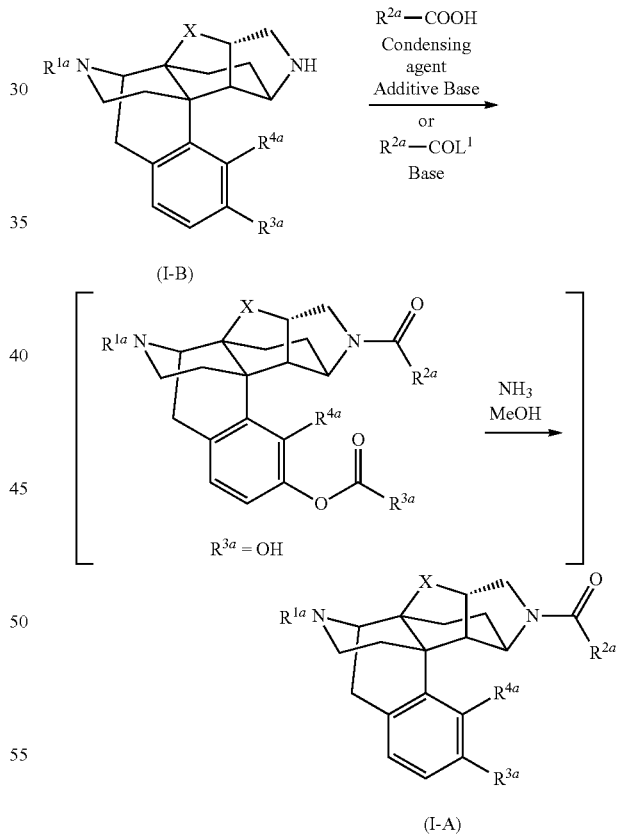

[In the formulas, $R^{1a}$, $R^{2a}$, $R^3$, and $R^{4a}$ are arbitrary functional groups that can be converted into $R^1$, $R^2$, $R^3$, and $R^4$ in the aforementioned general formula (I), respectively, or $R^{1a}$ itself may be $R^1$, $R^{2a}$ itself may be $R^2$, $R^{3a}$ itself may be $R^3$, and $R^{4a}$ itself may be $R^4$. $L^1$ represents a leaving group of a common acylating agent. The other symbols have the same meanings as those defined above.]

In the aforementioned preparation method, the aforementioned compound (I-A) can be obtained by reacting the aforementioned compound (I-B), a carboxylic acid ($R^{2a}$COOH), and a condensing agent such as HATU and WSC in the presence of an additive such as HOBT and DMAP, and a base such as triethylamine and diisopropylethylamine, as required.

The aforementioned compound (I-A) can also be obtained by reacting the aforementioned compound (I-B), a carboxylic acid chloride ($R^{2a}$COCl, $L^1$ in the formula=Cl) or a carboxylic anhydride ($L^1$ in the formula=—OC(O)$R^{2a}$) in the presence of a base such as triethylamine, diisopropylethylamine, and pyridine.

When $R^{3a}$ is hydroxy group (OH), in the acylation reaction mentioned in the above reaction formula, acylation of hydroxy group of $R^{3a}$ also progresses as a side reaction in addition to the desired amidation reaction, and a product corresponding to the aforementioned compound (I-A) wherein $R^{3a}$=—OC(O)$R^{2a}$ is temporarily obtained as a by-product in the reaction system. However, by treating the reaction solution with a 2 N ammonia solution in methanol or the like, such a compound is converted again into a compound where $R^{3a}$=OH in a post-treatment process, and the aforementioned compound (I-A) resulting from selective amidation of the secondary amine in the aforementioned compound (I-B) can be obtained as a result.

In addition, the aforementioned compound (I-A) can also be synthesized from the aforementioned compound (I-B) and a corresponding carboxylic acid ($R^{2a}$—COOH) according to the condensation reaction explained in Christian A. G. N. Montalbetti, et al., Tetrahedron, 61(46), 2005, 10827-10852.

A desired compound (I-A) can be obtained by using, for example, the compounds described in WO2013/035833 such as compound 8 (Example 4, $R^{1\ a}$=CPM, X=O, $R^{3\ a}$=OMe, $R^{4\ a}$=H), compound 33 (Example 29, $R^{1\ a}$=Me, X=O, $R^{3\ a}$=OMe, $R^{4\ a}$=H), compound 67 (Example 60, $R^{1\ a}$=CPM, X=O, $R^{3\ a}$=H, $R^{4\ a}$=OH), compound 77 (Example 67, $R^{1\ a}$=CPM, X=CH$_2$, $R^{3\ a}$=OMe, $R^{4\ a}$=H), compound 116 (Example 101, $R^{1\ a}$=CPM, X=CH$_2$, $R^{3\ a}$=H, $R^{4\ a}$=OH), compound 130 (Example 106, $R^{1\ a}$=PhCF$_2$ CH$_2$, X=CH$_2$, $R^{3\ a}$=OMe, $R^{4\ a}$=H), compound 185 (Example 143, $R^{1\ a}$=TBSOCH$_2$ CH$_2$, X=CH$_2$, $R^{3\ a}$=OMe, $R^{4\ a}$=H), compound 189 (Example 144, $R^{1\ a}$=(R)-MeCH(OH)CH$_2$, X=CH$_2$, $R^{3\ a}$=OMe, $R^{4\ a}$=H), compound 261 (Example 261, $R^{1\ a}$=(S)-MeCH(OH)CH$_2$, X=CH$_2$, $R^{3\ a}$=OMe, $R^{4\ a}$=H), compound 291 (Example 224, $R^{1\ a}$=CPM, X=CH$_2$, $R^{3\ a}$=H, $R^{4\ a}$=OMe), and compound 297 (Example 228, $R^{1\ a}$=CPM, X=CH$_2$, $R^{3\ a}$=H, $R^{4\ a}$=H), and the compounds described in WO2014/136305 such as compound 29 (Example 27, $R^{1\ a}$=BocNHCH$_2$ CH$_2$, X=CH$_2$, $R^{3\ a}$=OTBS, $R^{4\ a}$=H), and compound 68 (Example 34, $R^{1'a}$=Boc, X=CH$_2$, $R^{3\ a}$=OMe, $R^{4\ a}$=H) as the aforementioned compound (I-B), or by a combination of a known conversion of functional group and deprotection reaction performed by a method described in the aforementioned patent documents.

The following compound (I-A) can also be obtained by, for example, a common alkylation reaction of the following compound (I-C) mentioned in the reaction formula shown below.

[Formula 5]

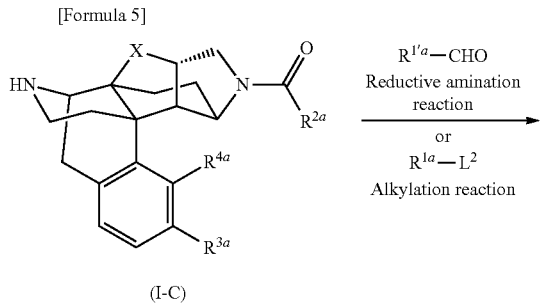

(I-C)

$R^{1'a}$—CHO
Reductive amination reaction or $R^{1a}$—$L^2$
Alkylation reaction -continued

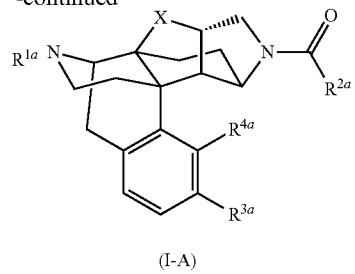

(I-A)

[In the formulas, $R^{1a}$, $R^{2a}$, $R^{3a}$, and $R^{4a}$ are arbitrary functional groups that can be converted into $R^1$, $R^2$, $R^3$, and $R^4$ in the aforementioned general formula (I), respectively, or $R^{1a}$ itself may be $R^1$, $R^{2a}$ itself may be $R^2$, $R^{3a}$ itself may be $R^3$, and $R^{4a}$ itself may be $R^4$. $L^2$ represents a leaving group for a common alkylating reaction, $R^{1'a}$ represents such a substituent that $R^{1'a}$—CH$_2$=$R^{1a}$ is satisfied, and the other symbols have the same meanings as those defined above.]

In the aforementioned preparation method, the aforementioned compound (I-A) can be synthesized by allowing a corresponding aldehyde ($R^{1'a}$—CHO, $R^{1'a}$ represents such a substituent that $R^{1'a}$—CH$_2$=$R^{1a}$ is satisfied), and a reducing agent such as sodium triacetoxyborohydride or sodium cyanoborohydride to act on the aforementioned compound (I-C) in an appropriate solvent in the presence of an additive such as acetic acid as required.

The aforementioned compound (I-A) can also be synthesized by allowing a corresponding alkylating agent ($R^{1a}$-$L^2$, $L^2$ represents an appropriate leaving group, for example, halogen such as Cl, Br, and I, OMs, or OTs) to act on the aforementioned compound (I-C) in a polar solvent such as DMF or an alcohol in the presence of a base such as potassium carbonate.

In addition, the method for introducing the $R^{1a}$ group into the aforementioned compound (I-C) is not limited to the reactions described above, and by using a known general alkyl group introduction reaction for amino group, which may be a multi-step reaction, the aforementioned compound (I-A) can be prepared from the aforementioned compound (I-C).

The aforementioned compound (I-C) can be synthesized by a combination of known functional group conversion and deprotection reaction of an appropriate starting material described in any of the aforementioned references according to a method similar to any of the synthesis methods of, for example, the compounds described in WO02013/035833 such as compound 11 (Example 7, $R^{2\ a}$=Ph, X=O, $R^{3\ a}$=OMe, $R^{4\ a}$=H), compound 81 (Example 71, $R^{2\ a}$=Ph, X=CH$_2$, $R^{3\ a}$=OMe, $R^{4\ a}$=H), compound 121 (Example 104, $R^{2\ a}$=Ph, X=CH$_2$, $R^{3\ a}$=OTBS, $R^{4\ a}$=H), compound 149 (Example 120, $R^{2\ a}$=2-pyridil, X=CH$_2$, $R^{3\ a}$=OMe, $R^{4\ a}$=H), compound 116 (Example 101, $R^{1\ a}$=CPM, X=CH$_2$, $R^{3\ a}$=OMe, $R^{4\ a}$=H), and compound 217 (Example 163, $R^{2\ a}$=CF$_3$, X=CH$_2$, $R^{3\ a}$=OMe, $R^{4\ a}$=H).

The compounds represented by the aforementioned general formula (I) of the other types as the compounds provided by the present invention can also be prepared by a combination of any of the aforementioned preparation methods, methods described in the examples mentioned later, and those described in Patent documents 4 to 6, Non-patent document 11, and the like.

The compound represented by the aforementioned general formula (I), a tautomer or stereoisomer thereof, or a pharmaceutically acceptable salt or a solvate thereof showed superior agonistic activity and selectivity for the opioid δ receptor in a test concerning functional activities for the μ, δ, and κ opioid receptors (refer to Example 40, Table 6).

The compound represented by the aforementioned general formula (I), a tautomer or stereoisomer thereof, or a pharmaceutically acceptable salt or a solvate thereof significantly increased the wall-less running route (open arm) staying time ratio in the mouse and rat elevated plus maze tests, and thus exhibited anxiolytic-like effects (refer to Examples 41 and 42, FIGS. 1 to 6). The elevated plus maze tests were performed according to the method described in Non-patent document 6.

It was also revealed that the compound represented by the aforementioned general formula (I), a tautomer or stereoisomer thereof, or a pharmaceutically acceptable salt or a solvate thereof has a superior antidepressive action in a hyperemotional reaction inhibition test using an olfactory bulbectomized (OBX) rat (Example 44).

Therapeutic effect for Parkinson's disease of the compound represented by the aforementioned general formula (I), a tautomer or stereoisomer thereof, or a pharmaceutically acceptable salt or a solvate thereof was also suggested in a reserpine-induced Parkinson's disease model mouse (Example 45).

The compound represented by the aforementioned general formula (I), a tautomer or stereoisomer thereof, or a pharmaceutically acceptable salt or a solvate thereof showed a tendency of dose-dependently prolonging urination interval and increasing single urination amount in a test using a rat cerebral infarction-induced overactive bladder model, and accordingly, pollakiuria-improving action of the test substance was suggested (Example 46, Table 8).

Further, the compound represented by the aforementioned general formula (I), a tautomer or stereoisomer thereof, or a pharmaceutically acceptable salt or a solvate thereof showed only weak inhibitory action in a hERG (human ether-a-go-go-related gene) potassium channel inhibition test as described in Example 43 mentioned later. This indicates that the risks of the compounds represented by the aforementioned general formula (I), tautomers or stereoisomers of the compounds, pharmaceutically acceptable salts thereof, and solvates thereof for retarding the ventricular repolarization and prolonging the QT interval in humans are low.

In addition, it was also revealed that the compound represented by the aforementioned general formula (I), a tautomer or stereoisomer thereof, or a pharmaceutically acceptable salt or a solvate thereof has central migration sufficient for exhibiting efficacy, and high stability in a metabolic stability test using human hepatic microsomes, and it was revealed that they are orally administrable compounds having anxiolytic effects, antidepressive effects, analgesic effects, anti-Parkinson effects, and pollakiuria and urinary incontinence-improving effects. As for evaluation of metabolic stability using human hepatic microsomes, the metabolic stability can be evaluated by adding a known amount of a test compound to human hepatic microsomes, incubating them for a certain period of time, and then quantifying the amount of the compound using LC (liquid chromatography) or the like (Example 47, Table 9).

Therefore, in consideration of the descriptions of Patent documents 1 to 6, Non-patent document 1 to 10 mentioned above, and the like, the compounds represented by aforementioned general formula (I), tautomers or stereoisomers of the compounds, pharmaceutically acceptable salts thereof, and solvates thereof can be used for the treatment and the prevention of depression or anxiety, and can be used as prophylactic and therapeutic agents for psychiatric disorders included in the depression disorder group, anxiety disorder group, bipolar disorder group, obsessive-compulsive disorder and related disorder group, psychic trauma and stress factor-related disorder group, and the like described in DSM-5 (Diagnostic and Statistical Manual of Mental Disorders, 5th edition, American Psychiatric Association) (antidepressants, anxiolytic drugs, etc.), and as prophylactic and therapeutic agents for neurodegenerative diseases such as urinary incontinence, myocardial ischemia, brain ischemia, chronic coughing, hypertension, Parkinson's disease, and epilepsy.

As described in IOVS, March 2013, Vol. 54, No. 3; J. Neurochem. (2009) 108, 741-754, and the like, application of opioid δ agonists to glaucoma has also be proposed. Therefore, the compounds represented by the aforementioned general formula (I), tautomers or stereoisomers of the compounds, pharmaceutically acceptable salts thereof, and solvates thereof can be used as prophylactic or therapeutic agents for glaucoma.

As used herein, depression may be a state that there is observed a combination of a mood disorder such as depressive feeling, sad feeling, and lonely feeling, decrease in activity volition, congestion of ideas, pessimistic idea, and an autonomic nerve disorder such as sleep disorder and decrease in appetite. As used herein, anxiety may be a state of feeling danger or fear with restlessness, strain, tachycardia, breathing difficulty, and the like, although the state is not connected with a stimulus that can be clearly confirmed. The depression and anxiety include the depressive and anxiety symptoms observed in the psychiatric disorders described in DSM-5 mentioned above (for example, depressive symptoms observed in bipolar disorders, and depressive and anxious symptoms observed in PTSD), depressive state of which symptoms are milder than those of the depression disorders described in DSM-5, but are maintained in a certain degree, and anxious state of which symptoms are milder than those of the anxiety disorders described in DSM-5, but are maintained in a certain degree.

Further, the compounds represented by the aforementioned general formula (I), tautomers or stereoisomers of the compounds, or pharmaceutically acceptable salts thereof, or solvates thereof may be used as medicaments for assisting the therapeutic treatment of any of the aforementioned diseases.

The compounds represented by the aforementioned general formula (I), tautomers or stereoisomers of the compounds, pharmaceutically acceptable salts thereof, and solvates thereof can also be used for therapies of pains regarding diseases accompanied by an acute pain or chronic pain, or as prophylactic and therapeutic agents for pains of rheumatoid arthritis, osteoarthritis deformans, cancer pain accompanied by severe pain such as osteoncus, diabetic neuropathic pain, postherpetic neuralgia, visceral pains, and the like.

The compounds represented by the aforementioned general formula (I), tautomer or stereoisomers of the compounds, pharmaceutically acceptable salts thereof, and solvates thereof are preferably expected to be antidepressants and anxiolytic drugs.

The compounds represented by the aforementioned general formula (I), tautomers or stereoisomers of the compounds, pharmaceutically acceptable salts thereof, and solvates thereof can be administered to a human by an appropriate administration method such as oral administration or parenteral administration. Further, they can be used together with other anxiolytic drugs, antidepressants, and analgesics.

As for preparation of pharmaceutical preparations thereof, they can be prepared in a dosage form of tablet, granule, powder, capsule, suspension, injection, suppository or the like by methods commonly used in the field of pharmaceuticals.

For preparation of such pharmaceutical preparations, for example, commonly used excipients, disintegrating agents, binders, lubricants, dyes, and the like are used in the case of tablet. Examples of the excipients include lactose, D-mannitol, crystalline cellulose, glucose, and the like. Examples of the disintegrating agents include starch, carboxymethylcellulose calcium (CMC-Ca), and the like. Examples of the lubricants include magnesium stearate, talc, and the like. Examples of the binders include hydroxypropylcellulose (HPC), gelatin, polyvinylpyrrolidone (PVP), and the like. For the preparation of injection, solvents, stabilizers, dissolving aids, suspending agents, emulsifiers, soothing agents, buffering agents, preservatives, and the like are used.

As for the dose of the compound represented by the aforementioned general formula (I), a tautomer or stereoisomer of the compound, or a pharmaceutically acceptable salt thereof, or a solvate thereof as active ingredient, it is usually administered to adults at a dose of 0.1 µg to 1 g/day, preferably 0.001 to 200 mg/day, in the case of injection; or at a dose of 1 µg to 10 g/day, preferably 0.01 to 2000 mg/day, in the case of oral administration, but the dose may be decreased or increased depending on age, symptoms, and the like.

Hereafter, the present invention will be further explained in more detail with reference to reference examples and examples. However, the present invention is not limited to these examples.

Names of the compounds mentioned in the examples and reference examples are obtained by converting structural formulas depicted with ChemDraw ver. 14, Cambridge Software into English compound names with a naming algorithm of the same software, and translating them into Japanese names.

The NMR data and the measured values of mass spectrometry (ESI+ or ESI−) of Examples 1 to 34 are shown in Tables 1 to 5.

EXAMPLES

Reference Example 1-1

Synthesis of (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol

[Formula 6]

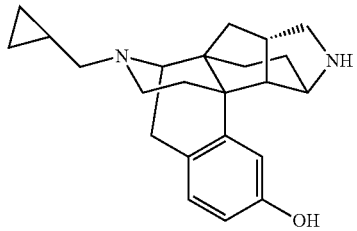

To a 300-mL round bottom flask, (1S,3aR,5aS,6R,11bR,11cS)-14-(cyclopropylmethyl)-10-methoxy-2,3,3a,4,5,6,7,11c-octahydro-1H-6,11b-(epiminoethano)-1,5a-methanonaphtho[1,2-e]indole (372 mg, 1.02 mmol) synthesized according to the method of WO2013/035833, Example 67 was added, and dissolved in dichloromethane (5 mL), the solution was vigorously stirred at 0° C. for 20 minutes, then a 1.0 M solution of boron tribromide in dichloromethane (5 mL, 5 mmol) was added to the solution, and the resulting mixture was stirred at room temperature for 30 minutes. To the reaction solution, methanol (10 mL) was added at 0° C., and the resulting mixture was stirred at the same temperature for 1 hour.

The reaction solution was concentrated under reduced pressure, and the residue was suspended in chloroform (50 mL), and washed with 6% aqueous ammonia (20 mL). The aqueous layer was extracted twice with chloroform (30 mL), the combined organic layers were dried over anhydrous sodium sulfate, the insoluble matter was separated by filtration, and then the filtrate was concentrated under reduced pressure to obtain the title compound (356 mg, 100%) as brown foam.

[Alternative Method]

To a 500-mL round bottom flask, (1S,3aR,5aS,6R,11bR,11cS)-14-(cyclopropylmethyl)-10-methoxy-2,3,3a,4,5,6,7,11c-octahydro-1H-6,11b-(epiminoethano)-1,5a-methanonaphtho[1,2-e]indole (3.58 g, 9.82 mmol) synthesized according to the method of WO2013/035833, Example 67, and pyridine hydrochloride (87 g, 753 mmol) were added, and the mixture was stirred at 200° C. for 1 hour. After the reaction, the reaction mixture was returned to room temperature, saturated aqueous potassium carbonate was added to the produced solid to dissolve it, the solution was extracted with ethyl acetate and chloroform, and the combined organic layers were dried over anhydrous sodium sulfate. The insoluble matter was separated by filtration, and then the filtrate was concentrated under reduced pressure to obtain the title compound (3.30 g, 96%) as brown foam.

$^1$H NMR (CDCl$_3$, 400 MHz): δ 6.94 (d, 1H, J=8.2 Hz), 6.70 (dd, 1H, J=8.2, 2.8 Hz), 6.50 (d, 1H, J=2.3 Hz), 3.73-3.76 (m, 1H), 3.23-3.31 (m, 2H), 3.05-3.12 (m, 2H), 2.77-2.99 (m, 4H), 2.55 (dd, 1H, J=11.0, 5.0 Hz), 2.31 (d, 1H, J=6.4 Hz), 1.91-2.11 (m, 2H), 1.69-1.74 (m, 1H), 1.20-1.45 (m, 3H), 0.93-1.10 (m, 3H), 0.77-0.83 (m, 1H), 0.42-0.51 (m, 2H), 0.05-0.14 (m, 2H)

Reference Example 1-2

Synthesis of (1S,3aR,5aS,6R,11bR,11cS)-10-((tert-butyldimethylsilyl)oxy)-14-(cyclopropylmethyl)-2,3,3a,4,5,6,7,11c-octahydro-1H-6,11b-(epiminoethano)-1,5a-methanonaphtho[1,2-e]indole

[Formula 7]

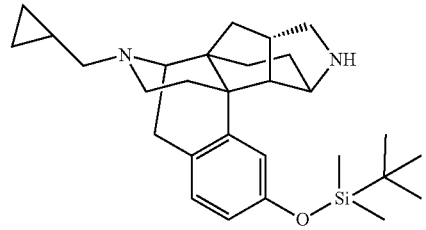

To a 200-mL round bottom flask, (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (694 mg, 1.98 mmol) synthesized according to the method of Reference Example 1-1 was added, and dissolved in DMF (20 mL), imidazole (241 mg, 3.54 mmol) and tert-butyldimethylchlorosilane (498 mg, 3.31 mmol) were added to the solution at room temperature, and the resulting mixture was stirred at room temperature for 2 hours. Since it was confirmed that the starting material remained in the reaction solution, imidazole (529 mg, 7.77 mmol) and tert-butyldimethylchlorosilane (503 mg, 3.34 mmol) were added to the reaction solution, and the resulting mixture was stirred at room temperature for 18 hours. To the reaction solution, water (150 mL) was added, and the resulting mixture was extracted with a mixed solvent of ethyl acetate and hexane (1:1, 100 mL). 6% Aqueous ammonia (30 mL) was added to the aqueous layer to make it basic, and then the resulting mixture was extracted twice with a mixed solvent of ethyl acetate and hexane (1:1, 100 mL). The combined organic layers were dried over anhydrous magnesium sulfate, then the insoluble matter was separated by filtration, and the filtrate was concentrated under reduced pressure. The residue was purified by column chromatography (silica gel, 25 g) using methanol/chloroform (concentration gradient, 0 to 50%) and then methanol containing 10% concentrated aqueous ammonia/chloroform (concentration gradient, 20 to 50%) as the elution solvent to obtain the title compound (456 mg, 50%) as yellow syrup, and obtain the starting material, (1S,3aR,5aS,6R,11bR, 11cS)-14-(cyclopropylmethyl)-2,3,3a,4,5,6,7,11c-octahydro-1H-6,11b-(epiminoethano)-1,5a-methanonaphtho[1, 2-e]indol-10-ol (265 mg, 38%).

$^1$H NMR (CDCl$_3$, 400 MHz): δ 6.94 (d, 1H, J=8.2 Hz), 6.65 (d, 1H, J=2.8 Hz), 6.59 (dd, 1H, J=8.2, 2.8 Hz), 3.49-3.53 (m, 1H), 3.33 (dd, 1H, J=8.2, 7.8 Hz), 3.08-3.18 (m, 2H), 2.77-2.96 (m, 4H), 2.71 (t, 1H, J=7.3 Hz), 2.51-2.55 (m, 1H), 2.30 (d, 2H, J=6.4 Hz), 1.90-2.03 (m, 2H), 1.63-1.68 (m, 1H), 1.35-1.43 (m, 1H), 0.91-1.13 (m, 14H), 0.77-0.83 (m, 1H), 0.42-0.51 (m, 2H), 0.16 (s, 6H), 0.08-0.10 (m, 2H)

Example 1

Synthesis of 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide

[Formula 8]

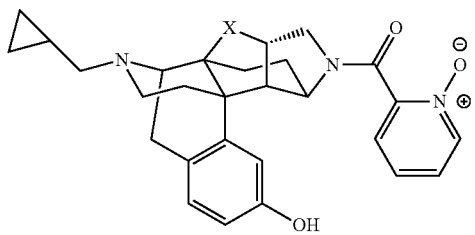

To a 50-mL round bottom flask, (1S,3aR,5aS,6R,11bR, 11cS)-14-(cyclopropylmethyl)-2,3,3a,4,5,6,7,11c-octahydro-1H-6,11b-(epiminoethano)-1,5a-methanonaphtho[1, 2-e]indol-10-ol (31 mg, 87 μmol) synthesized in Reference Example 1, 2-carboxypyridine 1-oxide (32 mg, 0.23 mmol), and HATU (125 mg, 0.33 mmol) were added, and suspended in THF (1.5 mL), then triethylamine (70 μL, 0.50 mmol) and DMA (200 μL) were added to the suspension, and the resulting mixture was stirred for 1 hour at room temperature. To the reaction mixture, a 2 N solution of ammonia in methanol (2 mL) was added, and the resulting mixture was stirred at the same temperature for 1 hour. The reaction solution was concentrated under reduced pressure, the obtained residue was suspended in 6% aqueous ammonia, and the suspension was extracted with ethyl acetate. The combined organic layers were washed with saturated brine, and then dried over anhydrous magnesium sulfate, the insoluble substance was separated by filtration, and then the filtrate was concentrated under reduced pressure. The obtained residue was subjected to column chromatography (aminosilica gel, 16 g) using methanol and chloroform (concentration gradient, 0 to 50%) as the elution solvent to obtain the title compound (18 mg, 44%) as white solid.

Example 2

Synthesis of 4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide

[Formula 9]

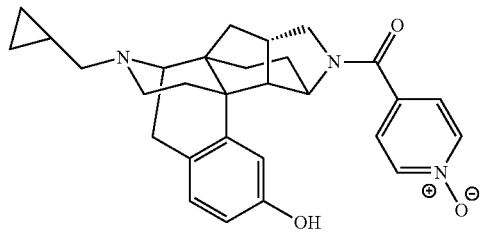

In the same manner as that of Example 1, (1S,3aR,5aS, 6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (36 mg, 0.10 mmol), 4-carboxypyridine 1-oxide (42 mg, 0.30 mmol), triethylamine (70 μL, 0.50 mmol), and HATU (108 mg, 0.28 mmol) were reacted. The reaction solution was directly subjected to column chromatography (silica gel, 10 g) using methanol and ethyl acetate containing 5% triethylamine (concentration gradient, 10 to 50%) as the elution solvent, and thereby purified. The obtained syrup was dissolved in methanol, then powdered by adding chloroform and tert-butyl methyl ether to the solution, and then collected by filtration to obtain the title compound (30 mg, 62%) as weakly brown solid.

Example 3

Synthesis of 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one

[Formula 10]

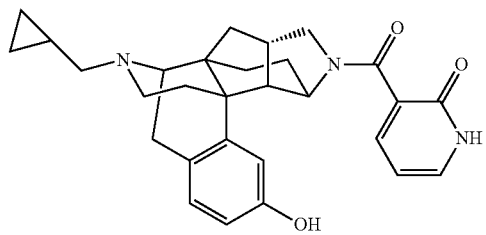

In the same manner as that of Example 1, (1S,3aR,5aS, 6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (39 mg, 0.11 mmol), 2-oxo-1,2-dihydropyridine-3-carboxylic acid (39 mg, 0.28 mmol), triethylamine (70 μL, 0.50 mmol), and HATU (130 mg, 0.34 mmol) were reacted. To the reaction solution, a 2 N solution of ammonia in methanol was added to terminate the reaction, then the reaction solution was concentrated under reduced pressure, and the residue was directly subjected to column chromatography (silica gel, 10 g) using methanol and ethyl acetate containing 5% triethylamine (concentration gradient, 10 to 50%) as the elution solvent, and thereby purified. The obtained residue was powdered from 6% aqueous ammonia to obtain the title compound (13 mg, 25%) as pale yellow powder.

Example 4

Synthesis of 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide

[Formula 11]

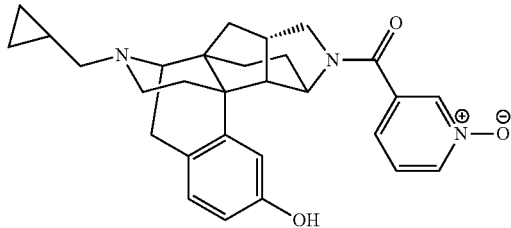

In the same manner as that of Example 1, (1S,3aR,5aS, 6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (34 mg, 97 µmol), 3-carboxypyridine 1-oxide (40 mg, 0.29 mmol), triethylamine (70 µL, 0.50 mmol), and HATU (125 mg, 0.33 mmol) were reacted. To the reaction solution, a 2 N solution of ammonia in methanol was added to terminate the reaction, then the reaction solution was concentrated under reduced pressure, and the residue was directly subjected to column chromatography (silica gel, 25 g) using a 0.1 N solution of ammonia in methanol and chloroform (concentration gradient, 0 to 50%) as the elution solvent, and thereby purified. The obtained syrup was dissolved in methanol, then powdered by adding tert-butyl methyl ether to the solution, and then collected by filtration to obtain the title compound (14 mg, 31%) as weakly brown amorphous substance.

Example 5

Synthesis of 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one

[Formula 12]

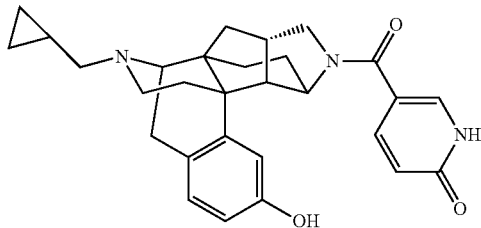

In the same manner as that of Example 1, (1S,3aR,5aS, 6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (34 mg, 96 µmol), 6-oxo-1,6-dihydropyridine-3-carboxylic acid (40 mg, 0.29 mmol), triethylamine (70 µL, 0.50 mmol), and HATU (132 mg, 0.35 mmol) were reacted. To the reaction solution, a 2 N solution of ammonia in methanol was added to terminate the reaction, and then the reaction solution was concentrated under reduced pressure. The residue was directly subjected to column chromatography (silica gel, 10 g) using a 0.1 N solution of ammonia in methanol and chloroform (concentration gradient, 1 to 50%) as the elution solvent, and thereby purified. In order to eliminate impurities, the obtained compound was suspended in chloroform, and then the suspension was washed with 6% aqueous ammonia. The aqueous layer was extracted with chloroform, then the combined organic layers were dried over anhydrous sodium sulfate, then the insoluble substance was separated by filtration, and the filtrate was concentrated under reduced pressure to obtain the title compound (14 mg, 30%) as pale yellow powder.

Reference Example 2

Synthesis of 1-methyl-2-oxo-1,2-dihydropyridine-3-carboxylic Acid

[Formula 13]

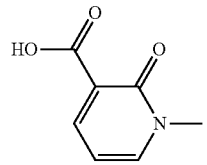

This compound was synthesized by a method similar to the method described in WO2006/107254.

To a 50-mL round bottom flask, 2-oxo-1,2-dihydropyridine-3-carboxylic acid (500 mg, 3.59 mmol) was added, and suspended in methanol (5 mL) and water (0.8 mL), then potassium hydroxide (400 mg, 7.13 mmol) was added to the suspension, and the resulting mixture was stirred at 100° C. for 15 minutes. The reaction solution was returned to room temperature, iodomethane (2.6 mL, 41.8 mmol) was added to the reaction solution, and the resulting mixture was stirred at 100° C. for 45 minutes, and then concentrated under reduced pressure until the solvent volume was reduced by half. To the reaction solution, 3 N hydrochloric acid (20 mL) was added, and the produced solid was collected by filtration, washed with water and acetonitrile, and then dried under reduced pressure to obtain the title compound (64.9 mg, 12%) as white powder.

1H NMR (CD$_3$OD, 400 MHz): δ 8.43 (dd, 1H, J=6.9, 2.3 Hz), 8.05 (dd, 1H, J=6.9, 2.3 Hz), 6.65 (t, 1H, J=6.9 Hz), 3.70 (s, 3H)

Example 6

Synthesis of 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one

[Formula 14]

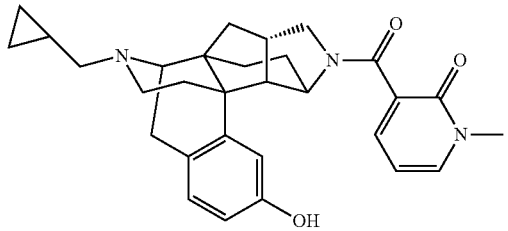

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (30 mg, 86 μmol), 1-methyl-2-oxo-1,2-dihydropyridine-3-carboxylic acid (29 mg, 0.19 mmol) synthesized in Reference Example 2, diisopropylethylamine (75 μL, 0.43 mmol), and HATU (72 mg, 0.19 mmol) were reacted in the same manner as that of Example 1, except that dichloromethane was used as the solvent instead of THF and DMA. To the reaction solution, a 1.4 N solution of ammonia in methanol was added to terminate the reaction, and then the reaction solution was concentrated under reduced pressure. The residue was suspended in saturated aqueous sodium hydrogen carbonate, then the suspension was extracted with chloroform, and the organic layer was dried over anhydrous sodium sulfate. The insoluble substance was separated by filtration, and then the filtrate was concentrated under reduced pressure. The obtained residue was subjected to preparative TLC using a 1.4 N solution of ammonia in methanol and chloroform (concentration, 5%) as the developing solvent to obtain the title compound (26.2 mg, 63%) as pale yellow amorphous substance.

Example 7

Synthesis of 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one

[Formula 15]

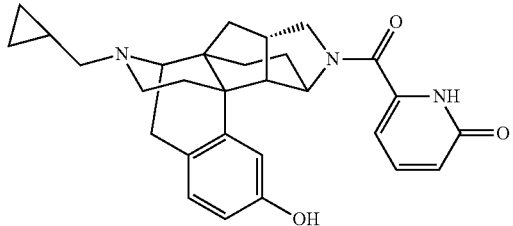

In the same manner as that of Example 1, (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (66 mg, 0.19 mmol), 6-oxo-1,6-dihydropyridine-2-carboxylic acid (83 mg, 0.59 mmol), triethylamine (150 &L, 1.10 mmol), and HATU (262 mg, 0.69 mmol) were reacted. To the reaction solution, a 2 N solution of ammonia in methanol was added to terminate the reaction, and then the reaction solution was concentrated under reduced pressure. The residue was directly subjected to column chromatography (aminosilica gel, 10 g) using methanol and chloroform (concentration gradient, 0 to 30%) as the elution solvent, and thereby purified. The obtained syrup was dissolved in methanol, and powdered by adding tert-butyl methyl ether to the solution to obtain the title compound (83 mg, 94%) as brown solid.

Example 8

Synthesis of 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-6-methylpyridin-2(1H)-one

[Formula 16]

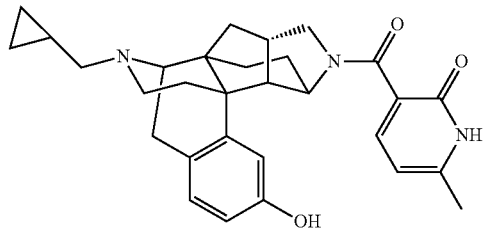

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (20 mg, 57 mol), 6-methyl-2-oxo-1,2-dihydropyridine-3-carboxylic acid (19 mg, 0.13 mmol), diisopropylethylamine (50 μL, 0.29 mmol), and HATU (48 mg, 0.13 mmol) were reacted in the same manner as that of Example 1, except that DMF was used as the solvent instead of THF and DMA. To the reaction solution, a 1.4 N solution of ammonia in methanol was added to terminate the reaction, and then the reaction solution was concentrated under reduced pressure. The residue was subjected to preparative TLC using a 1.4 N solution of ammonia in methanol and chloroform (concentration, 10%) as the developing solvent, and thereby purified. Then, in order to eliminate impurities, the obtained solid was further suspended in saturated aqueous potassium carbonate, and then extracted with chloroform. The organic layer was dried over anhydrous sodium sulfate, then the inorganic matter was separated by filtration, and the filtrate was concentrated under reduced pressure to obtain the title compound. The obtained compound was given as a hydrochloride salt according to Example 32 for use in the biological activity test.

Example 9

Synthesis of 5-(((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one

[Formula 17]

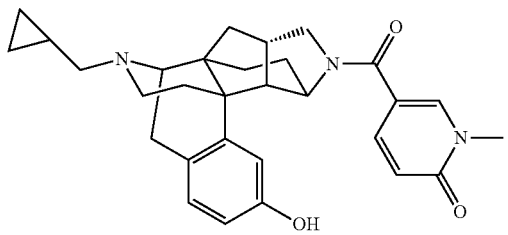

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (30 mg, 86 μmol), 1-methyl-6-oxo-1,6-dihydropyridine-3-carboxylic acid (29 mg, 0.19 mmol), diisopropylethylamine (75 μL, 0.43 mmol), and HATU (72 mg, 0.19 mmol) were reacted in the same manner as that of Example 1, except that dichloromethane was used as the solvent instead of THF and DMA. To the reaction solution, a 1.4 N solution of ammonia in methanol was added to terminate the reaction, and then the reaction solution was concentrated under reduced pressure. The residue was suspended in saturated aqueous sodium hydrogen carbonate, and then the suspension was extracted with chloroform. The organic layer was dried over anhydrous sodium sulfate, the insoluble substance was separated by filtration, and then the filtrate was concentrated under reduced pressure. The obtained residue was subjected to preparative TLC using methanol and chloroform (concentration, 10%) as a developing solvent to obtain the title compound (31.1 mg, 75%) as white amorphous substance.

Reference Example 3

Synthesis of 1-methyl-6-oxo-1,6-dihydropyridine-2-carboxylic Acid

[Formula 18]

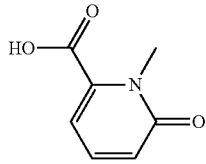

To a 50-mL round bottom flask, 6-oxo-1,6-dihydropyridine-2-carboxylic acid (500 mg, 3.59 mmol) was added, and suspended in methanol (5 mL) and water (0.8 mL), then potassium hydroxide (400 mg, 7.13 mmol) was added to the suspension, and the resulting mixture was stirred at 100° C. for 15 minutes. The reaction solution was returned to room temperature, iodomethane (2.6 mL, 41.8 mmol) was added to the reaction solution, and the resulting mixture was stirred at 100° C. for 1 hour, and then concentrated under reduced pressure until the solvent volume was reduced by half. To the reaction solution, 3 N hydrochloric acid was added, and the produced solid was collected by filtration, washed with water and acetonitrile, and then dried under reduced pressure to obtain the title compound (339 mg, 62%) as white powder.

$^1$H NMR (DMSO-$d_6$, 400 MHz): δ 7.45 (dd, 1H, J=9.2, 6.9 Hz), 6.72 (dd, 1H, J=6.9, 1.4 Hz), 6.59 (dd, 1H, J=9.2, 1.4 Hz), 3.51 (s, 3H)

Example 10

Synthesis of 6-(((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one

[Formula 19]

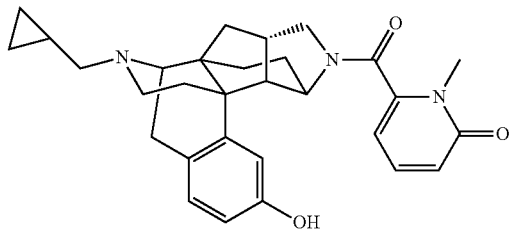

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (30 mg, 86 μmol), 1-methyl-6-oxo-1,6-dihydropyridine-2-carboxylic acid (29 mg, 0.19 mmol) synthesized according to the method of Reference Example 3, diisopropylethylamine (75 μL, 0.43 mmol), and HATU (72 mg, 0.19 mmol) were reacted in the same manner as that of Example 1, except that dichloromethane was used as the solvent instead of THF and DMA. To the reaction solution, a 1.4 N solution of ammonia in methanol was added to terminate the reaction, and then the reaction solution was concentrated under reduced pressure. The residue was suspended in saturated aqueous sodium hydrogen carbonate, and then the suspension was extracted with chloroform. The organic layer was dried over anhydrous sodium sulfate, the insoluble substance was separated by filtration, and then the filtrate was concentrated under reduced pressure. The obtained residue was subjected to preparative TLC using methanol and chloroform (concentration, 10%) as the developing solvent to obtain the title compound (32.7 mg, 79%) as white amorphous substance.

Example 11

Synthesis of 4-(((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one

[Formula 20]

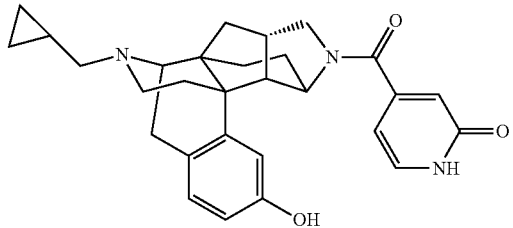

In the same manner as that of Example 1, (1S,3aR,5aS, 6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (54 mg, 0.15 mmol), 2-methoxyisonicotinic acid (54 mg, 0.35 mmol), triethylamine (140 µL, 1.00 mmol), and HATU (195 mg, 0.51 mmol) were reacted. To the reaction solution, a 2 N solution of ammonia in methanol was added to terminate the reaction, and then the reaction solution was concentrated under reduced pressure. The residue was suspended in chloroform, and then the suspension was washed with 6% aqueous ammonia. The aqueous layer was extracted with chloroform, the combined organic layers were dried over anhydrous magnesium sulfate, then the insoluble substance was separated by filtration, and the filtrate was concentrated under reduced pressure. The obtained residue was subjected to column chromatography (aminosilica gel, 16 g) using methanol containing 10% concentrated aqueous ammonia and chloroform as the elution solvent to obtain ((1S,3aR, 5aS,6R,11bR,11cS)-14-(cyclopropylmethyl)-10-hydroxy-1, 2,3a,4,5,6,7,11c-octahydro-3H-6,11b-(epiminoethano)-1, 5a-methanonaphtho[1,2-e]indol-3-yl)(2-methoxypyridin-4-yl)methanone (61 mg, 82%) as white solid.

$^1$H NMR (DMSO-d$_6$, 400 MHz): δ 8.20 (d, 0.6H, J=6.0 Hz), 8.15 (d, 0.4H, J=5.0 Hz), 6.88-6.97 (m, 2H), 6.80 (s, 0.6H), 6.74 (s, 0.4H), 6.64 (d, 0.6H, J=2.8 Hz), 6.56 (dd, 0.6H, J=8.2, 2.3 Hz), 6.45-6.51 (m, 0.8H), 4.06-4.16 (m, 1H), 3.92 (s, 1.8H), 3.88 (s, 1.2H), 3.64-3.69 (m, 0.6H), 3.43-3.37 (m, 2H), 3.14-3.17 (m, 1H), 2.97-3.09 (m, 1H), 2.82-2.91 (m, 2H), 2.52-2.56 (m, 1H), 2.29-2.31 (m, 2H), 1.88-2.08 (m, 2H), 1.66-1.80 (m, 1H), 1.42-1.57 (m, 1.6H), 1.02-1.23 (m, 2.4H), 0.75-0.96 (m, 2H), 0.42-0.49 (m, 2H), 0.05-0.14 (m, 2H)

To a 100-mL round bottom flask, ((1S,3aR,5aS,6R,11bR, 11cS)-14-(cyclopropylmethyl)-10-hydroxy-1,2,3a,4,5,6,7, 11c-octahydro-3H-6,11b-(epiminoethano)-1,5a-methanonaphtho[1,2-e]indol-3-yl)(2-methoxypyridin-4-yl)methanone obtained above (48 mg, 98 µmol), and pyridine hydrochloride (2.88 g, 25 mmol) were added, and the resulting mixture was stirred at 200° C. for 10 minutes with heating. The reaction solution was cooled to room temperature, and then suspended in 6% aqueous ammonia, and the suspension was extracted with ethyl acetate. The combined organic layers were dried over anhydrous magnesium sulfate, then the insoluble substance was separated by filtration, and the filtrate was concentrated under reduced pressure. The residue was subjected to column chromatography (aminosilica gel, 8 g) using methanol and chloroform (concentration gradient, 0 to 30%) as the elution solvent to obtain the title compound (35 mg, 75%) as white solid.

Example 12

Synthesis of 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrimidine-2,4(1H,3H)-dione

[Formula 21]

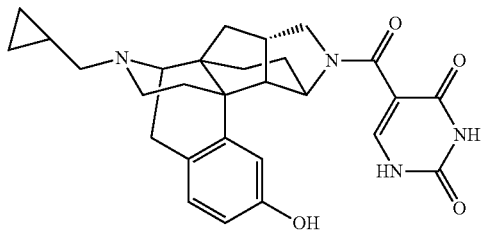

In the same manner as that of Example 1, (1S,3aR,5aS, 6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (32 mg, 90 µmol), 2,4-dioxo-1,2,3,4-tetrahydropyrimidine-5-carboxylic acid monohydrate (35 mg, 0.20 mmol), triethylamine (70 µL, 0.50 mmol), and HATU (114 mg, 0.30 mmol) were reacted. To the reaction solution, a 2 N solution of ammonia in methanol was added to terminate the reaction, and then the reaction solution was concentrated under reduced pressure. The obtained residue was suspended in saturated aqueous sodium hydrogen carbonate, and the suspension was extracted three times with a 5:1 mixed solution of chloroform and methanol. The combined organic layers were dried over anhydrous sodium sulfate, the insoluble substance was separated by filtration, and then the filtrate was concentrated under reduced pressure. The obtained residue was subjected to preparative TLC using methanol containing 10% concentrated aqueous ammonia and chloroform (concentration, 25%) as the developing solvent to obtain the title compound (16 mg, 35%) as white solid.

Example 13

Synthesis of 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-4(1H)-one

[Formula 22]

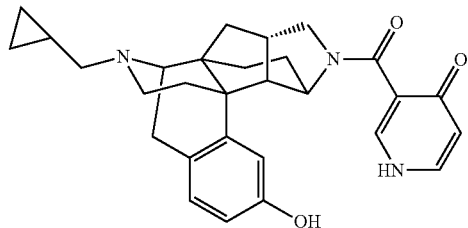

In the same manner as that of Example 1, (1S,3aR,5aS, 6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (32 mg, 90 µmol), 4-oxo-1,4-dihydropyridine-3-carboxylic acid (28 mg, 0.20 mmol), triethylamine (70 µL, 0.50 mmol), and HATU (114 mg, 0.30 mmol) were reacted. To the reaction solution, a 2 N solution of ammonia in methanol was added to terminate the reaction, then the reaction solution was suspended in saturated aqueous sodium hydrogen carbonate, and the suspension was extracted three times with ethyl acetate. The combined organic layer was dried over anhydrous sodium sulfate, the insoluble substance was separated by filtration, and then the filtrate was concentrated under reduced pressure. The obtained residue was subjected to preparative TLC using methanol containing 10% concentrated aqueous ammonia and chloroform (concentration, 15%) as the developing solvent to obtain the title compound (19 mg, 44%) as white solid.

Example 14

Synthesis of 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-4(1H)-one

[Formula 23]

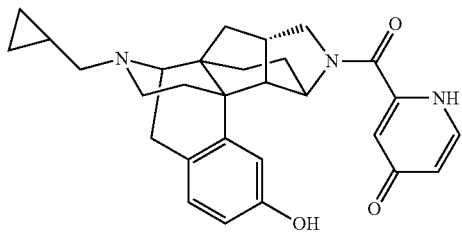

In the same manner as that of Example 1, (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (32 mg, 90 μmol), 4-oxo-1,4-dihydropyridine-2-carboxylic acid (28 mg, 0.20 mmol), triethylamine (70 μL, 0.50 mmol), and HATU (114 mg, 0.30 mmol) were reacted. To the reaction solution, a 2 N solution of ammonia in methanol was added to terminate the reaction, then the reaction solution was suspended in saturated aqueous sodium hydrogen carbonate, and the suspension was extracted three times with a 5:1 mixed solution of chloroform and methanol. The combined organic layer was dried over anhydrous sodium sulfate, the insoluble substance was separated by filtration, and then the filtrate was concentrated under reduced pressure. The obtained residue was subjected to preparative TLC using methanol containing 10% concentrated aqueous ammonia and chloroform (concentration, 15%) as the developing solvent to obtain the title compound (8 mg, 20%) as white solid.

Example 15

Synthesis of 4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one

[Formula 24]

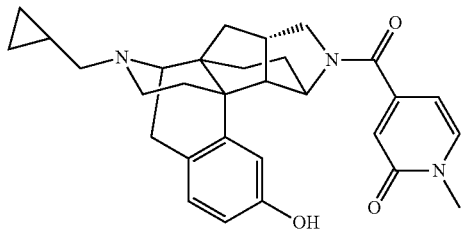

In the same manner as that of Example 1, (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (32 mg, 90 μmol), 1-methyl-2-oxo-1,2-dihydropyridine-4-carboxylic acid (31 mg, 0.20 mmol), triethylamine (70 μL, 0.50 mmol), and HATU (114 mg, 0.30 mmol) were reacted. To the reaction solution, a 2 N solution of ammonia in methanol was added to terminate the reaction, then the reaction solution was suspended in saturated aqueous sodium hydrogen carbonate, and the suspension was extracted three times with chloroform. The combined organic layers were dried over anhydrous sodium sulfate, the insoluble substance was separated by filtration, and then the filtrate was concentrated under reduced pressure. The obtained residue was subjected to preparative TLC using methanol and chloroform (concentration, 5%) as the developing solvent to obtain the title compound (41 mg, 94%) as white solid.

Example 16

Synthesis of 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridazin-3(2H)-one

[Formula 25]

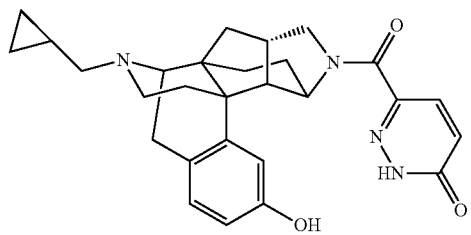

In the same manner as that of Example 1, (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (30 mg, 85.9 μmol), 6-oxo-1,6-dihydropyridazine-3-carboxylic acid (31 mg, 0.22 mmol), triethylamine (70 μL, 0.50 mmol), and HATU (129 mg, 0.34 mmol) were reacted. To the reaction solution, a 2 N solution of ammonia in methanol was added to terminate the reaction, and then the reaction solution was concentrated under reduced pressure. The residue was suspended in 6% aqueous ammonia, then the suspension was extracted with ethyl acetate, and the organic layer was dried over anhydrous magnesium sulfate. The insoluble substance was separated by filtration, and then the filtrate was concentrated under reduced pressure. The obtained residue was subjected to column chromatography (aminosilica gel, 16 g) using methanol and chloroform (concentration gradient, 0 to 30%) as the elution solvent to obtain the title compound (27 mg, 66%) as white solid.

Example 17

Synthesis of 4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)quinolin-2(1H)-one

[Formula 26]

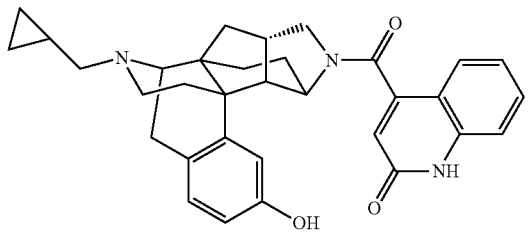

In the same manner as that of Example 1, (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (33 mg, 95 μmol), 2-oxo-1,2-dihydroquinoline-4-carboxylic acid (50 mg, 0.26 mmol), triethylamine (70 μL, 0.50 mmol), and HATU (128 mg, 0.34 mmol) were reacted. To the reaction solution, a 2 N solution of ammonia in methanol was added to terminate the reaction, and then the reaction solution was concentrated under reduced pressure. The residue was suspended in 6% aqueous ammonia, then the suspension was extracted with ethyl acetate, and the organic layer was dried over anhydrous magnesium sulfate. The insoluble substance was separated by filtration, and then the filtrate was concentrated under reduced pressure. The obtained residue was subjected to column chromatography (aminosilica gel, 16 g) using methanol and chloroform (concentration gradient, 0 to 30%) as the elution solvent to obtain the title compound (28 mg, 56%) as white solid.

Example 18

Synthesis of 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-2H-pyran-2-one

[Formula 27]

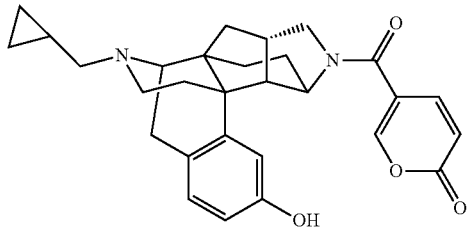

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (20 mg, 57 mol), 2-oxo-2H-pyran-5-carboxylic acid (18 mg, 0.13 mmol), diisopropylethylamine (50 μL, 0.29 mmol), and HATU (48 mg, 0.13 mmol) were reacted in the same manner as that of Example 1, except that dichloromethane was used as the solvent instead of THF and DMA. One hour after the start of the reaction, 1 N hydrochloric acid was added to the reaction solution, and the resulting mixture was further stirred. To the reaction solution, aqueous potassium carbonate was added to terminate the reaction, and then the reaction solution was extracted with chloroform. The organic layer was dried over sodium sulfate, the insoluble substance was separated by filtration, and then the filtrate was concentrated under reduced pressure. The obtained residue was subjected to preparative TLC using methanol and chloroform (concentration, 5%) as the developing solvent to obtain the title compound (4.0 mg, 15%) as brown amorphous substance.

Example 19

Synthesis of 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-4H-pyran-4-one

[Formula 28]

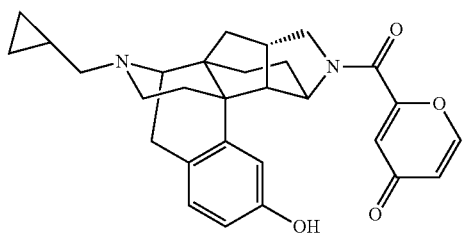

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (20 mg, 57 μmol), 4-oxo-4H-pyran-2-carboxylic acid (18 mg, 0.13 mmol), diisopropylethylamine (50 μL, 0.29 mmol), and HATU (48 mg, 0.13 mmol) were reacted in the same manner as that of Example 1, except that dichloromethane was used as the solvent instead of THF and DMA. To the reaction solution, a 2 N solution of methylamine in methanol (0.3 mL, 0.6 mmol) was added to terminate the reaction, and then the reaction solution was concentrated under reduced pressure. The residue was suspended in saturated aqueous sodium hydrogen carbonate, and then the suspension was extracted with chloroform. The organic layer was dried over anhydrous sodium sulfate, the insoluble substance was separated by filtration, and then the filtrate was concentrated under reduced pressure. The obtained residue was subjected to preparative TLC using methanol and chloroform (concentration, 10%) as the developing solvent to obtain the title compound (4.4 mg, 16%) as brown amorphous substance.

Example 20

Synthesis of 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-4(1H)-one

[Formula 29]

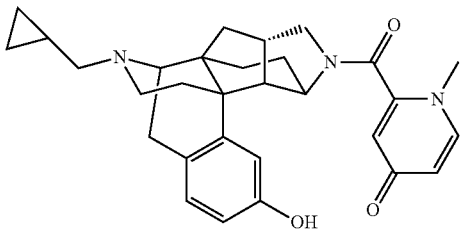

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (20 mg, 57 mol), 4-oxo-4H-pyran-2-carboxylic acid (18 mg, 0.13 mmol), diisopropylethylamine (50 μL, 0.29 mmol), and HATU (48 mg, 0.13 mmol) were reacted in the same manner as that of Example 1, except that dichloromethane was used as the solvent instead of THF and DMA. To the reaction solution, a 2 N solution of methylamine in methanol (3.0 mL, 6.0 mmol) was added to terminate the reaction, and then the reaction solution was concentrated under reduced pressure. The residue was suspended in saturated aqueous potassium carbonate, and then the suspension was extracted with chloroform. The organic layer was dried over anhydrous sodium sulfate, the insoluble substance was separated by filtration, and then the filtrate was concentrated under reduced pressure. The obtained residue was subjected to column chromatography (aminosilica gel, 8 g) using methanol and chloroform (concentration gradient, 0 to 10%) as the elution solvent to obtain the title compound (19 mg, 68%) as weakly brown amorphous substance.

Example 21

Synthesis of 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrazin-2(1H)-one

[Formula 30]

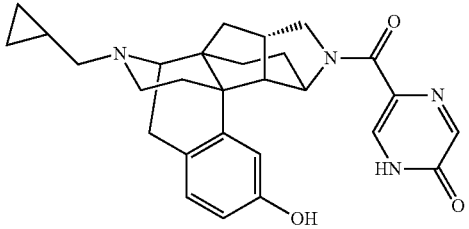

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (20 mg, 57 μmol), 5-oxo-4,5-dihydropyrazine-2-carboxylic acid (18 mg, 0.13 mmol), diisopropylethylamine (50 μL, 0.29 mmol), and HATU (48 mg, 0.13 mmol) were reacted in the same manner as that of Example 1, except that dichloromethane was used as the solvent instead of THF and DMA. To the reaction solution, a 1.4 N solution of ammonia in methanol was added to terminate the reaction, and then the reaction solution was concentrated under reduced pressure. The residue was suspended in aqueous potassium carbonate, and then the suspension was extracted with chloroform. The organic layer was dried over anhydrous sodium sulfate, the insoluble substance was separated by filtration, and then the filtrate was concentrated under reduced pressure. The obtained residue was subjected to column chromatography (silica gel, 10 g) using methanol and chloroform (concentration gradient, 5 to 30%) as the elution solvent to obtain the title compound (12.2 mg, 45%) as weakly brown amorphous substance.

Example 22

Synthesis of 2-((1S,3aR,5aS,6R,11bR,11cS)-10-acetoxy-14-(cyclopropylmethyl)-2,3,3a,4,5,6,7,11c-octahydro-1H-6,11b-(epiminoethano)-1,5a-methanonaphtho[1,2-e]indole-3-carbonyl)pyridine 1-oxide

[Formula 31]

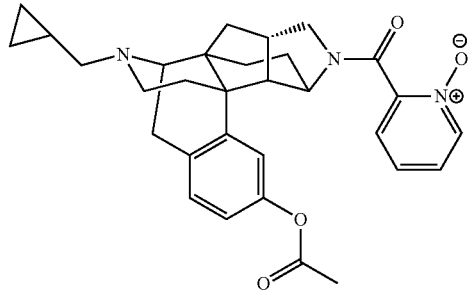

To a 10-mL test tube, 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide (52 mg, 0.11 mmol) synthesized in Example 1 was added, and suspended in THF (1 mL), then triethylamine (45 μL, 0.32 mmol) and acetyl chloride (15 μL, 0.21 mmol) were added to the suspension, and the resulting mixture was stirred at room temperature for 1 hour. Since it was confirmed that the starting material remained in the reaction solution, triethylamine (45 μL, 0.32 mmol) and acetyl chloride (15 μL, 0.21 mmol) were added again, and the resulting mixture was stirred at room temperature for 1 hour. To the reaction solution, saturated aqueous sodium hydrogen carbonate and ethyl acetate were added, the resulting mixture was vigorously stirred for 20 minutes, and then the aqueous layer was separated, and extracted with ethyl acetate. The combined organic layer was dried over anhydrous magnesium sulfate, then the insoluble substance was separated by filtration, and the filtrate was concentrated under reduced pressure to obtain the title compound (51 mg, 89%) as yellow amorphous substance.

Example 23

Synthesis of 6-((1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indole-3-carbonyl)pyridin-2(1H)-one

[Formula 32]

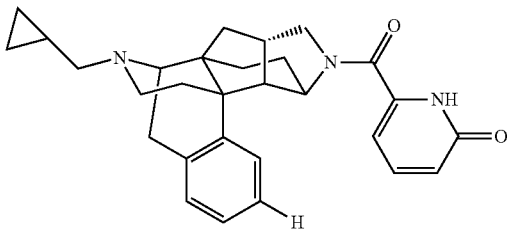

In the same manner as that of Example 1, (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indole (27 mg, 79 µmol) prepared according the method described in WO2013/035833 for the compound 297 (Example 228), 6-oxo-1,6-dihydropyridine-2-carboxylic acid (18 mg, 0.16 mmol), triethylamine (50 µL, 0.36 mmol), and HATU (70 mg, 0.18 mmol) were reacted. To the reaction solution, a 2 N solution of ammonia in methanol was added to terminate the reaction, and then the reaction solution was concentrated under reduced pressure. The residue was suspended in 6% aqueous ammonia, then the suspension was extracted with ethyl acetate, and the organic layer was dried over anhydrous magnesium sulfate. The insoluble substance was separated by filtration, and then the filtrate was concentrated under reduced pressure. The obtained residue was subjected to column chromatography (aminosilica gel, 8 g) using methanol and chloroform (concentration gradient, 0 to 20%) as the elution solvent. The obtained compound was dissolved in methanol, and powdered by adding tert-butyl methyl ether to the solution to obtain the title compound (24 mg, 67%) as white solid.

Reference Example 4

Synthesis of 3-oxo-3,4-dihydropyrazine-2-carboxylic Acid

[Formula 33]

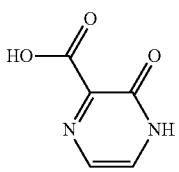

This compound was synthesized by the method described in WO2009/033084, and $^1$H NMR spectrum thereof coincided to the data described in Syn. Commun., 2010, 40(20), 2988-2999.

To a 50-mL round bottom flask, 3-aminopyrazine-2-carboxylic acid (300 mg, 2.17 mmol) and concentrated sulfuric acid (1.3 mL) were added. To the resulting mixture on an ice bath, sodium nitrite (149 mg, 2.16 mmol) dissolved in concentrated sulfuric acid (1.6 mL) was added dropwise, and then the resulting mixture was stirred for 1 hour. The reaction solution was added to ice water, the resulting mixture was vigorously stirred, and the produced solid was collected by filtration. The obtained solid was dried under reduced pressure at 60° C. for 1 hour to obtain the title compound (166 mg, 55%) as pale yellow crystals.

$^1$H NMR (DMSO-d$_6$, 400 MHz): δ 7.80 (d, 1H, J=3.7 Hz), 7.64 (d, 1H. J=3.7 Hz)

Example 24

Synthesis of 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrazin-2(1H)-one

[Formula 34]

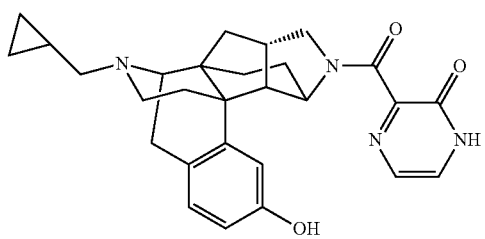

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (20 mg, 57 mol), and 3-oxo-3,4-dihydropyrazine-2-carboxylic acid (20 mg, 0.14 mmol) synthesized in Reference Example 4 were reacted in the same manner as that of Example 1, except that HOAt (17 mg, 0.13 mmol) was used instead of triethylamine. WSC (24 mg, 0.13 mmol) was used instead of HATU, and as the solvent, DMF was used instead of THF. To the reaction solution, a 1.4 N solution of ammonia in methanol was added to terminate the reaction, then the reaction solution was extracted with chloroform, and the organic layer was washed with saturated aqueous ammonium chloride, and then with saturated aqueous sodium hydrogen carbonate. The organic layer was dried over anhydrous sodium sulfate, the insoluble substance was separated by filtration, and then the filtrate was concentrated under reduced pressure. The obtained residue was subjected to preparative TLC using methanol and chloroform (concentration, 20%) as the developing solvent to obtain the title compound (5.9 mg, 22%) as pale yellow amorphous substance.

Example 25

Synthesis of 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrimidine-2,4(1H,3H)-dione

[Formula 35]

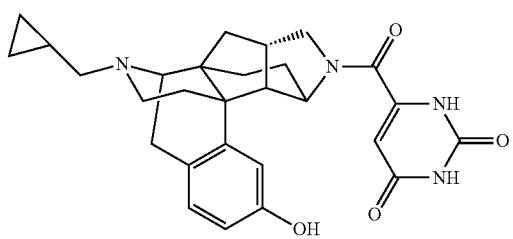

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (20 mg, 57 µmol), and 2,6-dioxo-1,2,3,6-tetrahydropyrimidine-4-carboxylic acid (20 mg, 0.13 mmol) were reacted in the same manner as that of Example 1, except that HOAt (17 mg, 0.13 mmol) was used instead of triethylamine. WSC (24 mg, 0.13 mmol) was used instead of HATU, and as the solvent, DMF was used instead of THF. To the reaction solution, a 1.4 N solution of ammonia in methanol was added to terminate the reaction, and then the reaction solution was concentrated under reduced pressure. The obtained residue was subjected to column chromatography (silica gel, 10 g) using methanol and chloroform (concentration gradient, 5 to 30%) as the elution solvent. In order to eliminate impurities, the obtained compound was suspended in chloroform and aqueous ammonia, and then collected by filtration to obtain the title compound (2.5 mg, 9%) as weakly brown amorphous substance.

Reference Example 5

Synthesis of 1-ethyl-6-oxo-1,6-dihydropyridine-2-carboxylic Acid

[Formula 36]

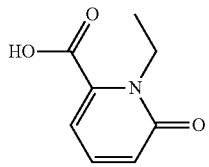

To a 30-mL round bottom flask, 6-oxo-1,6-dihydropyridine-2-carboxylic acid (129 mg, 925 µmol) and 1,1-diethoxy-N,N-dimethylmethaneamine (1.5 mL) were added, and the resulting mixture was stirred at 100° C. for 2 hours. The reaction solution was cooled to room temperature, and then concentrated under reduced pressure. The residue was subjected to column chromatography (silica gel, 10 g) using methanol and chloroform (concentration gradient, 0 to 20%) as the elution solvent to obtain ethyl 1-ethyl-6-oxo-1,6-dihydropyridine-2-carboxylate (104 mg, 58%) as colorless oily substance.

To a 50-mL round bottom flask, ethyl 1-ethyl-6-oxo-1,6-dihydropyridine-2-carboxylate (104 mg, 533 µmol) obtained above was added, and dissolved in ethanol (3 mL), then 5 N aqueous sodium hydroxide (200 µL, 1.0 mmol) was added to the solution, and the resulting mixture was stirred at 55° C. for 2 hours. The reaction solution was left to cool to room temperature, then made acidic with 5 N hydrochloric acid (400 µL, 2.0 mmol), and then concentrated under reduced pressure. Ethanol (3 mL) was added to the residue, and the resulting mixture was concentrated under reduced pressure. The residue was suspended in ethanol (3 mL), then the insoluble substance was separated by filtration, and the filtrate was concentrated under reduced pressure to obtain the title compound (48 mg, 54%) as colorless crystalline solid.

$^1$H NMR (DMSO-d$_6$, 400 MHz): δ 7.41 (dd, 1H, J=9.2, 6.0 Hz), 6.65 (d, 1H, J=6.4 Hz), 6.53 (d, 1H, J=8.7 Hz), 4.06 (q, 2H, J=6.9 Hz), 1.17 (t, 3H, J=6.9 Hz)

Example 26

Synthesis of 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-ethylpyridin-2(1H)-one

[Formula 37]

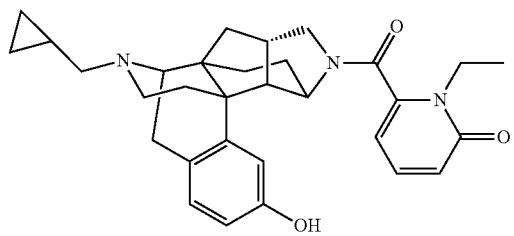

In the same manner as that of Example 1, (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (32 mg, 92 µmol), 1-ethyl-6-oxo-1,6-dihydropyridine-2-carboxylic acid (33 mg, 0.19 mmol) synthesized in Reference Example 5, triethylamine (70 µL, 0.50 mmol), and HATU (136 mg, 0.36 mmol) were reacted. To the reaction solution, a 2 N solution of ammonia in methanol was added to terminate the reaction, and then the reaction solution was concentrated under reduced pressure. The residue was suspended in 6% aqueous ammonia, then the suspension was extracted with ethyl acetate, and the organic layer was dried over anhydrous magnesium sulfate. The insoluble substance was separated by filtration, and then the filtrate was concentrated under reduced pressure. The obtained residue was subjected to column chromatography (aminosilica gel, 8 g) using methanol and chloroform (concentration gradient, 0 to 20%) as the elution solvent. The obtained compound was dissolved in methanol, and powdered by adding tert-butyl methyl ether to the solution to obtain the title compound (35 mg, 76%) as white solid.

Example 27

Synthesis of 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrimidin-4(3H)-one

[Formula 38]

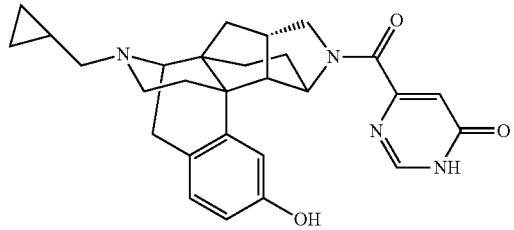

(1S,3aR,5aS,6R,11bR,11cS)-10-((tert-Butyldimethylsilyl)oxy)-14-(cyclopropylmethyl)-2,3,3a,4,5,6,7,11c-octahydro-1H-6,11b-(epiminoethano)-1,5a-methanonaphtho[1,2-e]indole (30 mg, 65 μmol), and 6-oxo-1,6-dihydropyrimidine-4-carboxylic acid (20 mg, 0.14 mmol) were reacted in the same manner as that of Example 1, except that HOAt (19 mg, 0.14 mmol) was used instead of triethylamine, WSC (27 mg, 0.14 mmol) was used instead of HATU, and as the solvent, DMF was used instead of THF. The residue was suspended in water, and then the suspension was extracted with ethyl acetate. The organic layer was dried over anhydrous sodium sulfate, the insoluble substance was separated by filtration, and then the filtrate was concentrated under reduced pressure. The obtained residue was subjected to column chromatography (silica gel, 10 g) using methanol and chloroform (concentration gradient, 0 to 10%) as the elution solvent.

To a 100-mL round bottom flask, the solid obtained above, methanol (2 mL), and aqueous ammonia were added, and the resulting mixture was stirred at room temperature for 3 days. The reaction solution was concentrated, and then the residue was suspended in chloroform. Then, the insoluble substance was separated by filtration, and the filtrate was concentrated under reduced pressure. The obtained residue was subjected to preparative TLC using methanol and chloroform (concentration, 20%) as the developing solvent to obtain the title compound (1.7 mg, 6%) as white amorphous substance.

Reference Example 6

Synthesis of 1-ethyl-6-oxo-1,6-dihydropyridine-3-carboxylic Acid

[Formula 39]

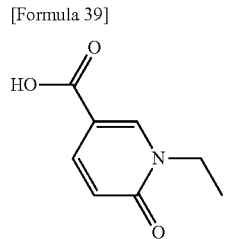

To 2-oxo-2H-pyran-5-carboxylic acid (200 mg, 1.43 mmol) and DMAP (17.5 mg, 143 μmol) dissolved in dichloromethane (3.3 mL) and THF (3.3 mL), WSC (274 mg, 1.43 mmol) and benzyl alcohol (148 μL, 1.43 mmol) were added, and the resulting mixture was stirred at room temperature for 2 hours. To the reaction solution, water was added, the insoluble substance was separated by filtration, and then the reaction solution was extracted with hexane. The organic layer was washed with saturated aqueous sodium hydrogen carbonate. The combined organic layer was dried over anhydrous sodium sulfate, then the insoluble substance was separated by filtration, and the filtrate was concentrated under reduced pressure. The obtained residue was dissolved in methanol (10 mL) together with ethylamine hydrochloride (112 mg, 1.37 mmol), and triethylamine (520 μL, 3.73 mmol) was added to the solution, followed by stirring the resulting mixture at room temperature for 16 hours. After the reaction, the reaction mixture was concentrated under reduced pressure, and saturated aqueous sodium hydrogen carbonate was added to the obtained residue. The resulting mixture was extracted with chloroform, and the organic layer was washed with saturated brine. The combined organic layers were dried over anhydrous sodium sulfate, then the insoluble substance was separated by filtration, and the filtrate was concentrated under reduced pressure. The residue was subjected to silica gel column chromatography (10 g) using ethyl acetate and hexane (concentration gradient, 10 to 60%) as the elution solvent to obtain benzyl 1-ethyl-6-oxo-1,6-dihydropyridine-3-carboxylate (126 mg, 34% for 2 steps) as pale yellow amorphous substance.

Benzyl 1-ethyl-6-oxo-1,6-dihydropyridine-3-carboxylate obtained above was dissolved in methanol (2 mL) and ethyl acetate (2 mL), and 10% palladium/carbon was added to the solution, followed by stirring the resulting mixture at room temperature for 2 hours under a hydrogen atmosphere. After the reaction, the insoluble substance was removed by filtration through Celite, and the obtained solution was concentrated to obtain the title compound (73 mg, 89%) as pale yellow amorphous substance.

1H NMR (CH$_3$OD, 400 MHz): δ 8.43 (d, 1H, J=2.3 Hz), 7.95 (dd, 1H, J=9.6, 2.3 Hz), 6.51 (d, 1H, J=9.6 Hz), 4.07 (q, 2H, J=7.3 Hz), 1.34 (t, 3H, J=7.3 Hz)

Example 28

Synthesis of 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-ethylpyridin-2(1H)-one

[Formula 40]

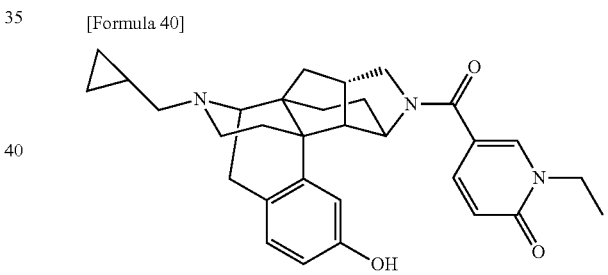

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (15 mg, 43 mol), 1-ethyl-6-oxo-1,6-dihydropyridine-3-carboxylic acid (16 mg, 94 μmol) synthesized in Reference Example 6, diisopropylethylamine (37 μL, 0.21 mmol), and HATU (36 mg, 94 μmol) were reacted in the same manner as that of Example 1, except that THF alone was used as the solvent. To the reaction solution, a 1.4 N solution of ammonia in methanol was added to terminate the reaction, and then the reaction solution was concentrated under reduced pressure. The residue was suspended in saturated aqueous sodium hydrogen carbonate, and then the suspension was extracted with chloroform. The organic layer was dried over anhydrous sodium sulfate, the insoluble substance was separated by filtration, and then the filtrate was concentrated under reduced pressure. The obtained residue was subjected to column chromatography (silica gel, 10 g) using methanol and chloroform (concentration gradient, 0 to 30%) as the elution solvent to obtain the title compound (13.3 mg, 62%) as white amorphous substance.

Example 29

Synthesis of 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide Hydrochloride

[Formula 41]

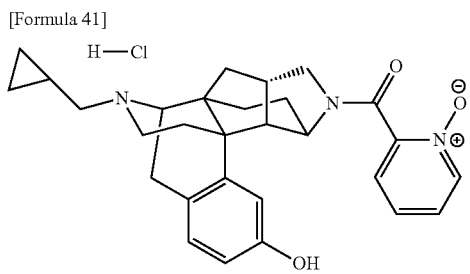

To a 50-mL round bottom flask, 2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide (79 mg, 0.17 mmol) synthesized in Example 1 was added, and dissolved in ethanol (2 mL), then 2 N hydrochloric acid (1 mL) was added to the solution, and the obtained solution was concentrated under reduced pressure. The obtained residue was dried at 80° C. for 18 hours under reduced pressure to obtain the title compound (85 mg, 99%) as white amorphous substance.

Example 30

Synthesis of 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one Hydrochloride

[Formula 42]

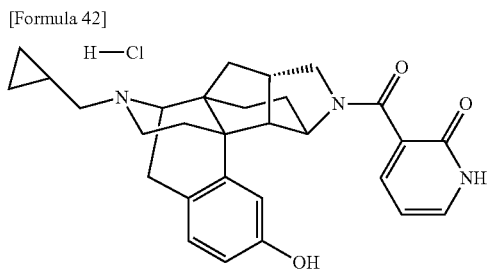

To a 50-mL round bottom flask, 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one (44 mg, 93 μmol) synthesized in Example 3 was added, and dissolved in 2 N hydrochloric acid (2 mL), and the obtained solution was concentrated under reduced pressure. The obtained residue was dried at 100° C. for 18 hours under reduced pressure to obtain the title compound (40 mg, 84%) as yellow solid.

Example 31

Synthesis of 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one Hydrochloride

[Formula 43]

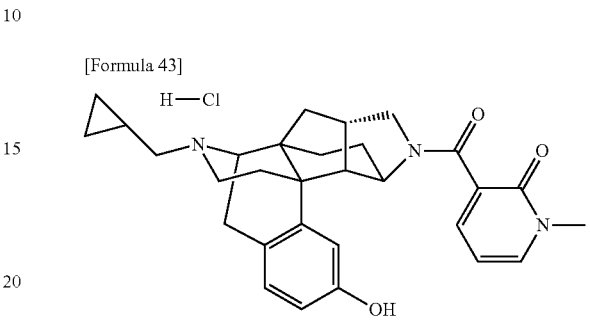

To a 10-mL test tube, 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphth[1,2-e]indole-3-carbonyl)-1-methylpyridin-2(1H)-one (26 mg, 54 μmol) synthesized in Example 6, and ethyl acetate were added. The resulting mixture was extracted with 1 N hydrochloric acid, and the aqueous layer was concentrated under reduced pressure. The obtained residue was dried at 60° C. for 1 hour under reduced pressure to obtain the title compound (23 mg, 83%) as pale yellow amorphous substance.

Example 32

Synthesis of 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-6-methylpyridin-2(1H)-one Hydrochloride

[Formula 44]

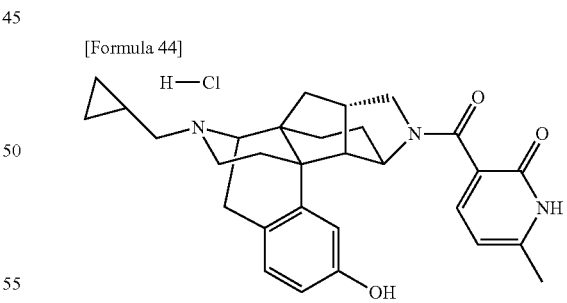

To a 10-mL test tube, 3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-6-methylpyridin-2(1H)-one synthesized in Example 8, and ethyl acetate were added. The resulting mixture was extracted with 1 N hydrochloric acid, and the aqueous layer was concentrated under reduced pressure. The obtained residue was dried under reduced pressure to obtain the title compound (11 mg, 39% for 2 steps from Example 8) as pale yellow amorphous substance.

Example 33

Synthesis of 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one Hydrochloride

[Formula 45]

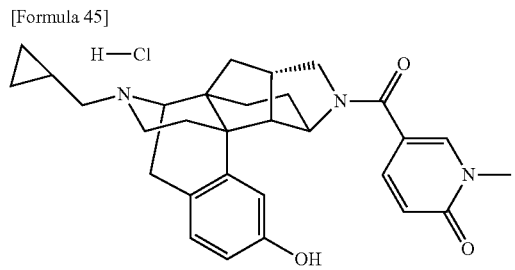

To a 10-mL test tube, 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one (31 mg, 64 μmol) synthesized in Example 9, and ethyl acetate were added. The resulting mixture was extracted with 1 N hydrochloric acid, and the aqueous layer was concentrated under reduced pressure. The obtained residue was dried at 60° C. for 2 hours under reduced pressure to obtain the title compound (22 mg, 67%) as pale yellow amorphous substance.

Example 34

Synthesis of 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one Hydrochloride

[Formula 46]

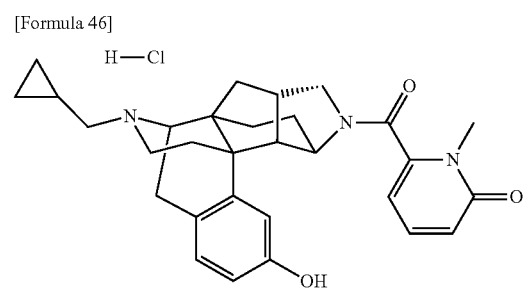

To a 10-mL test tube, 6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one (33 mg, 67 μmol) synthesized in Example 10, and ethyl acetate were added. The resulting mixture was extracted with 1 N hydrochloric acid, and the aqueous layer was concentrated under reduced pressure. The obtained residue was dried at 60° C. for 2 hours under reduced pressure to obtain the title compound (33 mg, 94%) as weakly brown amorphous substance.

TABLE 1

| Example | Deuterated solvent used for NMR measurement | NMR data | MS |
|---|---|---|---|
| 1 | DMSO-d6 | 9.07 (br s, 1H), 8.21-8.27 (m, 1H), 7.29-7.44 (m, 3H), 6.80-6.89 (m, 1H), 6.37-6.56 (m, 2H), 4.33 (br s, 0.5H), 3.86 (br s, 0.5H), 2.71-3.48 (m, 9H), 2.09-2.30 (m, 2H), 1.72-1.91 (m, 2H), 1.31-1.61 (m, 2H), 0.93-1.09 (m, 3H), 0.61-0.79 (m, 2H), 0.31-0.46 (m, 2H), −0.03-0.07 (m, 2H). | 472.21 M + H |
| 2 | CD3OD | 8.36 (d, 1.4H, J = 7.3 Hz), 8.32 (d, 0.6H, J = 7.3 Hz), 7.66 (d, 1.4H, J = 6.9 Hz), 7.54-7.58 (m, 0.6H), 6.96-7.05 (m, 1H), 6.53-6.69 (m, 2H), 4.66-4.70 (m, 0.7H), 4.15-4.20 (m, 0.3H), 3.43-3.81 (m, 2H), 3.01-3.32 (m, 7H), 1.95-2.05 (m, 2H), 1.77-1.86 (m, 2H), 1.55-1.67 (m, 2H), 1.43-1.50 (m, 3H), 0.88-1.00 (m, 2H), 0.52-0.65 (m, 2H), 0.17-0.31 (m, 2H). | 472.19 M + H |
| 3 | DMSO-d6 | 11.85 (br s, 0.6H), 11.80 (br s, 0.4H), 9.06 (br s, 1H), 7.34-7.42 (m, 2H), 6.89 (d, 0.7H, J = 8.2 Hz), 6.84 (d, 0.3H, 1= 7.8 Hz), 6.40-6.55 (m, 2H), 6.18 (t, 0.7H, J = 6.9 Hz), 6.13 (t, 0.3H, J = 6.9 Hz), 4.29-4.33 (m, 0.7H), 3.95-4.08 (m, 0.6H), 3.79-3.84 (m, 0.3H), 3.54-3.61 (m, 1H), 2.63-3.44 (m, 7.4H), 2.22-2.31 (m, 1H), 2.12-2.19 (m, 1H), 1.74-1.90 (m, 2H), 1.49-1.59 (m, 1H), 1.27-1.40 (m, 1.7H), 0.90-1.14 (m, 2.3H), 0.69-0.75 (m, 1H), 0.54-0.64 (m, 1H), 0.38-0.42 (m, 2H), −0.01-0.05 (m, 2H). | 472.19 M + H |
| 4 | CD3OD | 8.46-8.48 (m, 1H), 8.37 (d, 0.7H, J = 7.3 Hz), 8.33 (d, 0.3H, J = 6.9 Hz), 7.53-7.71 (m, 2H), 6.92-7.02 (m, 1H), 6.52-6.68 (m, 2H), 4.64-4.69 (m, 0.6H), 4.11-4.19 (m, 0.6H), 3.59-3.64 (m, 1H), 3.43-3.46 (m, 0.4H), 2.92-3.39 (m, 7.4H), 1.96-2.08 (m, 2H), 1.07-1.85 (m, 7H), 0.82-0.97 (m, 2H), 0.46-0.65 (m, 2H), 0,10-0.30 (m, 2H). | 472.18 M + H |
| 5 | DMSO-d6 | 11.70 (br s, 1H), 9.03 (br s, 1H),7.47-7.67 (m, 2H), 6.87-6.89 (m, 1H), 6.47-6.54 (m, 2H), 6.26-6.28 (m, 1H), 3.63-4.53 (m, 3H), 3.16 (t, 1H, J = 12.8 Hz), 2.95-3.02 (m, 2.5H), 2.75-2.82 (m, 2.5H), 2.46-2.52 (m, 1H), 2.28 (dd, 1H, J = 12.8, 5.5 Hz), 2.16 (dd, 1H, J = 12.8, 6.4 Hz), 1.74-1.91 (m, 2H), 1.39-1.60 (m, 2H), 1.11-1.20 (m, 2H), 0.94-0.99 (m, 1H), 0.66-0.77 (m, 2H), 0.35-0.42 (m, 2H), −0.02-0.06 (m, 2H). | 472.19 M + H |
| 6 | CDCl3 | 7.49 (dd, 0.7H, J = 6.9, 1.8 Hz), 7.46 (dd, 0.3H, J = 6.9, 1.8 Hz), 7.33-7.39 (m, 1H), 6.89 (d, 0.7H, J = 8.2 Hz), 6.89 (d, 0.3H, J = 8.2 Hz), 6.58-6.74 (m, 2H), 6.22 (t, 0.7H, J = 6.9 Hz), 6.20 (t 0.3H, J = 6.9 Hz), 4.62-4.72 (m, 0.7H), 4.11-4.21 (m, 0.6H), 3.67-3.80 (m, 1H), 3.59 (s, 2.1H), 3.55 (s, 0.9H), 3.48-3.61 (m, 1H), 3.22-3.36 (m, 1H), 2.72-3.19 (m, 5H), 2.47-2.64 (m, 0.7H), 2.21-2.42 (m, 1.7H), 1.80-2.13 (m, 1.7H), 1.35-1.77 (m, 2.4H), 0.95-1.34 (m, 3.2H), 0.73-0.94 (m, 2H), 0.36-0.55 (m, 2H), 0.01-0.19 (m, 2H). | |
| 7 | CD3OD | 7.61 (dd, 0.7H, J = 8.7, 6.9 Hz), 7.53 (dd, 0.3H, J = 9.2, 6.9 Hz), 6.95 (d, 0.7H, J = 8.2 Hz), 6.91 (d, 0.3H, J = 9.2 Hz), 6.46-6.63 (m, 4H), 4.62 (t, 0.7H, J = 6.9 Hz), 4.31 (t, 0.3H, J = 6.9 Hz), 4.08 (m, 0.3H), 3.87 (m, 0.7H), 3.70 (d, 0.7H, J = 11.5 Hz), 3.59 (d, 0.3H, J = 12.4 Hz), 3.25-3.38 (m, 2H), 3.08-3.18 (m, 2H), 2.84-3.01 (m, 2H), 2.56 (dd, 1H, J = 11.5, 4.6 Hz), 2.28-2.34 (m, 2H), 1.89-2.09 (m, 2H), 1.67-1.48 (m, 1H), 1.40-1.57 (m, 2H), 1.06-1.26 (m, 2H), 0.77-0.95 (m, 2H), 0.41-0.50 (m, 2H), 0.05-0.13 (m, 2H). | 472.2 M + H |

TABLE 2

| Example | Deuterated solvent used for NMR measurement | NMR data | MS |
|---|---|---|---|
| 8 | CDCl3 | 12.15 (br s, 1H), 8.20 (br s, 1H), 7.54 (d, 0.5H, J = 5.0 Hz), 7.53 (d, 0.5H, J = 5.0 Hz), 6.83-6.94 (m, 1H), 6.72 (d, 0.5H, J = 2.3 Hz), 6.51-6.63 (m, 1.5H), 6.13 (d, 0.5H, J = 7.3 Hz), 6.07 (d, 0.5H, J = 6.9 Hz), 4.57-4.68 (m, 0.5H), 4.14-4.33 (m, 1H), 3.71-3.85 (m, 1H), 3.46-3.60 (m, 0.5H), 3.20-3.34 (m, 1H), 2.66-3.17 (m, 5H), 2.45-2.60 (m, 1H), 0.69-2.42 (m, 14H), 0.38-0.52 (m, 2H), 0.02-0.14 (m, 2H). | |
| 9 | CDCl3 | 7.85 (s, 0.7H), 7.69 (s, 0.3H), 7.61 (d, 0.7H, J = 8.2 Hz), 7.44 (d, 0.3H, J = 8.7 Hz), 6.85-6.98 (m, 1H), 6.47-6.67 (m, 3H), 4.56-4.78 (m, 0.7H), 4.10-4.36 (m, 0.6H), 3.65-3.87 (m, 2H), 3.59 (s, 2.1H), 3.55 (s, 0.9H), 3.25-3.45 (m, 1H), 2.67-3.21 (m, 5H), 2.48-2.65 (m, 0.7H), 2.20-2.43 (m, 1.7H), 1.64-2.12 (m, 2.8H), 0.72-1.50 (m, 6.5H), 0.38-0.56 (m, 2H), 0.03-0.19 (m, 2H). | |
| 10 | DMSO-d6 | 9.09 (s, 0.7H), 9.07 (s, 0.3H), 7.43 (dd, 0.7H, J = 9.2, 6.9 Hz), 7.31-7.40 (m, 0.3H), 6.93 (d, 0.7H, J = 8.7 Hz), 6.87 (d, 0.3H, J =7.8 Hz), 6.20-6.61 (m, 4H), 3.57-4.49 (m, 2H), 3.32 (s, 0.9H), 3.29 (s, 2.1H), 2.44-3.48 (m, 8H), 2.25-2.34 (m, 1H), 2.14-2.23 (m, 1H), 1.74-1.99 (m, 2H), 1.53-1.68 (m, 1H), 1.30-1.50 (m, 2H), 0.95-1.25 (m, 2H), 0.62-0.81 (m, 2H), 0.36-0.48 (m, 2H), 0.06-0.10 (m, 2H). | 486.21 M + H |
| 11 | DMSO-d6 | 11.70 (br s, 1H), 9.07 (s, 1H), 7.42 (d, 0.6H, J = 6.4 Hz), 7.37 (d, 0.4H, J = 6.0 Hz), 6.93 (d, 0.6H, J = 8.2 Hz), 6.88 (d, 0.4H, J = 8.2 Hz), 6.45-6.58 (m, 2H), 6.30 (s, 0.6H), 6.24 (s, 0.4H), 6.13 (d, 0.6H, J = 6.9 Hz), 6.08 (d, 0.4H, J = 6.4 Hz), 4.39-4.43 (m, 0.6H), 4.04-4.07 (m, 0.4H), 3.94-3.89 (m, 0.4H), 3.60-3.65 (m, 0.6H), 2.98-3.48 (m, 5H), 2.46-2.91 (m, 3H), 2.26-2.34 (m, 1H), 2.16-2.22 (m, 1H), 1.75-1.94 (m, 2H), 1.11-1.63 (m, 4H), 0.96-1.03 (m, 1H), 0.66-0.78 (m, 2H), 0.41-0.43 (m, 2H), 0.03-0.10 (m, 2H). | 472.22 M + H |
| 12 | CD3OD | 7.64 (s, 1H), 6.96 (d, 0.8H, J = 8.7 Hz), 6.93 (d, 0.2H, J = 8.3 Hz), 6.51-6.67 (m, 2H), 2.81-5.14 (m, 10H), 2.51-2.62 (m, 1H), 2.29-2.39 (m, 2H), 1.87-2.15 (m, 2H), 1.66.1.80 (m, 0.8H), 1.38-1.60 (m, 1.2H), 1.05-1.32 (m, 3H), 0.74-0.95 (m, 1H), 0.40-0.56 (m, 2H), 0.03-0.20 (m, 2H). | 489.19 M + H |
| 13 | DMSO-d6 | 11.45-11.66 (m, 1H), 9.00-9.19 (m, 1H), 7.48-7.78 (m, 2H), 6.92 (d, 0.7H, J = 8.7 Hz), 6.87 (d, 0.3H, J = 8.3 Hz), 6.39-6.64 (m, 2H), 6.15 (d, 0.7H, J = 7.3 Hz), 6.12 (d, 0.3H, J = 6.9 Hz), 4.25-4.40 (m, 0.7H), 3.97-4.09 (m, 0.3H), 2.41-3.92 (m, 9H), 2.10-2.37 (m, 2H), 1.73-2.00 (m, 2H), 0.53-1.69 (m, 7H), 0.34-0.50 (m, 2H), –0.04-0.15 (m, 2H). | 472.22 M + H |
| 14 | DMSO-d6 | 10.84 (br s, 1H), 9.10 (s, 0.7H), 9.05 (s, 0.3H), 8.08-8.39 (m, 1H), 6.39-7.05 (m, 5H), 4.45-4.65 (m, 1H), 3.68-4.00 (m, 1H), 2.44-3.61 (m, 8H), 2.12-2.37 (m, 2H), 1.74-2.01 (m, 2H), 0.58-1.69 (m, 7H), 0.35-0.50 (m, 2H), 0.00-0.14 (m, 2H). | 472.22 M + H |

TABLE 3

| Example | Deuterated solvent used for NMR measurement | NMR data | MS |
|---|---|---|---|
| 15 | CDCl3 | 7.30-7.40 (m, 1H), 6.89-6.99 (m, 1H), 6.52-6.69 (m, 3H), 6.18-6.26 (m, 1H), 4.60-4.73 (m, 0.5H), 4.09-4.33 (m, 1H), 3.67-3.78 (m, 0.5H), 3.49-3.61 (m, 4H), 3.26-3.44 (m, 0.5H), 2.71-3.18 (m, 4.5H), 0.71-2.66 (m, 13H), 0.39-0.56 (m, 2H), 0.04-0.17 (m, 2H). | 486.23 M + H |
| 16 | DMSO-d6 | 9.07 (br s, 0.7H), 9.05 (br s, 0.3H), 7.61-7.68 (m, 1H), 6.87-6.93 (m, 2H), 6.48-6.60 (m, 2H), 4.56-4.59 (m, 0.3H), 4.48-4.52 (m, 0.7H), 4.06 (q, 0.3H, J = 5.0 Hz), 3.95-4.02 (m, 1H), 3.82-3.84 (m, 0.7H), 2.50-3.52 (m, 7H), 2.27-2.33 (m, 1H), 2.17-2.22 (m, 1H), 1.80-1.94 (m, 2H), 1.58-1.64 (m, 1H), 0.98-1.41 (m, 5H), 0.69-0.78 (m, 1H), 0.41-0.43 (m, 2H), 0.02-0.09 (m, 2H). | 473.22 M + H |
| 17 | DMSO-d6 | 9.11 (br s, 1H), 7.50-7.59 (m, 1H), 7.30-7.36 (m, 2H), 7.20-7.23 (m, 1H), 6.94 (d, 0.7H, J = 8.2 Hz), 6.83 (d, 0.3H, J =7.3 Hz), 6.38-6.62 (m, 3H), 4.50-4.57 (m, 1H), 3.40-3.62 (m, 4H), 3.14-3.24 (m, 1H), 2.74-3.03 (m, 4H), 2.52-2.56 (m, 1H), 2.25-2.35 (m, 1H), 2.15-2.22 (m, 1H), 1.77-1.95 (m, 2H), 1.41-1.55 (m, 2H), 0.95-1.06 (m, 2H), 0.70-0.81 (m, 2H), 0.38-0.44 (m, 2H), 0.02-0.09 (m, 2H). | 522.26 M + H |
| 18 | CD3OD | 7.89-8.12 (m, 2H), 6.99 (d, 0.2H, J = 7.8 Hz), 6.97 (d, 0.8H, J = 8.2 Hz), 6.64 (d, 0.2H, J = 2.8 Hz), 6.60-6.62 (m, 1.8H), 5.61 (d, 0.8H, J = 9.6 Hz), 5.57 (d, 0.2H, J = 9.2 Hz), 3.23-5.24 (m, 5H), 3.11-3.22 (m, 2H), 2.85-3.00 (m, 2H), 2.54-2.63 (m, 1H), 2.27-2.40 (m, 2H), 1.93-2.21 (m, 2H), 1.44-1.87 (m, 2H), 0.74-1.41 (m, 5H), 0.42-0.52 (m, 2H), 0.06-0.18 (m, 2H). | 471.22 M − H |
| 19 | DMSO-d6 | 9.10 (s, 0.7H), 9.07 (s, 0.3H), 8.20 (d, 0.7H, J = 6.0 Hz), 8.13 (d, 0.3H, J = 5.5 Hz), 6.87-6.97 (m, 1H) 6.45-6.73 (m, 3H), 6.40 (dd, 0.7H, J = 6.0, 2.3 Hz), 6.34 (dd, 0.3H, J = 5.5, 2.3 Hz), 4.24-4.51 (m, 1H), 3.87-4.01 (m, 1H), 2.38-3.81 (m, 8H), 2.14-2.35 (m, 2H), 1.73-1.98 (m, 2H), 1.53-1.66 (m, 1H), 1.35-1.49 (m, 1H), 0.63-1.31 (m, 5H), 0.34-0.50 (m, 2H), 0.03-0.14 (m, 2H). | 473.25 M + H |
| 20 | DMSO-d6 | 9.09 (s, 1H), 7.67 (d, 0.7H, J = 7.8 Hz), 7.63 (d, 0.3H, J = 7.3 Hz), 6.93 (d, 0.7H, J = 8.2 Hz), 6.88 (d, 0.3H, J = 8.2 Hz), 6.58 (d, 0.7H, J = 2.3 Hz), 6.49-6.55 (m, 1H), 6.46 (d, 0.3H, J = 8.2, 2.3 Hz), 6.07-6.14 (m, 1.7H), 6.05 (dd, 0.3H, J = 7.8, 2.8 Hz), 4.36-4.44 (m, 0.7H), 3.80-4.23 (m, 0.6H), 3.63-3.67 (m, 0.7H), 3.47 (s, 2.1H), 3.44 (s, 0.9H), 2.37-3.54 (m, 8H), 2.25-2.35 (m, 1H), 2.18 (dd, 1H, J = 12.4, 6.4 Hz), 1.73-1.96 (m, 2H), 1.53-1.67 (m, 1H), 1.30-1.51 (m, 2H), 1.11-1.19 (m, 2H), 0.95-1.08 (m, 1H), 0.61-0.81 (m, 2H), 0.35-0.48 (m, 2H), 0.01-0.11 (m, 2H). | 486.28 M + H |
| 21 | DMSO-d6 | 9.06-9.13 (m, 1H), 7.94 (s, 0.7H), 7.78-7.91 (m, 1.3H), 6.85-6.98 (m, 1H), 6.60 (s, 0.7H), 6.45-6.57 (m, 1.3H), 4.85-4.95 (m, 0.3H), 4.49-4.60 (m, 0.7H), 3.88-4.07 (m, 1.7H), 2.39-3.56 (m, 7.3H), 2.15-2.35 (m, 2H), 1.77-1.99 (m, 2H), 1.52-1.67 (m, 1H), 0.96-1.44 (m, 4H), 0.62-0.92 (m, 2H), 0.38-0.48 (m, 2H), 0.01-0.13 (m, 2H). | 473.25 M + H |

TABLE 4

| Example | Deuterated solvent used for NMR measurement | NMR data | MS |
|---|---|---|---|
| 22 | CDCl3 | 8.14-8.18 (m, 1H), 7.03-7.34 (m, 4H), 6.75-6.85 (m, 2H), 4.68 (m, 0.6H), 4.09-4.20 (m, 1H), 3.62-3.70 (m, 0.4H), 3.29-3.40 (m, 0.6H), 2.87-3.13 (m, 6.4H), 2.51-2.56 (m, 1H), 1.85-2.26 (m, 8H), 1.58-1.67 (m, 2H), 1.10-1.24 (m, 2H), 0.67-0.89 (m, 2H), 0.36-0.46 (m, 2H), 0.03-0.13 (m, 2H). | 514.27 M + H |
| 23 | CDCl3 | 7.05-7.43 (m, 5H), 6.27-6.68 (m, 2H), 4.81-4.84 (m, 0.7H), 4.50-4.53 (m, 0.3H), 4.27-4.36 (m, 0.3H), 4.10 (t, 0.7H, J = 11.0 Hz), 3.84 (d, 0.7H, J =3.8 Hz), 3.57-3.64 (m, 0.31-0, 3.34-3.48 (m, 1H), 2.78-3.20 (m, 5H), 2.54-2.61 (m, 1H), 2.26-2.36 (m, 2H), 1.87-2.05 (m, 2H), 1.15-1.78 (m, 5H), 0.75-0.93 (m, 2H), 0.47 (d, 2H, J = 7.8 Hz), 0.06-0.13 (m, 2H). | 456.29 M + H |
| 24 | DMSO-d6 | 9.10 (s, 0.6H), 9.07 (s, 0.4H), 7.19-7.62 (m, 2H), 6.92 (d, 0.6H, J = 8.7 Hz), 6.87 (d, 0.4H, J = 9.2 Hz), 6.66-6.36 (m, 2H), 4.33-4.40 (m, 0.6H), 3.91-3.99 (m, 0.4H), 3.85 (dd, 0.4H, J =12.8, 8.7 Hz), 3.59 (dd, 0.6H, J = 10.5, 8.2 Hz), 2.38-3.52 (m, 8H), 2.14-2.34 (m, 2H), 1.73-1.96 (m, 2H), 1.51-1.70 (m, 1H), 1.29-1.45 (m, 1H), 0.93-1.27 (m, 3H), 0.49-0.91 (m, 2H), 0.35-0.48 (m, 2H), −0.01-0.12 (m, 2H). | 473.27 M + H |
| 25 | DMSO-d6 | 8.96-9.68 (m, 2H), 6.91 (d, 0.6H, J = 8.2 Hz), 6.88 (d, 0.4H, J = 8.2 Hz), 6.58 (d, 0.6H, J = 2.3 Hz), 6.48-6.54 (m, 1H), 6.45 (dd, 0.4H, J = 8.2, 2.3 Hz), 4.88-5.19 (m, 1H), 4.35-4.44 (m, 0.4H), 4.28-4.35 (m, 0.6H), 3.70-3.82 (m, 1H), 2.39-3.61 (m, 8H), 2.24-2.34 (m, 1H), 2.14-2.23 (m, 1H), 1.73-1.99 (m, 2H), 1.48-1.66 (m, 1H), 0.92-1.45 (m, 4H), 0.56-0.82 (m, 2H), 0.33-0.50 (m, 2H), −0.02-0.14 (m, 2H). | 489.26 M + H |
| 26 | DMSO-d6 | 9.06 (br s, 0.7H), 9.05 (br s, 0.3H). 7.30-7.41 (m, 1H), 6.90 (d, 0.7H, J = 8.2 Hz), 6.84 (d, 0.3H, J = 8.2 Hz), 6.56 (br s, 1H), 6.50 (dd, 1H, J = 8.2, 2.3 Hz), 6.22-6.43 (m, 2H), 4.39 (br s, 1H), 3.52-4.14 (m, 4H), 2.90-3.21 (m, 4H), 2.70-2.79 (m, 2H), 2.42-2.50 (m, 1H), 2.13-2.29 (m, 2H), 1.72-1.95 (m, 3H), 1.53-1.63 (m, 1H), 1.27-1.39 (m, 1H), 0.94-1.18 (m, 5H), 0.57-0.80 (m, 2H), 0.38 (d, 2H, J = 7.8 Hz), 0.02 (br s, 2H). | 500.31 M + H |
| 27 | DMSO-d6 | 9.08 (s, 0.6H), 9.06 (s, 0.4H), 8.22 (s, 0.6H), 8.15 (s, 0.4H), 6.92 (d, 0.6H, J = 8.2 Hz), 6.88 (d, 0.4H, J = 7.8 Hz), 6.59 (d, 0.6H, J = 2.8 Hz), 6.52 (dd, 0.6H, J = 8.2, 2.8 Hz), 6.49 (d, 0.4H, J = 2.3 Hz), 6.46 (dd, 0.4H, J = 7.8, 2.3 Hz), 6.40 (s, 0.6H), 6.37 (s, 0.4H), 4.30-4.46 (m, 1H), 3.68-3.93 (m, 1H), 2.40-3.65 (m, 8H), 2.14-2.34 (m, 2H), 1.74-1.93 (m, 2H), 1.52-1.67 (m, 1H), 0.93-1.44 (m, 3H), 0.61-0.91 (m, 3H), 0.36-0.48 (m, 2H), 0.01-0.10 (m, 2H). | 473.28 M + H |
| 28 | CD3OD | 8.04 (s, 0.7H), 7.92 (s, 0.3H), 7.55-7.73 (m, 1H), 6.91-7.05 (m, 1H), 6.48-6.73 (m, 3H), 2.87-5.06 (m, 12H), 2.24-2.74 (m, 2H), 1.91-1.86 (m, 1H), 1.71-1.86 (m, 1H), 1.09-1.67 (m, 8H), 0.77-1.04 (m, 2H), 0.42-0.70 (m, 2H), 0.05-0.34 (m, 2H). | 500.31 M + H |

TABLE 5

| Example | Deuterated solvent used for NMR measurement | NMR data | MS |
|---|---|---|---|
| 29 | DMSO-d6 | 9.38 (br s, 1H), 8.91 (br s, 0.3H), 8.74 (br s, 0.7H), 8.25-8.29 (m, 1H), 7.35-7.51 (m, 3H), 7.02 (d, 0.7H, J = 8.2 Hz), 6.95 (d, 0.3H, J = 8.7 Hz), 6.65-6.70 (m, 1.3H), 6.50-6.57 (m, 0.7H), 4.40 (dd, 0.7H, J = 6.0, 2.3 Hz), 3.89-4.00 (m, 1.7H), 3.00-3.57 (m, 9.6H), 2.87-2.92 (m, 1H), 2.47-2.57 (m, 1H), 1.91-2.10 (m, 1H), 1.64-1.77 (m, 1H), 1.31-1.59 (m, 3H), 1.10 (br s, 1H), 0.48-0.69 (m, 4H), 0.33-0.39 (m, 1H). | 472.24 M + H |
| 30 | DMSO-d6 | 11.82-11.95 (m, 1H), 9.36 (br s, 1H), 9.00 (br s, 0.3H), 8.85 (br s, 0.7H), 7.35-7.47 (m, 2H), 6.98 (d 0.7H J = 7.3 Hz), 6.93 (d, 0.3H, J = 7.8 Hz), 6.46-6.67 (m, 2H), 6.12-6.21 (m, 1H), 4.29-4.37 (m, 0.7H), 3.96-4.04 (m, 1H), 3.81-3.87 (m, 0.3H), 2.84-3.63 (m, 12H), 1.89-2.00 (m, 1H), 1.59-1.71 (m, 1H), 1.43-1.54 (m, 1H), 1.27-1.38 (m, 2H), 0.96-1.13 (m, 5H). | 472.26 M + H |
| 31 | CD3OD | 7.68-7.89 (m, 1H), 7.50-7.66 (m, 1H), 7.12 (d, 0.7H, J = 8.7 Hz), 7.06 (d, 0.3H, J = 8.2 Hz), 6.61-6.78 (m, 2H), 6.45 (t, 0.7H, J = 6.9 Hz), 6.39 (t, 0.3H, J = 6.9 Hz), 3.62 (s, 2.1H), 3.60 (s, 0.9H), 3.09-5.35 (m, 10H), 2.86-3.08 (2H, m), 2.69-2.85 (m, 1H), 2.07-2.21 (m, 1H), 1.46-1.96 (m, 4.7H), 1.08-1.21 (m, 1.3H), 0.68-0.96 (m, 3H), 0.43-0.57 (m, 2H). | 486.21 M + H |
| 32 | CD3OD | 7.45-7.66 (m, 1H), 7.11 (d, 0.7H, J = 8.2 Hz), 7.06 (d, 0.3H, J = 8.7 Hz), 6.61-6.79 (m, 2H), 6.27 (d, 0.7H, J = 6.9 Hz), 6.21 (d, 0.3H, J = 7.3 Hz), 3.11-5.00 (m, 10H), 3.02 (dd, 1H, J = 13.3, 7.3 Hz), 2.69-2.94 (m, 2H), 2.34 (s, 2.1H), 2.30 (s, 0.9H), 2.05-2.20 (m, 1H), 1.46-1.92 (m, 4.7H), 1.06-1.21 (m, 1.3H), 0.70-0.95 (m, 3H), 0.42-0.55 (m, 2H). | 486.22 M + H |
| 33 | CD3OD | 8.06 (s, 0.8H), 7.94 (br s, 0.2H), 7.73 (d, 0.8H, J = 8.7 Hz), 7.56-7.66 (m, 0.2H), 7.02-7.17 (m, 1H), 6.48-6.82 (m, 3H), 3.09-4.98 (m, 13H), 3.03 (dd, 1H, J = 13.3, 7.3 Hz), 2.73-2.96 (m, 2H), 2.07-2.22 (m, 1H), 1.39-1.96 (m, 4.8H), 0.90-1.34 (m, 2.2H), 0.70-0.88 (m, 2H), 0.42-0.58 (m, 2H). | 486.21 M + H |
| 34 | CD3OD | 7.58 (dd, 0.7H, J = 9.2, 6.9 Hz), 7.46-7.54 (m, 0.3H), 7.13 (d, 0.7H, J = 8.2 Hz), 7.07 (d, 0.3H, J = 8.7 Hz), 6.55-6.84 (m, 3H), 6.38-6.51 (m, 1H), 3.26-5.26 (m, 13H), 2.89-3.11 (m, 2H), 2.70-2.86 (m, 1H), 2.07-2.22 (m, 1H), 1.83-2.01 (m, 1H), 1.33-1.77 (m, 4H), 1.09-1.21 (m, 1H), 0.71-1.04 (m, 3H), 0.43-0.57 (m, 2H). | 486.22 M + H |

Reference Example 7-1

Synthesis of 2,2,2-trichloroethyl (1S,3aR,5aS,6R, 11bR,11cS)-10-hydroxy-1,2,3a,4,5,6,7,11c-octahydro-3H-6,11b-(epiminoethano)-1,5a-methanonaphtho[1,2-e]indole-3-carboxylate

[Formula 47]

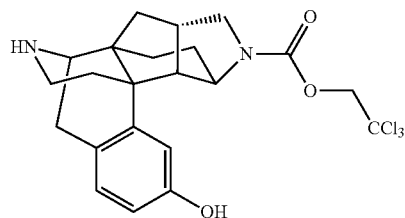

To a 100-mL recovery flask, 2,2,2-trichloroethyl (1S,3aR,5aS,6R,11bR,11cS)-10-methoxy-1,2,3a,4,5,6,7,11c-octahydro-3H-6,11b-(epiminoethano)-1,5a-methanonaphtho[1,2-e]indole-3-carboxylate (972.7 mg, 2.00 mmol) synthesized according to the method described in WO2014/136305, Example 34, (1) was added, and dissolved in methylene chloride (20 mL). The reaction solution was cooled to 0° C., then a 1 M solution of boron tribromide in methylene chloride (6 mL) was added to the reaction solution with vigorous stirring, and then the resulting mixture was stirred for 1 hour with warming to room temperature.

To the reaction solution, saturated aqueous sodium hydrogen carbonate (30 mL) was added, and then the resulting mixture was extracted with chloroform (20 mL×3). The combined organic layers were dried over anhydrous sodium sulfate, then the insoluble substance was separated by filtration, and the filtrate was concentrated under reduced pressure to obtain the title compound (1.04 g, >100%) as white foam-like substance. The crude product was used as it was for the following reaction without any further purification.

Reference Example 7-2

Synthesis of 2,2,2-trichloroethyl (1S,3aR,5aS,6R, 11bR,11cS)-10-hydroxy-14-(2,2,2-trifluoroacetyl)-1,2,3a,4,5,6,7,11c-octahydro-3H-6,11b-(epiminoethano)-1,5a-methanonaphtho[1,2-e]indole-3-carboxylate

[Formula 48]

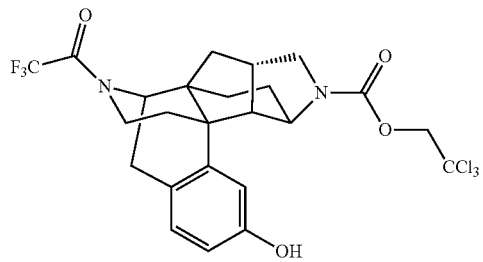

To a 100-mL recovery flask, 2,2,2-trichloroethyl (1S,3aR,5aS,6R,11bR,11cS)-10-hydroxy-1,2,3a,4,5,6,7,11c-octahydro-3H-6,11b-(epiminoethano)-1,5a-methanonaphtho[1,2-e]indole-3-carboxylate (1.04 g) synthesized in Reference Example 7-1 was added, and dissolved in THF (20 mL). To the obtained solution, triethylamine (2.79 mL, 20 mmol) and trifluoroacetic anhydride (1.41 mL, 10 mmol) were added, and the resulting mixture was stirred at room temperature for 1 hour. The reaction solution was concentrated under reduced pressure. The residue was diluted with saturated aqueous sodium hydrogen carbonate (50 mL), and then extracted with ethyl acetate (30 mL×2). The combined organic layer was dried over anhydrous sodium sulfate, then the insoluble substance was separated by filtration, and the filtrate was concentrated under reduced pressure to obtain the title compound (1.46 g, >100%) as white foam-like substance. The crude product was used as it was for the following reaction without any further purification.

Reference Example 7-3

Synthesis of 2,2,2-trifluoro-1-((1S,3aR,5aS,6R, 11bR,11cS)-10-hydroxy-2,3,3a,4,5,6,7,11c-octahydro-1H-6,11b-(epiminoethano)-1,5a-methanonaphtho[1,2-e]indol-14-yl)ethan-1-one

[Formula 49]

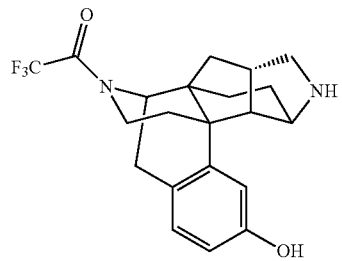

To a 100-mL recovery flask, 2,2,2-trichloroethyl (1S,3aR,5aS,6R,11bR,11cS)-10-hydroxy-14-(2,2,2-trifluoroacetyl)-1,2,3a,4,5,6,7,11c-octahydro-3H-6,11b-(epiminoethano)-1,5a-methanonaphtho[1,2-e]indole-3-carboxylate (1.46 g) synthesized in Reference Example 7-2 was added, and dissolved in acetic acid (25 mL). To the obtained solution, zinc powder (1.31 g, 20 mmol) was added, and the resulting mixture was stirred at room temperature for 2 hours. The reaction solution was filtered through Celite to remove excessive zinc powder. The filtrate was concentrated under reduced pressure, and then azeotroped with toluene. The residue was diluted with saturated aqueous sodium hydrogen carbonate (30 mL), and then extracted with chloroform (30 mL×3). The combined organic layers were dried over anhydrous sodium sulfate, then the insoluble substance was separated by filtration, and the filtrate was concentrated under reduced pressure. The obtained residue was subjected to column chromatography (aminosilica gel, 16 g) using ethyl acetate and methanol (concentration gradient, 0 to 30%) as the elution solvent to obtain the title compound (215 mg, total yield of 27% for 3 steps) as pale yellow foam-like substance. $^1$H NMR CDCl$_3$: 6.96-7.06 (m, 1H), 6.64-6.72 (m, 1H), 6.52-6.58 (m, 1H), 5.90 (br s, 1H), 4.90 (d, 0.5H, J=6.8 Hz), 4.34 (dd, 0.5H, J=6.5, 13.8 Hz), 4.18-4.24 (m, 0.5H), 2.72-3.81 (m, 8.5H), 2.21-2.45 (m, 1H), 1.46-2.00 (m, 3H), 0.99-1.43 (m, 4H)

Reference Example 8-1

Synthesis of ethyl 3-oxo-2,3-dihydro-1H-pyrazole-4-carboxylate

[Formula 50]

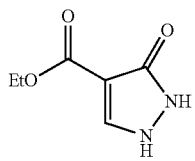

This compound was synthesized according to the method described in WO2011/090935.

To a 500-mL recovery flask, a 20% solution of sodium ethoxide in ethanol (60 mL) and ethyl 2-(ethoxymethylene)malonate (10.5 mL, 524 mmol) were added, and the resulting mixture was stirred at room temperature for 10 minutes. To the obtained mixture, hydrazine monohydrate (5.1 mL, 104 mmol) was added, the resulting mixture was stirred at 80° C. for 18 hours with heating, and then the obtained yellow suspension was cooled to 0° C. To the reaction solution vigorously stirred, 1 N hydrochloric acid (180 mL) was slowly added to the mixture at the same temperature to obtain a yellow solution. To the obtained solution, ethyl acetate (150 mL) was added, and the resulting mixture was stirred at room temperature for 1 hour. The organic layer was separated, and then the aqueous layer was extracted with ethyl acetate (100 mL×2). The combined organic layers were dried over anhydrous sodium sulfate, and the insoluble substance was separated by filtration. The filtrate was concentrated under reduced pressure, and the obtained residue was crystallized by using ethyl acetate and hexane to obtain the title compound (2.82 g, 35%) as yellow crystals (mixture of tautomers). MS ES M−H=155

Reference Example 8-2

Synthesis of 3-methoxy-1-methyl-1H-pyrazole-4-carboxylic Acid

[Formula 51]

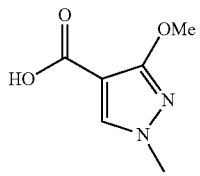

To a 50-mL round bottom flask, ethyl 3-oxo-2,3-dihydro-1H-pyrazole-4-carboxylate (200 mg, 1.28 mmol), iodomethane (397 μL, 6.40 mmol), and DMF (5 mL) were added, sodium hydride (60%, dispersed in liquid paraffin, 256 mg, 6.40 mmol) was added to the mixture, and the resulting mixture was stirred at room temperature for 22 hours. Under ice cooling, water was added to the reaction solution, and the resulting mixture was extracted three times with ethyl acetate. The combined organic layers were dried over anhydrous sodium sulfate, then the insoluble substance was separated by filtration, and the filtrate was concentrated under reduced pressure. The residue was subjected to silica gel column chromatography (25 g) using ethyl acetate and hexane (concentration gradient, 5 to 60%) as the elution solvent to obtain ethyl 3-methoxy-1-methyl-1H-pyrazole-4-carboxylate (51 mg, 22%) as white solid.

To a 50-mL round bottom flask, ethyl 3-methoxy-1-methyl-1H-pyrazole-4-carboxylate (51 mg, 0.279 mmol) obtained above was added, and dissolved in ethanol (1 mL), then 5 N aqueous sodium hydroxide (0.5 mL, 2.50 mmol) was added to the solution, and the resulting mixture was stirred at room temperature for 3 days. To the reaction solution, a 1 N hydrochloric acid (2.7 mL) was added, and the resulting mixture was concentrated under reduced pressure. The obtained residue was dissolved in THF, the insoluble substance was separated by filtration using Celite, and the filtrate was concentrated under reduced pressure to obtain the title compound (43 mg, 100%) as white powder.

$^1$H NMR DMSO-$d_6$: 11.91 (br s, 1H), 7.99 (s, 1H), 3.80 (s, 3H), 3.69 (s, 3H)

Example 35

Synthesis of 6-((1S,3aR,5aS,6R,11bR,11cS)-10-hydroxy-2,3,3a,4,5,6,7,11c-octahydro-1H-6,10b-(epiminoethano)-1,5a-methanonaphtho[1,2-e]indole-3-carbonyl)pyridin-2(1H)-one

[Formula 52]

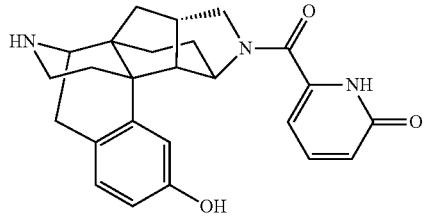

To a 10 m-L test tube, 2,2,2-trifluoro-1-((1S,3aR,5aS,6R,11bR,11cS)-10-hydroxy-2,3,3a,4,5,6,7,11c-octahydro-1H-6,11b-(epiminoethano)-1,5a-methanonaphtho[1,2-e]indol-14-yl)ethan-1-one (54 mg, 136 μmol) synthesized in Reference Example 7-3, 6-oxo-1,6-dihydropyridine-2-carboxylic acid (67 mg, 0.48 mmol), and HATU (197 mg, 0.52 mmol) were added, and suspended in THF (2 mL), then triethylamine (100 μL, 0.72 mmol) and DMA (100 μL) were added to the suspension, and the resulting mixture was stirred at room temperature for 1.5 hours.

To the reaction mixture, ethanolamine (100 μL) and methanol (2 mL) were added, and the resulting mixture was stirred at the same temperature for 1 hour. The reaction solution was concentrated under reduced pressure, the obtained residue was dissolved in chloroform (30 mL), and the solution was washed with 6% aqueous ammonia (10 mL×3). The combined aqueous layers were extracted with chloroform (20 mL). The combined organic layers were dried over anhydrous magnesium sulfate, the insoluble substance was separated by filtration, and then the filtrate was concentrated under reduced pressure. The obtained residue was subjected to column chromatography (amino-silica gel, 16 g) using methanol and chloroform (concentration gradient, 10 to 30%) as the elution solvent to obtain 6-((1S,3aR,5aS,6R,11bR,11cS)-10-hydroxy-14-(2,2,2-trifluoroacetyl)-2,3,3a,4,5,6,7,11c-octahydro-1H-6,11b-(epiminoethano)-1,5a-methanonaphtho[1,2-e]indole-3-carbonyl)pyridin-2(1H)-one (M+H=514.26) as white foam-like substance.

6-((1S,3aR,5aS,6R,11bR,11cS)-10-Hydroxy-14-(2,2,2-trifluoroacetyl)-2,3,3a,4,5,6,7,11c-octahydro-1H-6,11b-(epiminoethano)-1,5a-methanonaphtho[1,2-e]indole-3-carbonyl)pyridin-2(1H)-one obtained above was dissolved in methanol (5 mL) in a 100-mL recovery flask, sodium borohydride (124 mg, 3.26 mmol) was added to the solution, and the resulting mixture was stirred at room temperature for 2 hours. The reaction solution was concentrated under reduced pressure, the residue was suspended in 6% aqueous ammonia (20 mL), and the suspension was washed with chloroform (20 mL×2). The aqueous layer was concentrated under reduced pressure, and the residue was subjected to column chromatography (aminosilica gel, 12 g) using methanol and chloroform (concentration gradient, 10 to 30%) as the elution solvent, and thereby purified to obtain a mixture of 6-((1S,3aR,5aS,6R,11bR,11cS)-10-hydroxy-14-(2,2,2-trifluoroacetyl)-2,3,3a,4,5,6,7,11c-octahydro-1H-6,11b-(epiminoethano)-1,5a-methanonaphtho[1,2-e]indole-3-carbonyl)pyridin-2(1H)-one, and the title compound, 6-((1S,3aR,5aS,6R,11bR,11cS)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one.

The mixture obtained above was dissolved in concentrated aqueous ammonia (3 mL) in a 50-mL recovery flask, and the solution was heated at 80° C. for 18 hours in a tube sealed with a rubber stopper. The reaction mixture was concentrated under reduced pressure, and the residue was subjected to column chromatography (aminosilica gel, 7 g) using methanol and chloroform (concentration gradient, 10 to 50%) as the elution solvent. The obtained crude product was powdered by using methanol (0.2 mL) and t-butyl methyl ether (3 mL) to obtain the title compound (23 mg, 41%).

$^1$H NMR DMSO-$d_6$: 9.08 (s, 1H), 7.53 (dd, 0.7H, J=6.9, 8.7 Hz), 7.47 (dd, 0.3H, J=7.3, 9.2 Hz), 6.92 (d, 0.7H, J=8.2 Hz), 6.87 (d, 0.3H, J=7.8 Hz), 6.39-6.58 (m, 4H), 4.42-4.45 (m, 0.7H), 4.13-4.17 (m, 0.3H), 3.89-3.94 (m, 0.3H), 3.71-3.76 (m, 0.7H), 3.61 (d, 0.7H, J=11.0 Hz), 3.45-3.48 (m, 0.3H), 3.15-3.27 (m, 1H), 2.80-3.09 (m, 5H), 2.64-2.73 (m, 1H), 2.13-2.44 (m, 2H), 1.63-1.70 (m, 1H), 1.25-1.59 (m, 2H), 1.12-1.15 (d, 1H, J=11.0 Hz), 1.01-1.07 (m, 1H), 0.88-0.94 (m, 1H), 0.66-0.74 (m, 1H)

Example 36

Synthesis of 4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methyl-1,2-dihydro-3H-pyrazol-3-one

[Formula 53]

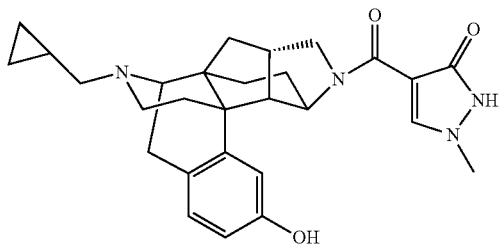

(1S,3aR,5aS,6R,11bR,11cS)-14-(Cyclopropylmethyl)-2,3,3a,4,5,6,7,11c-octahydro-1H-6,11b-(epiminoethano)-1,5a-methanonaphtho[1,2-e]indol-10-ol (30 mg, 86 μmol), 3-methoxy-1-methyl-1H-pyrazole-4-carboxylic acid (29 mg, 0.19 mmol), diisopropylethylamine (75 μL, 0.43 mmol), and HATU (72 mg, 0.19 mmol) were reacted in the same manner as that of Example 1, except that THF (2 mL) alone was used as the solvent. To the reaction solution, a 1.4 N solution of ammonia in methanol was added to terminate the reaction, and then the reaction solution was concentrated under reduced pressure. The residue was suspended in saturated aqueous sodium hydrogen carbonate, and then the suspension was extracted with chloroform. The organic layer was dried over anhydrous sodium sulfate, the insoluble substance was separated by filtration, and then the filtrate was concentrated under reduced pressure. The obtained residue was subjected to column chromatography (silica gel, 10 g) using methanol and ethyl acetate (concentration gradient, 0 to 30%) as the elution solvent, and thereby purified to obtain ((1S,3aR,5aS,6R,11bR,11cS)-14-(cyclopropylmethyl)-10-hydroxy-1,2,3a,4,5,6,7,11c-octahydro-3H-6,11b-(epiminoethano)-1,5a-methanonaphtho[1,2-e]indol-3-yl)(3-methoxy-1-methyl-1H-pyrazol-4-yl)methanone (33.3 mg, 80%) as pale yellow amorphous substance.

$^1$H NMR CD$_3$OD: 7.69 (s, 0.7H), 7.55 (s, 0.3H), 6.90-6.96 (m, 1H), 6.63 (d, 0.7H, J=2.8 Hz), 6.53-6.58 (m, 1.3H), 2.78-5.02 (m, 8H), 3.90 (s, 3H), 3.73 (a, 2.1H), 3.68 (s, 0.9H), 2.53-2.57 (m, 1H), 2.31-2.33 (m, 2H), 1.90-2.09 (m, 2H), 1.66-1.76 (m, 1H), 1.51-0.78 (m, 7H), 0.45-0.48 (m, 2H), 0.09-0.12 (m, 2H)

To a 30-mL round bottom flask, ((1S,3aR,5aS,6R,11bR,11cS)-14-(cyclopropylmethyl)-10-hydroxy-1,2,3a,4,5,6,7,11c-octahydro-3H-6,11b-(epiminoethano)-1,5a-methanonaphtho[1,2-e]indol-3-yl)(3-methoxy-1-methyl-1H-pyrazol-4-yl)methanone (15 mg, 31 μmol) obtained above was added, and dissolved in methylene chloride (1 mL). A 1.0 M solution of boron tribromide in methylene chloride (153 μL, 0.15 mmol) was added to the solution under ice cooling, and the resulting mixture was stirred at room temperature for 1 hour. A 1.4 N solution of ammonia in methanol was added to terminate the reaction, and then the reaction solution was concentrated under reduced pressure. The residue was suspended in saturated aqueous sodium hydrogen carbonate, and then the suspension was extracted with chloroform. The organic layer was dried over anhydrous sodium sulfate, the insoluble substance was separated by filtration, and then the filtrate was concentrated under reduced pressure. The obtained residue was subjected to preparative TLC using methanol containing aqueous ammonia and chloroform (concentration, 10%) as the developing solvent to obtain the title compound (10.6 mg, 73%) as pale yellow amorphous substance.

$^1$H NMR DMSO-$d_6$: 11.47 (s, 0.1H), 11.37 (s, 0.9H), 9.11 (s, 1H), 8.09 (s, 0.9H), 7.48 (s, 0.1H), 6.94 (d, 1H, J=8.2 Hz), 6.60 (d, 1H, J=2.3 Hz), 6.54 (dd, 1H, J=8.2, 2.3 Hz), 4.33-4.50 (m, 1H), 2.50-4.07 (m, 12H), 2.19-2.34 (m, 2H), 1.80-2.00 (m, 2H), 1.58-1.65 (m, 1H), 0.70-1.43 (m, 6H), 0.38-0.53 (m, 2H), 0.02-0.16 (m, 2H)

Example 37

Synthesis of 5-chloro-3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one

[Formula 54]

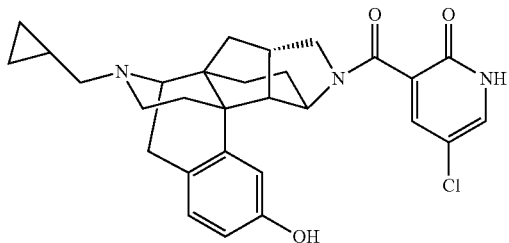

(1S,3aR,5aS,6R,11bR,11cS)-14-(Cyclopropylmethyl)-2,33a,4,5,6,7,11c-octahydro-1H-6,11b-(epiminoethano)-1,5a-methanonaphtho[1,2-e]indol-10-ol (20 mg, 57 mol), 5-chloro-2-oxo-1,2-dihydropyridine-3-carboxylic acid (22 mg, 0.13 mmol), diisopropylethylamine (50 μL, 0.29 mmol), and HATU (72 mg, 0.13 mmol) were reacted in the same manner as that of Example 1, except that THF (1 mL) alone was used as the solvent. To the reaction solution, a 1.4 N solution of ammonia in methanol was added to terminate the reaction, and then the reaction solution was concentrated under reduced pressure. The residue was suspended in saturated aqueous sodium hydrogen carbonate, and then the suspension was extracted with chloroform. The organic layer was dried over anhydrous sodium sulfate, the insoluble substance was separated by filtration, and then the filtrate was concentrated under reduced pressure. The obtained residue was subjected to column chromatography (aminosilica gel, 8 g) using methanol and ethyl acetate (concentration gradient, 0 to 80%) as the elution solvent, and thereby purified to obtain the title compound (11.6 mg, 40%) as brown amorphous substance.

$^1$H NMR DMSO-$d_6$: 11.99 (br s, 1H), 9.06 (br s, 1H), 7.68 (s, 0.7H), 7.59 (s, 0.3H), 7.48 (d, 1H, J=2.3 Hz), 6.89 (d, 0.7H, J=8.2 Hz), 6.85 (d, 0.3H, J=8.2 Hz), 6.40-6.56 (m, 2H), 4.25-4.32 (m, 0.7H), 3.93-3.98 (m, 0.3H), 3.78-3.84 (m, 0.3H), 2.11-3.62 (m, 10.7H), 1.68-1.91 (m, 2H), 1.48-1.63 (m, 1H), 0.87-1.46 (m, 4H), 0.50-0.79 (m, 2H), 0.29-0.47 (m, 2H), 0.06-0.12 (m, 2H)

Example 38

Synthesis of 5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1,3-dimethylpyrimidine-2,4(1H,3H)-dione

[Formula 55]

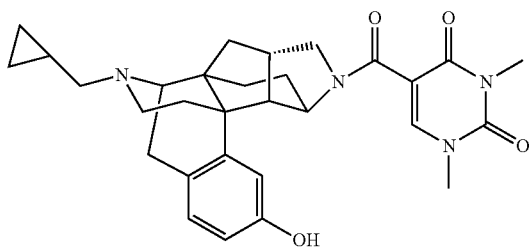

In the same manner as that of Example 1, (1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indol-10-ol (35 mg, 98 μmol), 1,3-dimethyl-2,4-dioxo-1,2,3,4-tetrahydropyrimidine-5-carboxylic acid (35 mg, 0.19 mmol), triethylamine (70 μL, 0.50 mmol), and HATU (145 mg, 0.38 mmol) were reacted, then to the reaction solution, a 2 N solution of ammonia in methanol was added to terminate the reaction, and then the reaction solution was concentrated under reduced pressure. The residue was suspended in 6% aqueous ammonia (20 mL), and the suspension was extracted with ethyl acetate (15 mL×2). The combined organic layers were washed with saturated brine (10 mL), and then dried over anhydrous magnesium sulfate. The insoluble substance was separated by filtration, and then the filtrate was concentrated under reduced pressure. The residue was subjected to column chromatography (aminosilica gel, 10 g) using methanol and ethyl acetate (concentration gradient, 0 to 30%) as the elution solvent, and thereby purified. The obtained syrup-like substance was dissolved in methanol (0.2 mL), then powdered by adding t-butyl methyl ether (3 mL) to the solution, and collected by filtration to obtain the title compound (39 mg, 76%) as white powder.

$^1$H NMR CD$_3$OD: 7.82 (s, 1H), 6.92-6.98 (m, 1H), 6.52-6.65 (m, 2H), 4.53-4.62 (m, 1H), 4.02-4.18 (m, 1H), 3.50-3.80 (m, 2H), 3.42 (s, 2H), 3.37 (s, 1H), 3.33 (a, 2H), 3.31 (s, 1H), 2.81-3.18 (m, 5H), 2.57-2.59 (m, 1H), 2.30-2.38 (m, 2H), 1.93-2.09 (m, 2H), 1.67-1.78 (m, 1H), 1.43-1.59 (m, 2H), 1.10-1.29 (m, 2H), 0.81-0.95 (m, 2H), 0.44-0.53 (m, 2H), 0.08-0.17 (m, 2H)

Example 39

Synthesis of 6-((1S,3aR,5aS,6R,11bR,11cS)-14-(cyclopropylmethyl)-10-methoxy-2,3,3a,4,5,6,7,11c-octahydro-1H-6,11b-(epiminoethano)-1,5a-methanonaphtho[1,2-e]indole-3-carbonyl)pyridin-2(1H)-one

[Formula 56]

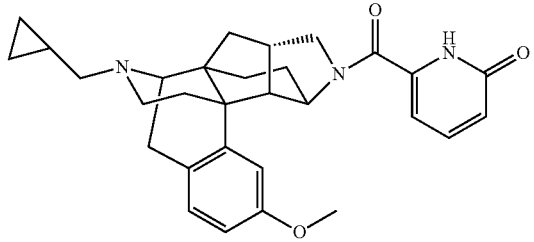

The experiment was performed in the same manner as that of Example 1.

(1S,3aR,5aS,6R,11bR,11cS)-14-(Cyclopropylmethyl)-10-methoxy-2,3,3a,4,5,6,7,11c-octahydro-1H-6,11b-(epiminoethano)-1,5a-methanonaphtho[1,2-e]indole (82 mg, 0.23 mmol) prepared according to the method described in WO2013/035833, Example 67, triethylamine (200 μL, 1.43 mmol), and HATU (167 mg, 0.44 mmol) were reacted. Then, to the reaction solution, ethanolamine (200 μL) and methanol (1 mL) were added to terminate the reaction, and then the reaction mixture was diluted with ethyl acetate (50 mL), and washed with 6% aqueous ammonia (50 mL). The aqueous layer was extracted with chloroform (30 mL×2), and the combined organic layers were dried over anhydrous sodium sulfate. The insoluble substance was separated by filtration, and then the filtrate was concentrated under reduced pressure. The residue was subjected to column chromatography (aminosilica gel, 7 g) using methanol and ethyl acetate (concentration gradient, 10 to 50%) as the elution solvent, and thereby purified. The obtained syrup-like substance was dissolved in methanol (0.2 mL), and then powdered by adding t-butyl methyl ether (3 mL) to the solution. The obtained powder was dried at 100° C. for 16 hours under reduced pressure to obtain the title compound (87 mg, 100%) as white amorphous substance-like substance.

$^1$H NMR DMSO-$d_6$: 7.5 (br s, 1H), 6.97-7.03 (m, 1H), 6.45-6.73 (m, 4H), 4.40-4.45 (m, 0.7H), 3.84-3.89 (m, 0.3H), 3.69 (s, 3H), 3.55-3.62 (m, 1H), 2.95-3.22 (m, 4H), 2.79-2.84 (m, 2H), 2.13-2.62 (m, 4H), 1.79-1.87 (m, 2H), 1.26-1.60 (m, 3H), 0.99-1.14 (m, 3H), 0.70-0.74 (m, 1H), 0.54-0.61 (m, 1H), 0.39-0.40 (m, 2H), 0.00-0.07 (m, 2H)

Example 40

Opioid Receptor Function Test

The functional activities of the compounds provided by the present invention on the μ, δ, and κ opioid receptors were investigated.

Method:

The test was performed by using Lance Ultra cAMP Kit (PerkinElmer) according to a method predetermined for the kit. In the evaluation of the agonistic activity, CHO cells expressing each of the human opioid receptors (δ, μ, and κ, accession numbers and catalog numbers are mentioned below) and 10 μM of each test compound were reacted for 30 minutes in an assay buffer (1×HBSS, 1 M HEPES, pH 7.4, 250 mM IBMX (isobutylmethylxanthine), 7.5% BSA) in the presence of forskolin. Subsequently, the cAMP detection reagent included in the kit was added, and 1 hour afterward, time-resolved fluorescence measurement was performed by using the EnVision plate reader (PerkinElmer). The test compounds and the control drugs (δ: SNC80, μ: DAMGO, κ: U-69593) were evaluated in a concentration range of $10^{-12}$ to $10^{-5}$ M, a dose-response curve of each test compound was obtained from the fluorescence values at 665 nm, and $EC_{50}$ value and the $E_{max}$ value were calculated. The $E_{max}$ value was calculated as a ratio of the maximum reaction of the test compound to the maximum reaction of each control drug, which is taken as 100%.

SNC80:
(+)-4-[(αR)-α-((2S,5R)-4-Allyl-2,5-dimethyl-1-piperazinyl)-3-methoxybenzyl]-N,N-diethylbenzamide
DAMGO:
[D-Ala$^2$,N-MePhe$^4$,Gly-ol]enkephalin
U-69593:
(+)-(5α,7α,8β)-N-Methyl-N-[7-(1-pyrrolidinyl)-1-oxaspiro[4.5]dec-8-yl]benzeneacetamide
Accession Numbers and Catalogue Numbers
δ: Catalog No. CT4607, Accession No. NM_000911.2
μ: Catalog No. CT4605, Accession No. NM_000914
κ: Catalog No. CT4606, Accession No. NM_000912
(ChanTest Corporation)

TABLE 6

| Example | δ receptor | | μ receptor | | κ receptor | |
|---|---|---|---|---|---|---|
| | $EC_{50}$ Value (nM) | Emax (%) | $EC_{50}$ Value (nM) | Emax (%) | $EC_{50}$ Value (nM) | Emax (%) |
| 1 | <3 | 88 | N.C. | 8.3* | >1 | 12 |
| 3 | <3 | 98 | >1 | 20 | <1 | 15 |
| 4 | <3 | 86 | N.C. | 5.5* | >10 | 27 |

TABLE 6-continued

| Example | δ receptor | | μ receptor | | κ receptor | |
|---|---|---|---|---|---|---|
| | $EC_{50}$ Value (nM) | Emax (%) | $EC_{50}$ Value (nM) | Emax (%) | $EC_{50}$ Value (nM) | Emax (%) |
| 5 | <3 | 81 | >1 | 9.7 | <1 | 20 |
| 6 | <3 | 97 | >10 | 7.7 | N.C. | 3.2* |
| 7 | <3 | 99 | >1 | 10 | N.C. | −0.9* |
| 8 | <3 | 70 | >1 | 8.6 | <1 | 21 |
| 9 | <3 | 74 | <1 | 15 | <1 | 14 |
| 10 | <3 | 74 | N.C. | 6.0* | N.C. | −0.7* |
| 11 | <3 | 76 | >1 | 11 | N.C. | −2.5* |
| 14 | <3 | 95 | >1 | 8.1 | N.C. | 5.7* |
| 16 | <3 | 92 | >1 | 19 | <1 | 29 |
| 19 | <3 | 91 | >1 | 19 | N.C. | 0.6* |
| 28 | <3 | 92 | >1 | 16 | <1 | 13 |
| 31 | <3 | 97 | >10 | 7.7 | N.C. | 3.2* |
| 32 | <3 | 70 | >1 | 8.6 | <1 | 21 |

N.C.: Since the maximum reaction was not reached at the maximum concentration (10 μM), the $ED_{50}$ value was not calculated.
*Since the maximum reaction was not reached at the maximum concentration, a reaction rate at the maximum concentration is mentioned as a reference value.

As shown in Table 6, it was confirmed that the compounds of the present invention have potent agonistic activities for the opioid δ receptor, but do not have agonistic activity or have only very weak agonistic activity for the μ and κ receptors.

Example 41

Mouse Elevated Plus Maze Test
(Test Method)
For the test, 5 to 6 weeks old C57BL/6N male mice were used. On a plus maze apparatus consisting of a wall-less running route (open arm, width 6 cm, length 30 cm) and a running route with a wall (closed arm, width 6 cm, length 30 cm, height of wall 15 cm), and having a height of 40 cm, a mouse was put so as to be directed to the running route with a wall, and allowed to spontaneously enter into the plus maze. Each test substance was dissolved in saline or 0.005 N HCl in saline, and subcutaneously administered on the back 30 minutes before the start of the test. At the time of the start of the test, video recording with a video camera was started, the time at which the mouse entered into the plus maze is considered to be the start of the test, and exploratory behavior was recorded for 5 minutes. On the basis of the video image, staying time in the running routes were determined, and wall-less running route staying time ratio (%) was calculated.
(Test Results)
As shown in FIGS. 1 and 2, from this experiment, it was found that subcutaneous administrations of the compound 1 (the compound described in Example 1) and the compound 7 (the compound described in Example 7) at a dose of 3 mg/kg and 10 mg/kg, respectively, significantly increased the wall-less running route staying time ratio and thus it was confirmed that they exhibit anxiolytic-like effects. The compound 3 (the compound described in Example 3), the compound 9 (the compound described in Example 9), and the compound 10 (the compound described in Example 10) also showed a tendency of increasing the wall-less running route staying time ratio (FIGS. 3 to 5).

Example 42

Rat Elevated Plus Maze Test
Anxiolytic effects of the compounds provided by the present invention were investigated by the rat elevated plus maze test.

(Test Method)

For the test, 7 to 9 weeks old Wistar male rats were used. On a plus maze apparatus consisting of a wall-less running route (width 10 cm, length 50 cm) and a running route with a wall (width 10 cm, length 50 cm, height of wall 30 cm), and having a height of 50 cm, a rat was put so as to be directed to the running route with a wall, and allowed to spontaneously enter into the plus maze, and exploratory behavior was observed for 5 minutes. Each test substance was dissolved in a 4.5% aqueous solution of cyclodextrin, and orally administered 2 hours before the start of the test. The test data were automatically analyzed by using video image action analysis software (Smart3.0, PanLab S.L., PanLab), and wall-less running route staying time ratio (%) was calculated.

(Test Results)

As shown in FIG. 6, from this experiment, it was found that oral administration of 3 mg/kg of each of the compound 7 (the compound described in Example 7), the compound 3 (the compound described in Example 3), and the compound 10 (the compound described in Example 10) significantly increased the wall-less running route staying time ratio, and thus it was confirmed that they exhibit anxiolytic-like effects.

Example 43 hERG (Human Ether-a-go-go-Related Gene) Potassium Channel Inhibition Test (Test Method)

The test was performed with Port-a-Patch automatic patch clump apparatus (Nanion Technologies) using hERG channel-stably expressing CHO cells (purchased from Channelopathy Foundation). The membrane potential of the cells was maintained at −80 mV, then there were applied a depolarization pulse at +20 mV for 1.5 seconds, and a following test pulse at −50 mV for 1.5 seconds at a frequency of 1 time per 10 seconds, and the hERG current was confirmed as a tail current induced by the test pulse. The test compound was dissolved in an extracellular fluid (137 mM NaCl, 4 mM KC, 1.8 mM $CaCl_2$, 1 mM $MgCl_2$, 10 mM D(+)-glucose, 10 mM HEPES, pH 7.4), and the solution was refluxed at room temperature for 5 minutes. The inhibition ratio was obtained from the ratio of the tail current value observed after the compound was applied based on the tail current value observed before the compound was applied, which was taken as 100%. For the test, we used cells that showed a peak tail current value not smaller than 300 pA, tail current run-down smaller than 10% of the initial current value, and leak current smaller than 200 pA.

(Test Results)

The test results are shown in Table 7.

In the table, the compounds 1, 3, 7, 9, and 10 are the compounds described in Examples 1, 3, 7, 9, and 10, respectively.

As clearly seen from the results shown in Table 7, all the test compounds showed only weak inhibitory effects.

On the other hand, it was revealed that the compounds disclosed in WO2013/35833 (Patent document 4) include those having potent hERG inhibitory effects.

TABLE 7

| Example | Concentration | hERG channel inhibitory action |
| --- | --- | --- |
| Compound 1 | 10 µM | <50% |
| Compound 3 | 10 µM | <50% |
| Compound 7 | 10 µM | <50% |
| Compound 9 | 10 µM | <50% |
| Compound 10 | 10 µM | <50% |

TABLE 7-continued

| Example | Concentration | hERG channel inhibitory action |
| --- | --- | --- |
| Comparative compound 1 | 10 µM | >50% |
| Comparative compound 2 | 10 µM | >50% |

Comparative Compound 1: Compound of WO2013/35833, Example 93 (Compound 104)
Comparative Compound 2: Compound of WO2013/35833, Example 205 (Compound 267)

Example 44

Hyperemotional Reaction Inhibition Test Using Olfactory Bulbectomized (OBX) Rat (Test Method)

According to the method of Saitoh et al. (Saitoh A, Yamada M, Yamada M, Takahashi K, Yamaguchi K, Murasawa H, Nakatani A, Tatsumi Y, Hirose N, and Kamei J: Antidepressant-like effects of the delta-opioid receptor agonist SNC80 ((+)-4-[(alphaR)-alpha-[(2S,5R)-2,5-dimethyl-4-(2-propenyl)-1-piperazinyl]-(3-methoxyphenyl)methyl]-N,N-diethylbenzamide) in an olfactory bulbectomized rat model, Brain Res., 2008, 1208:160-169), OBX rats were prepared by extracting the rat olfactory bulbs, and then breeding the rats in an isolated circumstance. Hyperemotional reaction was evaluated on the day 14 after the surgical operation and before the division into groups, and 2 hours after the administration on the days 1, 4, 7, 10, and 14 of the administration period according to the hyperemotional reaction evaluation criteria prepared by Gomita et al. (Gomita et al., Behavioral pharmacological and electroencephalographical studies of 7-chloro-1-methyl-5-phenyl-1H-1,5-benzodiazepine-2,4-(3H,5H:)-dione (Clobazam), Folia Pharmacologica Japonica, 82, 267 (1983)). The drug was subcutaneously administered once a day continuously over 14 days. As a positive control drug, fluoxetine, which is a selective serotonin reuptake inhibitor (SSRI), was used. As the solvent, a 1% cyclodextrin (CD) was used.

(Test Results)

Administration of 0.1 mg/kg of the test substance (the compound described in Example 7 mentioned above) significantly reduced the hyperemotional reactions of the OBX rats from the day 4 of the administration period compared with the solvent administration group, and restored the condition even to a level comparable to that of the rats of the sham surgery group on the day 7 of the administration period. Administration of 1 mg/kg of the test substance significantly reduced the hyperemotional reactions of the OBX rats from the day 1 of the administration period compared with the solvent administration group, and restored the condition even to a level comparable to that of the rats of the sham surgery group on the day 4 of the administration period. These effects were maintained until the day 14. On the other hand, administration of fluoxetine at 10 mg/kg significantly reduced the hyperemotional reactions of the OBX rats on the day 14 of the administration period compared with the solvent administration group.

From the above investigation, it was suggested that the test substance may possibly show antidepressant-like effects even with single administration, unlike SSRI. It was also suggested that tolerance may not be induced for the antidepressant-like action of the test substance.

Example 45

Reserpine-Induced Parkinson's Disease Model Mouse (Test Method)

ICR male mice (5 weeks old, Japan SLC) were obtained, and used after an acclimation period (5 to 12 days).

PD model was prepared with reference to the report of Hille et al. (Exp. Neurol., 2001, 172:189). It was prepared by intraperitoneally administering reserpine (5 mg/kg) 18 to 24 hours before the start of the test. The test was performed by subcutaneously administering a test compound to each mouse on the day of the test, immediately putting the mouse into a cage for monitoring locomotor activity, and measuring the migration distance over 60 minutes.

(Test Results)

Since administration of the test substance (the compound described in Example 7 mentioned above) at 10 mg/kg significantly increased exploratory behavior, and also, a tendency of increase of standing up behavior was found, although it was not significant (P=0.16), Parkinson's disease-curing effect of the test substance was suggested.

Example 46

Evaluation Using Rat Cerebral Infarction-Induced Overactive Bladder Model (Test Method)

A transient middle cerebral artery occlusion model was prepared by using 8 weeks old SD male rats under isoflurane inhalation anesthesia. On the next day, the cervix was slightly cut open again under the isoflurane inhalation anesthesia, and a catheter for administration was fixed in the jugular vein, and led to the back. A cystometry operation was also performed, and the other end of a cannula inserted into the bladder was led to the back, and connected to a cannula swivel.

On the day 4 after the cerebral ischemia operation, cystometry was performed under no anesthesia and with no restraint. Intravesical pressure was measured for the stable period, then a medium was intravenously administered, and the value of the pressure was measured over about 30 minutes as a value before test substance administration. Then, the test substance was cumulatively and intravenously administered from the lowest dose at intervals of about 30 minutes, and the value was measured for about 30 minutes after each administration. For the rats determined to show pollakiuria (urination interval was 10 minutes or shorter) in the measurement before the administration, static intravesical pressure, pressure at the time of urination, urination interval, and single urination amount were measured at each time point.

(Test Results)

The measurement results are shown in Table 8.

As clearly seen from the results shown in Table 8, the test substance (the compound described in Example 7 mentioned above) did not affect the static intravesical pressure and pressure at the time of urination at all the doses. On the other hand, the urination interval and single urination amount showed a dose-dependently increasing tendency, and therefore pollakiuria-improving action of the test substance was suggested.

TABLE 8

|  | n | Vehicle | 0.01 mg/kg | 0.1 mg/kg |
| --- | --- | --- | --- | --- |
| Static pressure (mmHg) | 5 | 10.6 ± 1.3 | 9.5 ± 1.3 | 9.6 ± 1.1 |
| Pressure at the time of urination (mmHg) | 5 | 41.4 ± 10.0 | 42.9 ± 10.7 | 42.8 ± 9.7 |
| Urination interval (sec) | 5 | 384.4 ± 63.2 | 450.7 ± 76.9 | 547.4 ± 122.5 |
| Single urination amount (g) | 5 | 0.288 ± 0.061 | 0.310 ± 0.068 | 0.403 ± 0.129 |

Mean ± S.E. (n = 5)

Example 47

Metabolic Stability Test (Test Method)

Human hepatic microsomes and a test substance were reacted for a certain period of time (0 to 60 minutes). The test substance, which was not metabolized in the reaction sample, was measured, and remaining ratio was calculated. The test substance-remaining ratio at the time when the reaction time is 0 hour is taken as 100%. The remaining ratio after incubation was plotted against time as a log-linear plot to obtain a regression line (y=100e$^{-kt}$, k=inclination of straight line: clearance rate constant), and metabolic clearance $CL_{int}$ (mL/min/kg) was calculated by using the following equation.

$$CL_{int}^* = k(-\min) \times 52.5 \text{ (mg MS protein/g liver)} \times 26 \text{ (g liver/kg)/MS protein (mg MS protein/mL)}$$

*: Davies, B. and Morris T., Physiological parameters in laboratory animals and humans, Pharm. Res., 10(7):1093-1095, 1993

(Test Results)

The test results are shown in Table 9.

TABLE 9

|  | Example 1 | Example 7 | Example 10 | Example 16 | Comparative compound 1 |
| --- | --- | --- | --- | --- | --- |
| Clint | 19 | 5.6 | 13 | 18 | 25 |

Comparative Compound 1: WO2013/35833, Example 93 (Compound 104)

As clearly seen from the results shown in Table 9, it was revealed that the compounds of the present invention have superior metabolic stability. On the other hand, it was revealed that the compounds described in WO2013/35833 (Patent document 4) include those showing bad metabolic stability.

DESCRIPTION OF NOTATIONS

In FIGS. 1 to 6, the vertical axes indicate the wall-less running route staying time ratio, and the horizontal axes indicate the test drug and dose thereof.

What is claimed is:

1. A compound represented by the following formula (I):

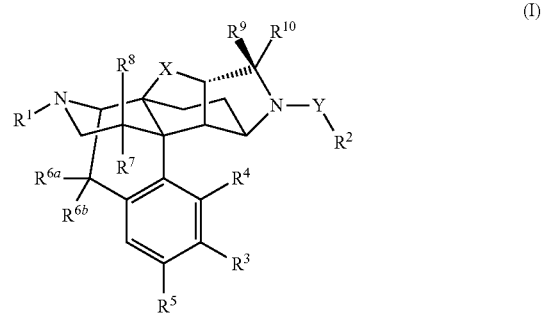

wherein:

R$^1$ represents hydrogen; C$_{1-10}$ alkyl; C$_{6-10}$ aryl; C$_{2-6}$ alkenyl; cycloalkylalkyl where the cycloalkyl moiety has 3 to 6 carbon atoms, and the alkylene moiety has 1 to 5 carbon atoms; aralkyl where the aryl moiety has 6 to 10 carbon atoms, and the alkylene moiety has 1 to 5 carbon atoms; $C_{3-6}$ cycloalkyl; or heteroarylalkyl where the heteroaryl moiety contains 1 to 4 heteroatoms selected from N, O and S as ring-constituting atoms, and the alkylene moiety has 1 to 5 carbon atoms, $R^2$ represents heterocyclic ring containing 1 to 4 heteroatoms selected from N, O and S and at least one carbon atom as ring-constituting atoms, containing at least one set of adjacent ring-constituting atoms bound by a double bond, and further substituted with at least one oxo group, $R^2$ binds to Y via a carbon atom as a ring-constituting atom of $R^2$, $R^3$, $R^4$, and $R^5$, which are the same or different, represent hydrogen; hydroxy; halogen; cyano; carbamoyl; $C_{1-6}$ alkoxy; $C_{6-10}$ aryloxy; $C_{1-6}$ alkanoyloxy; nitro; amino; $C_{1-8}$ alkylamino; $C_{6-10}$ arylamino; or acylamino where the acyl moiety has 2 to 6 carbon atoms, $R^{6a}$ and $R^{6b}$, which are the same or different, represent hydrogen; fluorine; or hydroxy, or $R^{6a}$ and $R^{6b}$ combine together to represent =O, $R^7$ and $R^8$, which are the same or different, represent hydrogen; fluorine; or hydroxy, $R^9$ and $R^{19}$, which are the same or different, represent hydrogen; $C_{1-6}$ alkyl; $C_{6-10}$ aryl; heteroaryl containing 1 to 4 heteroatoms selected from N, O and S as ring-constituting atoms; aralkyl where the aryl moiety has 6 to 10 carbon atoms, and the alkylene moiety has 1 to 5 carbon atoms; heteroarylalkyl where the heteroaryl moiety contains 1 to 4 heteroatoms selected from N, O and S as ring-constituting atoms, and the alkylene moiety has 1 to 5 carbon atoms; cycloalkylalkyl where the cycloalkyl moiety has 3 to 6 carbon atoms, and the alkylene moiety has 1 to 5 carbon atoms; or $C_{2-6}$ alkenyl, X represents O or $CH_2$, and Y represents C(=O), provided that:

the $C_{1-10}$ alkyl as $R^1$; the alkylene moiety and cycloalkyl moiety of the cycloalkylalkyl where the cycloalkyl moiety has 3 to 6 carbon atoms, and the alkylene moiety has 1 to 5 carbon atoms as $R^1$; the alkylene moiety of the aralkyl where the aryl moiety has 6 to 10 carbon atoms, and the alkylene moiety has 1 to 5 carbon atoms as $R^1$; and the alkylene moiety of the heteroarylalkyl where the heteroaryl moiety contains 1 to 4 heteroatoms selected from N, O and S as ring-constituting atoms, and the alkylene moiety has 1 to 5 carbon atoms as $R^1$ may be substituted with at least one substituent selected from 1 to 6 halogens; hydroxy; $C_{1-6}$ alkoxy; $C_{6-10}$ aryloxy; $C_{1-6}$ alkanoyl; $C_{1-6}$ alkanoyloxy; carboxyl; alkoxycarbonyl where the alkoxy moiety has 1 to 6 carbon atoms; carbamoyl; alkylcarbamoyl where the alkyl moiety has 1 to 6 carbon atoms; dialkylcarbamoyl where each alkyl moiety has 1 to 6 carbon atoms; alkylsulfonyl where the alkyl moiety has 1 to 6 carbon atoms; aminosulfonyl; alkylsulfinyl where the alkyl moiety has 1 to 6 carbon atoms; alkylthio where the alkyl moiety has 1 to 6 carbon atoms; $C_{1-6}$ alkoxy substituted with 1 to 6 halogens; and arylcarbonyl where the aryl moiety has 6 to 10 carbon atoms, the $C_{6-10}$ aryl as $R^1$; the aryl moiety of the aralkyl where the aryl moiety has 6 to 10 carbon atoms, and the alkylene moiety has 1 to 5 carbon atoms as $R^1$; the aryl moiety of the $C_{6-10}$ aryloxy as $R^3$, $R^4$, or $R^5$; the aryl moiety of the $C_{6-10}$ arylamino as $R^3$, $R^4$, or $R^5$; the $C_{6-10}$ aryl as $R^9$ or $R^{10}$; the heteroaryl containing 1 to 4 heteroatoms selected from N, O and S as ring-constituting atoms as $R^9$ or $R^{10}$; the aryl moiety of the aralkyl where the aryl moiety has 6 to 10 carbon atoms, and the alkylene moiety has 1 to 5 carbon atoms as $R^9$ or $R^{10}$; and the heteroaryl moiety of the heteroarylalkyl where the heteroaryl moiety contains 1 to 4 heteroatoms selected from N, O and S as ring-constituting atoms, and the alkylene moiety has 1 to 5 carbon atoms as $R^9$ or $R^{10}$ may be substituted with at least one substituent selected from $C_{1-6}$ alkyl; $C_{1-6}$ alkoxy; $C_{1-6}$ alkanoyloxy; hydroxy; alkoxycarbonyl where the alkoxy moiety has 1 to 6 carbon atoms; carbamoyl; alkylcarbamoyl where the alkyl moiety has 1 to 6 carbon atoms; dialkylcarbamoyl where each alkyl moiety has 1 to 6 carbon atoms; halogen; nitro; cyano; $C_{1-6}$ alkyl substituted with 1 to 3 halogens; $C_{1-6}$ alkoxy substituted with 1 to 3 halogens; phenyl; heteroaryl containing 1 to 4 heteroatoms selected from N, O and S as ring-constituting atoms; phenoxy; phenylalkyl where the alkyl has 1 to 3 carbon atoms; and methylenedioxy, the heterocyclic ring as $R^2$ may have, besides the oxo group, the substituents that the $C_{6-10}$ aryl as $R^1$ defined above may have, when $R^1$ is $C_{1-10}$ alkyl, it may be substituted with, $NR^{11}R^{12}$, where $R^{11}$ and $R^{12}$, which are the same or different, represent hydrogen; $C_{1-10}$ alkyl; or aralkyl where the aryl moiety has 6 to 10 carbon atoms, and the alkylene moiety has 1 to 5 carbon atoms; or $R^{11}$, $R^{12}$, the nitrogen atom to which $R^{11}$ and $R^{12}$ bind, and optionally, 1 or 2 heteroatoms may combine together to form a 5- to 7-membered ring, and the alkylene moiety of the aralkyl where the aryl moiety has 6 to 10 carbon atoms, and the alkylene moiety has 1 to 5 carbon atoms as $R^1$ may be substituted with at least one substituent selected from phenyl, and $C_{1-6}$ alkyl substituted with 1 to 3 halogens, a tautomer or stereoisomer of the compound, or a pharmaceutically acceptable salt thereof, or a solvate thereof.

2. The compound, a tautomer or stereoisomer of the compound, or a pharmaceutically acceptable salt thereof, or a solvate thereof according to claim 1, wherein $R^1$ is $C_{1-10}$ alkyl; cycloalkylalkyl where the cycloalkyl moiety has 3 to 6 carbon atoms, and the alkylene moiety has 1 to 5 carbon atoms; or aralkyl where the aryl moiety has 6 to 10 carbon atoms, and the alkylene moiety has 1 to 5 carbon atoms.

3. The compound, a tautomer or stereoisomer of the compound, or a pharmaceutically acceptable salt thereof, or a solvate thereof according to claim 1, wherein $R^1$ is cycloalkylalkyl where the cycloalkyl moiety has 3 to 6 carbon atoms, and the alkylene moiety has 1 to 5 carbon atoms.

4. The compound, a tautomer or stereoisomer of the compound, or a pharmaceutically acceptable salt thereof, or a solvate thereof according to claim 1, wherein $R^1$ is $C_{2-6}$ alkyl substituted with hydroxy; $C_{1-6}$ alkyl substituted with 1 to 6 halogens; or $C_{2-6}$ alkyl substituted with $C_{1-6}$ alkoxy.

5. The compound, a tautomer or stereoisomer of the compound, or a pharmaceutically acceptable salt thereof, or a solvate thereof according to claim 1, wherein $R^1$ is allyl, fluoropropyl, 2-(pyridin-3-yl)ethyl, 2-(methylsulfonyl)ethyl, or 2-(aminosulfonyl)ethyl.

6. The compound, a tautomer or stereoisomer of the compound, or a pharmaceutically acceptable salt thereof, or a solvate thereof according to claim 1, wherein $R^2$ is a 5- to 7-membered heterocyclic ring containing 1 to 4 heteroatoms selected from N, O and S and at least one carbon atom as ring-constituting atoms, containing at least one set of adjacent ring-constituting atoms bound by a double bond, and further substituted with at least one oxo group; or a heterocyclic ring consisting of the foregoing heterocyclic ring and a benzene ring condensed thereto.

7. The compound, a tautomer or stereoisomer of the compound, or a pharmaceutically acceptable salt thereof, or a solvate thereof according to claim 1, wherein $R^2$ is pyridine 1-oxide, which may be substituted with 1 to 4 substituents selected from $C_{1-10}$ alkyl substituted with 1 to 3 fluorine atoms, and unsubstituted $C_{1-10}$ alkyl.

8. The compound, a tautomer or stereoisomer of the compound, or a pharmaceutically acceptable salt thereof, or a solvate thereof according to claim 1, wherein $R^2$ is pyridine 1-oxide.

9. The compound, a tautomer or stereoisomer of the compound, or a pharmaceutically acceptable salt thereof, or a solvate thereof according to claim 1, wherein $R^2$ is pyridin-2(1H)-one, which may be substituted with 1 to 4 substituents selected from $C_{1-10}$ alkyl substituted with 1 to 3 fluorine atoms, and unsubstituted $C_{1-10}$ alkyl.

10. The compound, a tautomer or stereoisomer of the compound, or a pharmaceutically acceptable salt thereof, or a solvate thereof according to claim 1, wherein $R^2$ is pyridin-2(1H)-one; 1-($C_{1-6}$ alkyl)pyridin-2(1H)-one; or 6-($C_{1-6}$ alkyl)pyridin-2(1H)-one.

11. The compound, a tautomer or stereoisomer of the compound, or a pharmaceutically acceptable salt thereof, or a solvate thereof according to claim 1, wherein $R^2$ is pyridin-4(1H)-one, which may be substituted with 1 to 4 substituents selected from $C_{1-10}$ alkyl substituted with 1 to 3 fluorine atoms, and unsubstituted $C_{1-10}$ alkyl.

12. The compound, a tautomer or stereoisomer of the compound, or a pharmaceutically acceptable salt thereof, or a solvate thereof according to claim 1, wherein $R^2$ is pyridin-4(1H)-one, or 1-($C_{1-6}$ alkyl)pyridin-4(1H)-one.

13. The compound, a tautomer or stereoisomer of the compound, or a pharmaceutically acceptable salt thereof, or a solvate thereof according to claim 1, wherein $R^2$ is pyridazin-3(2H)-one, which may be substituted with 1 to 3 substituents selected from $C_{1-10}$ alkyl substituted with 1 to 3 fluorine atoms, and unsubstituted $C_{1-10}$ alkyl.

14. The compound, a tautomer or stereoisomer of the compound, or a pharmaceutically acceptable salt thereof, or a solvate thereof according to claim 1, wherein $R^2$ is pyridazin-3 (2H)-one.

15. The compound, a tautomer or stereoisomer of the compound, or a pharmaceutically acceptable salt thereof, or a solvate thereof according to claim 1, wherein $R^2$ is pyrazin-2(1H)-one, which may be substituted with 1 to 3 substituents selected from $C_{1-10}$ alkyl and $C_{1-10}$ alkyl substituted with 1 to 3 fluorine atoms.

16. The compound, a tautomer or stereoisomer of the compound, or a pharmaceutically acceptable salt thereof, or a solvate thereof according to claim 1, wherein $R^2$ is pyrazin-2(1H)-one.

17. The compound, a tautomer or stereoisomer of the compound, or a pharmaceutically acceptable salt thereof, or a solvate thereof according to claim 1, wherein $R^2$ is 4H-pyran-4-one, or 2H-pyran-2-one, which may be substituted with 1 to 3 substituents selected from $C_{1-10}$ alkyl substituted with 1 to 3 fluorine atoms, and unsubstituted $C_{1-10}$ alkyl.

18. The compound, a tautomer or stereoisomer of the compound, or a pharmaceutically acceptable salt thereof, or a solvate thereof according to claim 1, wherein $R^2$ is 4H-pyran-4-one, or 2H-pyran-2-one.

19. The compound, a tautomer or stereoisomer of the compound, or a pharmaceutically acceptable salt thereof, or a solvate thereof according to claim 1, wherein $R^2$ is quinolin-2(1H)-one, which may be substituted with 1 to 3 substituents selected from $C_{1-10}$ alkyl substituted with 1 to 3 fluorine atoms, and unsubstituted $C_{1-10}$ alkyl.

20. The compound, a tautomer or stereoisomer of the compound, or a pharmaceutically acceptable salt thereof, or a solvate thereof according to claim 1, wherein $R^2$ is quinolin-2(1H)-one.

21. The compound, a tautomer or stereoisomer of the compound, or a pharmaceutically acceptable salt thereof, or a solvate thereof according to claim 1, wherein $R^2$ is pyrimidin-4(3H)-one, or pyrimidine-2,4(1H,3H)-dione, which may be substituted with 1 to 3 substituents selected from $C_{1-10}$ alkyl substituted with 1 to 3 fluorine atoms, and unsubstituted $C_{1-10}$ alkyl.

22. The compound, a tautomer or stereoisomer of the compound, or a pharmaceutically acceptable salt thereof, or a solvate thereof according to claim 1, wherein $R^2$ is pyrimidin-4(3H)-one, or pyrimidine-2,4(1H,3H)-dione.

23. The compound, a tautomer or stereoisomer of the compound, or a pharmaceutically acceptable salt thereof, or a solvate thereof according to claim 1, wherein X is $CH_2$.

24. The compound, a tautomer or stereoisomer of the compound, or a pharmaceutically acceptable salt thereof, or a solvate thereof according to claim 1, wherein one of $R^3$ and $R^4$ is hydroxy, and the other is hydrogen.

25. The compound, a tautomer or stereoisomer of the compound, or a pharmaceutically acceptable salt thereof, or a solvate thereof according to claim 1, wherein $R^3$ is halogen; cyano; carbamoyl; $C_{1-6}$ alkoxy; $C_{1-6}$ alkanoyloxy; amino; or acylamino where the acyl moiety has 2 to 6 carbon atoms, $R^4$ is hydrogen or hydroxy, and $R^5$ is hydrogen.

26. The compound, a tautomer or stereoisomer of the compound, or a pharmaceutically acceptable salt thereof, or a solvate thereof according to claim 1, wherein $R^3$ is hydroxy; carbamoyl; or $C_{1-6}$ alkanoyloxy, $R^4$ is hydrogen, and $R^5$ is hydrogen.

27. The compound, a tautomer or stereoisomer of the compound, or a pharmaceutically acceptable salt thereof, or a solvate thereof according to claim 1, wherein $R^3$ is hydroxy, $R^4$ is hydrogen, and $R^5$ is hydrogen.

28. The compound, a tautomer or stereoisomer of the compound, or a pharmaceutically acceptable salt thereof, or a solvate thereof according to claim 1, wherein all of $R^3$, $R^4$, and $R^5$ are hydrogens.

29. The compound, a tautomer or stereoisomer of the compound, or a pharmaceutically acceptable salt thereof, or a solvate thereof according to claim 1, wherein all of $R^{6a}$, $R^{6b}$, $R^7$, $R^8$, $R^9$, and $R^{10}$ are hydrogens.

30. The compound represented by the formula (I), a tautomer or stereoisomer of the compound, or a pharmaceutically acceptable salt thereof, or a solvate thereof according to claim 1, wherein:

$R^5$, $R^{6a}$, $R^{6b}$, $R^7$, $R^8$, $R^9$, and $R^{10}$ are hydrogens, $R^1$ is hydrogen; $C_{1-6}$ alkyl; $C_{2-6}$ alkenyl; cycloalkylalkyl where the cycloalkyl moiety has 3 to 6 carbon atoms, and the alkylene moiety has 1 to 5 carbon atoms; or aralkyl where the aryl moiety has 6 to 10 carbon atoms, and the alkylene moiety has 1 to 5 carbon atoms, $R^2$ is a 5- to 7-membered heterocyclic ring containing 1 to 4 heteroatoms selected from N, O and S and at least one carbon atom as ring-constituting atoms, containing at least one set of adjacent ring-constituting atoms bound by a double bond, and further substituted with at least one oxo group; or a heterocyclic ring consisting of the foregoing heterocyclic ring and a benzene ring condensed thereto, $R^2$ binds to Y via a carbon atom of $R^2$ as a ring-constituting atom, $R^3$ and $R^4$, which are the same or different, represent hydrogen; hydroxy; halogen; cyano; carbamoyl; $C_{1-6}$ alkoxy; $C_{6-10}$ aryloxy; $C_{1-6}$ alkanoyloxy; amino; or acylamino where the acyl moiety has 2 to 6 carbon atoms, X is $CH_2$, and Y is $C(=O)$, provided that:

the $C_{1-6}$ alkyl as $R^1$; the alkylene moiety and cycloalkyl moiety of the cycloalkylalkyl where the cycloalkyl moiety has 3 to 6 carbon atoms, and the alkylene moiety has 1 to 5 carbon atoms as $R^1$; and the alkylene moiety of the aralkyl where the aryl moiety has 6 to 10 carbon atoms, and the alkylene moiety has 1 to 5 carbon atoms as $R^1$ may be substituted with at least one substituent selected from 1 to 6 halogens; hydroxy; $C_{1-6}$ alkoxy; $C_{6-10}$ aryloxy; $C_{1-6}$ alkanoyl; $C_{1-6}$ alkanoyloxy; carboxyl; alkoxycarbonyl where the alkoxy moiety has 1 to 6 carbon atoms; carbamoyl; alkylcarbamoyl where the alkyl moiety has 1 to 6 carbon atoms; dialkylcarbamoyl where each alkyl moiety has 1 to 6 carbon atoms; alkylsulfonyl where the alkyl moiety has 1 to 6 carbon atoms; aminosulfonyl; alkylsulfinyl where the alkyl moiety has 1 to 6 carbon atoms; alkylthio where the alkyl moiety has 1 to 6 carbon atoms; $C_{1-6}$ alkoxy substituted with 1 to 6 halogens; and arylcarbonyl where the aryl moiety has 6 to 10 carbon atoms, the aryl moiety of the aralkyl where the aryl moiety has 6 to 10 carbon atoms, and the alkylene moiety has 1 to 5 carbon atoms as $R^1$; and the aryl moiety of the $C_{6-10}$ aryloxy as $R^3$ or $R^4$ may be substituted with at least one substituent selected from $C_{1-6}$ alkyl; $C_{1-6}$ alkoxy; $C_{1-6}$ alkanoyloxy; hydroxy; alkoxycarbonyl where the alkoxy moiety has 1 to 6 carbon atoms; carbamoyl; alkylcarbamoyl where the alkyl moiety has 1 to 6 carbon atoms; dialkylcarbamoyl where each alkyl moiety has 1 to 6 carbon atoms; halogen; nitro; cyano; $C_{1-6}$ alkyl substituted with 1 to 3 halogens; $C_{1-6}$ alkoxy substituted with 1 to 3 halogens; phenyl; heteroaryl containing 1 to 4 heteroatoms selected from N, O and S as ring-constituting atoms; phenoxy; phenylalkyl where the alkyl has 1 to 3 carbon atoms; and methylenedioxy, the heterocyclic ring as $R^2$ may have, besides the oxo group, at least one of the substituents which the aryl moiety of the aralkyl where the aryl moiety has 6 to 10 carbon atoms, and the alkylene moiety has 1 to 5 carbon atoms as $R^1$ may have, and the alkylene moiety of the aralkyl where the aryl moiety has 6 to 10 carbon atoms, and the alkylene moiety has 1 to 5 carbon atoms as $R^1$ may be substituted with at least one substituent selected from phenyl, and $C_{1-6}$ alkyl substituted with 1 to 3 halogens.

31. The compound, a tautomer or stereoisomer of the compound, or a pharmaceutically acceptable salt thereof, or a solvate thereof according to claim 30, wherein $R^1$ is $C_{1-6}$ alkyl; cycloalkylalkyl where the cycloalkyl moiety has 3 to 6 carbon atoms, and the alkylene moiety has 1 to 5 carbon atoms; or aralkyl where the aryl moiety has 6 to 10 carbon atoms, and the alkylene moiety has 1 to 5 carbon atoms.

32. The compound, a tautomer or stereoisomer of the compound, or a pharmaceutically acceptable salt thereof, or a solvate thereof according to claim 30, wherein $R^1$ is cycloalkylalkyl where the cycloalkyl moiety has 3 to 6 carbon atoms, and the alkylene moiety has 1 to 5 carbon atoms.

33. The compound, a tautomer or stereoisomer of the compound, or a pharmaceutically acceptable salt thereof, or a solvate thereof according to claim 30, wherein $R^1$ is $C_{2-6}$ alkyl substituted with hydroxy; $C_{1-6}$ alkyl substituted with 1 to 6 halogens; or $C_{2-6}$ alkyl substituted with $C_{1-6}$ alkoxy.

34. The compound, a tautomer or stereoisomer of the compound, or a pharmaceutically acceptable salt thereof, or a solvate thereof according to claim 30, wherein $R^1$ is allyl, fluoropropyl, 2-(pyridin-3-yl)ethyl, 2-(methylsulfonyl)ethyl, or 2-(aminosulfonyl)ethyl.

35. The compound, a tautomer or stereoisomer of the compound, or a pharmaceutically acceptable salt thereof, or a solvate thereof according to claim 30, wherein $R^2$ is pyridine 1-oxide, pyridin-2(1H)-one, pyridin-4(1H)-one, pyridazin-3(2H)-one, pyrazin-2(1H)-one, 4H-pyran-4-one, 2H-pyran-2-one, quinolin-2(1H)-one, pyrimidin-4(3H)-one, or pyrimidine-2,4(1H,3H)-dione, which may be substituted with a substituent selected from $C_{1-10}$ alkyl substituted with 1 to 3 fluorine atoms, and unsubstituted $C_{1-10}$ alkyl.

36. The compound, a tautomer or stereoisomer of the compound, or a pharmaceutically acceptable salt thereof, or a solvate thereof according to claim 30, wherein $R^2$ is pyridine 1-oxide, which may be substituted with 1 to 4 substituents selected from $C_{1-10}$ alkyl and $C_{1-10}$ alkyl substituted with 1 to 3 fluorine atoms.

37. The compound, a tautomer or stereoisomer of the compound, or a pharmaceutically acceptable salt thereof, or a solvate thereof according to claim 30, wherein $R^2$ is pyridine 1-oxide.

38. The compound, a tautomer or stereoisomer of the compound, or a pharmaceutically acceptable salt thereof, or a solvate thereof according to claim 30, wherein $R^2$ is pyridin-2(1H)-one, which may be substituted with 1 to 4 substituents selected from $C_{1-10}$ alkyl and $C_{1-10}$ alkyl substituted with 1 to 3 fluorine atoms.

39. The compound, a tautomer or stereoisomer of the compound, or a pharmaceutically acceptable salt thereof, or a solvate thereof according to claim 30, wherein $R^2$ is pyridin-2(1H)-one; 1-($C_{1-6}$ alkyl)pyridin-2(1H)-one; or 6-($C_{1-6}$ alkyl)pyridin-2(1H)-one.

40. The compound, a tautomer or stereoisomer of the compound, or a pharmaceutically acceptable salt thereof, or a solvate thereof according to claim 30, wherein $R^2$ is pyridin-4(1H)-one, which may be substituted with 1 to 4 substituents selected from $C_{1-10}$ alkyl substituted with 1 to 3 fluorine atoms, and unsubstituted $C_{1-10}$ alkyl.

41. The compound, a tautomer or stereoisomer of the compound, or a pharmaceutically acceptable salt thereof, or a solvate thereof according to claim 30, wherein $R^2$ is pyridin-4(1H)-one, or 1-($C_{1-6}$ alkyl)pyridin-4(1H)-one.

42. The compound, a tautomer or stereoisomer of the compound, or a pharmaceutically acceptable salt thereof, or a solvate thereof according to claim 30, wherein $R^2$ is pyridazin-3(2H)-one, which may be substituted with 1 to 3 substituents selected from $C_{1-10}$ alkyl substituted with 1 to 3 fluorine atoms, and unsubstituted $C_{1-10}$ alkyl.

43. The compound, a tautomer or stereoisomer of the compound, or a pharmaceutically acceptable salt thereof, or a solvate thereof according to claim 30, wherein $R^2$ is pyridazin-3(2H)-one.

44. The compound, a tautomer or stereoisomer of the compound, or a pharmaceutically acceptable salt thereof, or a solvate thereof according to claim 30, wherein $R^2$ is pyrazin-2(1H)-one, which may be substituted with 1 to 3 substituents selected from $C_{1-10}$ alkyl substituted with 1 to 3 fluorine atoms, and unsubstituted $C_{1-10}$ alkyl.

45. The compound, a tautomer or stereoisomer of the compound, or a pharmaceutically acceptable salt thereof, or a solvate thereof according to claim 30, wherein $R^2$ is pyrazin-2(1H)-one.

46. The compound, a tautomer or stereoisomer of the compound, or a pharmaceutically acceptable salt thereof, or a solvate thereof according to claim 30, wherein $R^2$ is 4H-pyran-4-one, or 2H-pyran-2-one, which may be substituted with 1 to 3 substituents selected from $C_{1-10}$ alkyl substituted with 1 to 3 fluorine atoms, and unsubstituted $C_{1-10}$ alkyl.

47. The compound, a tautomer or stereoisomer of the compound, or a pharmaceutically acceptable salt thereof, or a solvate thereof according to claim 30, wherein $R^2$ is 4H-pyran-4-one, or 2H-pyran-2-one.

48. The compound, a tautomer or stereoisomer of the compound, or a pharmaceutically acceptable salt thereof, or a solvate thereof according to claim 30, wherein $R^2$ is quinolin-2(1H)-one, which may be substituted with 1 to 3 substituents selected from $C_{1-10}$ alkyl substituted with 1 to 3 fluorine atoms, and unsubstituted $C_{1-10}$ alkyl.

49. The compound, a tautomer or stereoisomer of the compound, or a pharmaceutically acceptable salt thereof, or a solvate thereof according to claim 30, wherein $R^2$ is quinolin-2(1H)-one.

50. The compound, a tautomer or stereoisomer of the compound, or a pharmaceutically acceptable salt thereof, or a solvate thereof according to claim 30, wherein $R^2$ is pyrimidin-4(3H)-one, or pyrimidine-2,4(1H,3H)-dione, which may be substituted with 1 to 3 substituents selected from $C_{1-10}$ alkyl substituted with 1 to 3 fluorine atoms, and unsubstituted $C_{1-10}$ alkyl.

51. The compound, a tautomer or stereoisomer of the compound, or a pharmaceutically acceptable salt thereof, or a solvate thereof according to claim 30, wherein $R^2$ is pyrimidin-4(3H)-one, or pyrimidine-2,4(1H,3H)-dione.

52. The compound, a tautomer or stereoisomer of the compound, or a pharmaceutically acceptable salt thereof, or a solvate thereof according to claim 30, wherein one of $R^3$ and $R^4$ is hydroxy, and the other is hydrogen.

53. The compound, a tautomer or stereoisomer of the compound, or a pharmaceutically acceptable salt thereof, or a solvate thereof according to claim 30, wherein $R^3$ is halogen; cyano; carbamoyl; $C_{1-6}$ alkoxy; $C_{1-6}$ alkanoyloxy; amino; or acylamino where the acyl moiety has 2 to 6 carbon atoms, and $R^4$ is hydrogen or hydroxy.

54. The compound, a tautomer or stereoisomer of the compound, or a pharmaceutically acceptable salt thereof, or a solvate thereof according to claim 30, wherein $R^3$ is hydroxy; carbamoyl; or $C_{1-6}$ alkanoyloxy, and $R^4$ is hydrogen.

55. The compound, a tautomer or stereoisomer of the compound, or a pharmaceutically acceptable salt thereof, or a solvate thereof according to claim 30, wherein $R^3$ is hydroxy, and $R^4$ is hydrogen.

56. The compound, a tautomer or stereoisomer of the compound, or a pharmaceutically acceptable salt thereof, or a solvate thereof according to claim 30, wherein $R^3$ and $R^4$ are hydrogens.

57. A compound selected from:
2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide,
4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide,
3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one,
3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide,
5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one,
3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one,
6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one,
3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-6-methylpyridin-2(1H)-one,
5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one,
6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one,
4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one,
5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrimidine-2,4(1H,3H)-dione,
3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-4(1H)-one,
2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-4(1H)-one,
4-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one,
6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridazin-3(2H)-one,
4-((1S,3aR,5aS,6R,11bR,11cS)-14-(cyclopropylmethyl)-10-hydroxy-2,3,3a,4,5,6,7,11c-octahydro-1H-6,11b-

(epiminoethano)-1,5a-methanonaphtho[1,2-e]indole-3-carbonyl)quinolin-2(1H)-one,
5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-2H-pyran-2-one,
2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-4H-pyran-4-one,
2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-4(1H)-one,
5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrazin-2(1H)-one,
2-((1S,3aR,5aS,6R,11bR,11cS)-10-acetoxy-14-(cyclopropylmethyl)-2,3,3a,4,5,6,7,11c-octahydro-1H-6,11b-(epiminoethano)-1,5a-methanonaphtho[1,2-e]indole-3-carbonyl)pyridine 1-oxide,
6-((1S,3aR,5aS,6R,11bR,11cS)-14-(cyclopropylmethyl)-2,3,3a,4,5,6,7,11c-octahydro-1H-6,11b-(epiminoethano)-1,5a-methanonaphtho[1,2-e]indole-3-carbonyl)pyridin-2(1H)-one,
3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrazin-2(1H)-one,
6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrimidine-2,4(1H,3H)-dione,
6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-ethylpyridin-2(1H)-one,
6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyrimidin-4(3H)-one, and
5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-ethylpyridin-2(1H)-one, a tautomer or stereoisomer of the compound, or a pharmaceutically acceptable salt thereof, or a solvate thereof.

58. The compound, a tautomer or stereoisomer of the compound, or a pharmaceutically acceptable salt thereof, or a solvate thereof according to claim 57, wherein the compound is
2-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridine 1-oxide.

59. The compound, a tautomer or stereoisomer of the compound, or a pharmaceutically acceptable salt thereof, or a solvate thereof according to claim 57,
wherein the compound is
3-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one.

60. The compound, a tautomer or stereoisomer of the compound, or a pharmaceutically acceptable salt thereof, or a solvate thereof according to claim 57,
wherein the compound is
6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)pyridin-2(1H)-one.

61. The compound, a tautomer or stereoisomer of the compound, or a pharmaceutically acceptable salt thereof, or a solvate thereof according to claim 57,
wherein the compound is
5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one.

62. The compound, a tautomer or stereoisomer of the compound, or a pharmaceutically acceptable salt thereof, or a solvate thereof according to claim 57,
wherein the compound is
6-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-methylpyridin-2(1H)-one.

63. The compound, a tautomer or stereoisomer of the compound, or a pharmaceutically acceptable salt thereof, or a solvate thereof according to claim 57,
wherein the compound is
5-((1S,3aR,5aS,6R,11bR,11cS)-14-(cyclopropylmethyl)-10-hydroxy-2,3,3a,4,5,6,7,11c-octahydro-1H-6,11b-(epiminoethano)-1,5a-methanonaphtho[1,2-e]indole-3-carbonyl)-1-ethylpyridin-2(1H)-one.

64. A medicament comprising the compound, a tautomer or stereoisomer of the compound, or a pharmaceutically acceptable salt thereof, or a solvate thereof according to claim 1.

65. A pharmaceutical composition comprising the compound, a tautomer or stereoisomer of the compound, or a pharmaceutically acceptable salt thereof, or a solvate thereof according to claim 1 as an active ingredient.

66. An analgesic comprising the compound, a tautomer or stereoisomer of the compound, or a pharmaceutically acceptable salt thereof, or a solvate thereof according to claim 1 as an active ingredient.

67. An antidepressant comprising the compound, a tautomer or stereoisomer of the compound, or a pharmaceutically acceptable salt thereof, or a solvate thereof according to claim 1 as an active ingredient.

68. An anxiolytic drug comprising the compound, a tautomer or stereoisomer of the compound, or a pharmaceutically acceptable salt thereof, or a solvate thereof according to claim 1 as an active ingredient.

69. A therapeutic agent for Parkinson's disease comprising the compound, a tautomer or stereoisomer of the compound, or a pharmaceutically acceptable salt thereof, or a solvate thereof according to claim 1 as an active ingredient.

70. A therapeutic agent for pollakiuria or urinary incontinence comprising the compound, a tautomer or stereoisomer of the compound, or a pharmaceutically acceptable salt thereof, or a solvate thereof according to claim 1 as an active ingredient.

71. A therapeutic agent for glaucoma comprising the compound, a tautomer or stereoisomer of the compound, or a pharmaceutically acceptable salt thereof, or a solvate thereof according to claim 1 as an active ingredient.

72. A method for ameliorating, preventing or treating pain, which comprises administering an effective amount of the compound, a tautomer or stereoisomer of the compound, or a pharmaceutically acceptable salt thereof, or a solvate thereof according to claim 1.

73. A method for ameliorating, preventing or treating pain in a human, which comprises administering an effective amount of the compound, a tautomer or stereoisomer of the compound, or a pharmaceutically acceptable salt thereof, or a solvate thereof according to claim 1 to the human.

74. A method for ameliorating, preventing or treating depression, which comprises administering an effective amount of the compound, a tautomer or stereoisomer of the compound, or a pharmaceutically acceptable salt thereof, or a solvate thereof according to claim 1.

75. A method for ameliorating, preventing or treating depression in a human, which comprises administering an effective amount of the compound, a tautomer or stereoisomer of the compound, or a pharmaceutically acceptable salt thereof, or a solvate thereof according to claim 1 to the human.

76. A method for ameliorating, preventing or treating anxiety, which comprises administering an effective amount of the compound, a tautomer or stereoisomer of the compound, or a pharmaceutically acceptable salt thereof, or a solvate thereof according to claim 1.

77. A method for ameliorating, preventing or treating anxiety in a human, which comprises administering an effective amount of the compound, a tautomer or stereoisomer of the compound, or a pharmaceutically acceptable salt thereof, or a solvate thereof according to claim 1 to the human.

78. A method for ameliorating or treating Parkinson's disease, which comprises administering an effective amount of the compound, a tautomer or stereoisomer of the compound, or a pharmaceutically acceptable salt thereof, or a solvate thereof according to claim 1.

79. A method for ameliorating or treating Parkinson's disease in a human, which comprises administering an effective amount of the compound, a tautomer or stereoisomer of the compound, or a pharmaceutically acceptable salt thereof, or a solvate thereof according to claim 1 to the human.

80. A method for ameliorating or treating pollakiuria or urinary incontinence, which comprises administering an effective amount of the compound, a tautomer or stereoisomer of the compound, or a pharmaceutically acceptable salt thereof, or a solvate thereof according to claim 1.

81. A method for ameliorating or treating pollakiuria or urinary incontinence in a human, which comprises administering an effective amount of the compound, a tautomer or stereoisomer of the compound, or a pharmaceutically acceptable salt thereof, or a solvate thereof according to claim 1 to the human.

82. A method for ameliorating or treating glaucoma, which comprises administering an effective amount of the compound, a tautomer or stereoisomer of the compound, or a pharmaceutically acceptable salt thereof, or a solvate thereof according to claim 1.

83. A method for ameliorating or treating glaucoma in a human, which comprises administering an effective amount of the compound, a tautomer or stereoisomer of the compound, or a pharmaceutically acceptable salt thereof, or a solvate thereof according to claim 1 to the human.

* * * * *

UNITED STATES PATENT AND TRADEMARK OFFICE
CERTIFICATE OF CORRECTION

PATENT NO. : 10,442,802 B2
APPLICATION NO. : 15/558026
DATED : October 15, 2019
INVENTOR(S) : H. Nagase et al.

Page 1 of 1

It is certified that error appears in the above-identified patent and that said Letters Patent is hereby corrected as shown below:

In the Specification

Column 27, Line 40, please change " 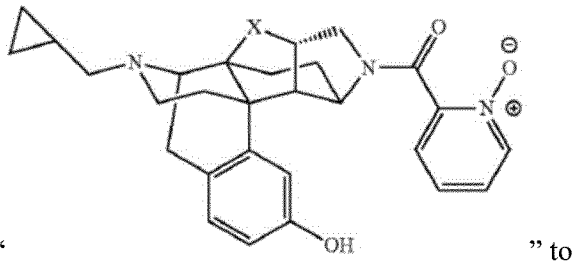 " to -- 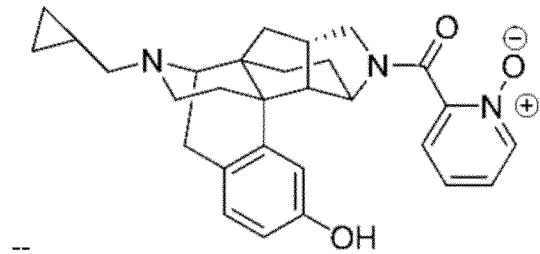 --.

Column 32, Line 6, please change "&L" to -- µL --.

Signed and Sealed this
Eighteenth Day of February, 2020

Andrei Iancu
*Director of the United States Patent and Trademark Office*